(12) United States Patent
Mirza et al.

(10) Patent No.: US 10,167,334 B2
(45) Date of Patent: Jan. 1, 2019

(54) TREATMENT OF CANCER USING ANTI-TGF-BETA AND PD-1 ANTIBODIES

(71) Applicants: XOMA TECHNOLOGY LTD., Berkeley, CA (US); THE REGENTS OF THE UNIVERSITY OF CALIFORNIA, Oakland, CA (US)

(72) Inventors: Amer M. Mirza, San Francisco, CA (US); Rosemary J. Akhurst, Tiburon, CA (US); Ou Li, San Francisco, CA (US)

(73) Assignees: XOMA TECHNOLOGY LTD., Berkeley, CA (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/089,579

(22) Filed: Apr. 3, 2016

(65) Prior Publication Data

US 2016/0289315 A1    Oct. 6, 2016

Related U.S. Application Data

(60) Provisional application No. 62/191,797, filed on Jul. 13, 2015, provisional application No. 62/143,016, filed on Apr. 3, 2015.

(51) Int. Cl.
  *C07K 16/22*  (2006.01)
  *C07K 16/28*  (2006.01)
  *A61K 39/00*  (2006.01)

(52) U.S. Cl.
  CPC .......... *C07K 16/22* (2013.01); *C07K 16/2803* (2013.01); *C07K 16/2818* (2013.01); *A61K 2039/507* (2013.01); *A61K 2039/57* (2013.01); *C07K 2317/51* (2013.01); *C07K 2317/515* (2013.01); *C07K 2317/56* (2013.01); *C07K 2317/565* (2013.01); *C07K 2317/73* (2013.01); *C07K 2317/76* (2013.01); *C07K 2317/92* (2013.01)

(58) Field of Classification Search
  None
  See application file for complete search history.

(56) References Cited

U.S. PATENT DOCUMENTS

| | | | |
|---|---|---|---|
| 4,179,337 A | 12/1979 | Davis et al. | |
| 4,676,980 A | 6/1987 | Segal et al. | |
| 4,816,567 A | 3/1989 | Cabilly et al. | |
| 4,975,278 A | 12/1990 | Senter et al. | |
| 5,057,313 A | 10/1991 | Shih et al. | |
| 5,223,409 A | 6/1993 | Ladner et al. | |
| 5,229,275 A | 7/1993 | Goroff | |
| 5,348,867 A | 9/1994 | Georgiou et al. | |
| 5,545,807 A | 8/1996 | Surani et al. | |
| 5,565,332 A | 10/1996 | Hoogenboom et al. | |
| 5,567,610 A | 10/1996 | Borrebaeck et al. | |
| 5,573,905 A | 11/1996 | Lerner et al. | |
| 5,589,369 A | 12/1996 | Seidman et al. | |
| 5,591,669 A | 1/1997 | Krimpenfort et al. | |
| 5,624,821 A | 4/1997 | Winter et al. | |
| 5,643,768 A | 7/1997 | Kawasaki | |
| 5,658,754 A | 8/1997 | Kawasaki | |
| 5,723,287 A | 3/1998 | Russell et al. | |
| 5,766,886 A | 6/1998 | Studnicka et al. | |
| 5,770,429 A | 6/1998 | Lonberg et al. | |
| 5,877,293 A | 3/1999 | Adair et al. | |
| 5,939,598 A | 8/1999 | Kucherlapati et al. | |
| 5,969,108 A | 10/1999 | McCafferty et al. | |
| 6,054,287 A | 4/2000 | Gao et al. | |
| 6,091,001 A | 7/2000 | Jakobovits et al. | |
| 6,114,598 A | 9/2000 | Kucherlapati et al. | |
| 6,194,551 B1 | 2/2001 | Idusogie et al. | |
| 6,306,393 B1 | 10/2001 | Goldenberg | |
| 6,657,103 B1 | 12/2003 | Kucherlapati et al. | |
| 6,664,114 B1 | 12/2003 | Lackie et al. | |
| 6,699,658 B1 | 3/2004 | Wittrup et al. | |
| 6,737,056 B1 | 5/2004 | Presta | |
| 6,808,710 B1 | 10/2004 | Wood et al. | |
| 6,833,268 B1 | 12/2004 | Green et al. | |
| 7,563,869 B2 | 7/2009 | Honjo et al. | |
| 7,579,186 B1 | 8/2009 | Sakamoto et al. | |
| 7,595,048 B2 | 9/2009 | Honjo et al. | |

(Continued)

FOREIGN PATENT DOCUMENTS

EP       0404097 A2    12/1990
WO    WO-81/01145 A1    4/1981

(Continued)

OTHER PUBLICATIONS

U.S. Appl. No. 62/014,181, Specification, filed Jun. 19, 2014.*
MacCallum et al. Antibody-antigen interactions: contact analysis and binding site topography. J Mol Biol. Oct. 11, 1996;262(5):732-45.*
Rudikoff et al. Single amino acid substitution altering antigen-binding specificity. Proc Natl Acad Sci U S A. Mar. 1982;79(6):1979-83.*
Vajdos et al. Comprehensive functional maps of the antigen-binding site of an anti-ErbB2 antibody obtained with shotgun scanning mutagenesis. J Mol Biol. Jul. 5, 2002;320(2):415-28.*
Abe et al., An assay for transforming growth factor-beta using cells transfected with a plasminogen activator inhibitor-1 promoter-luciferase construct, Anal. Biochem., 216(2):276-84 (1994).

(Continued)

*Primary Examiner* — Robert S Landsman
(74) *Attorney, Agent, or Firm* — Marshall, Gerstein & Borun LLP

(57) ABSTRACT

The present disclosure relates, in general, to combination therapy using an inhibitor of transforming growth factor beta (TGFβ) and an inhibitor of programmed cell death protein 1 (PD-1) for treating cancer or preventing recurrence of cancer diseases such as lung cancer, prostate cancer, breast cancer, hepatocellular cancer, esophageal cancer, colorectal cancer, pancreatic cancer, bladder cancer, kidney cancer, ovarian cancer, stomach cancer, fibrotic cancer, glioma and melanoma, and metastases thereof.

15 Claims, 8 Drawing Sheets

Specification includes a Sequence Listing.

(56) References Cited

U.S. PATENT DOCUMENTS

| | | | |
|---|---|---|---|
| 7,867,496 B2 | 1/2011 | Khanna et al. | |
| 7,927,593 B2 | 4/2011 | Jones et al. | |
| 7,943,743 B2 | 5/2011 | Korman et al. | |
| 8,008,449 B2 | 8/2011 | Korman et al. | |
| 8,088,905 B2 | 1/2012 | Collins et al. | |
| 8,133,979 B2 * | 3/2012 | Brinkmann | A61K 39/00 530/387.3 |
| 8,168,179 B2 | 5/2012 | Honjo et al. | |
| 8,217,149 B2 | 7/2012 | Irving et al. | |
| 8,246,955 B2 | 8/2012 | Honjo et al. | |
| 8,287,856 B2 | 10/2012 | Li et al. | |
| 8,354,509 B2 | 1/2013 | Carven et al. | |
| 8,552,154 B2 | 10/2013 | Freeman et al. | |
| 8,569,462 B2 | 10/2013 | Bedinger et al. | |
| 8,617,546 B2 | 12/2013 | Kang et al. | |
| 8,637,017 B2 * | 1/2014 | Cicortas Gunnarsson | C07K 16/30 424/133.1 |
| 8,735,553 B1 | 5/2014 | Li et al. | |
| 8,741,295 B2 | 6/2014 | Olive | |
| 8,779,105 B2 | 7/2014 | Korman et al. | |
| 8,926,976 B2 | 1/2015 | Corbin et al. | |
| 8,927,697 B2 | 1/2015 | Davis et al. | |
| 2002/0004215 A1 | 1/2002 | Osbourn et al. | |
| 2002/0199213 A1 | 12/2002 | Tomizuka et al. | |
| 2003/0028071 A1 | 2/2003 | Handy et al. | |
| 2003/0031667 A1 | 2/2003 | Deo et al. | |
| 2003/0032995 A1 | 2/2003 | Handy et al. | |
| 2003/0044772 A1 | 3/2003 | Watkins et al. | |
| 2003/0092125 A1 | 5/2003 | Davis et al. | |
| 2003/0190317 A1 | 10/2003 | Baca et al. | |
| 2003/0194404 A1 | 10/2003 | Greenfeder et al. | |
| 2004/0132101 A1 | 7/2004 | Lazar et al. | |
| 2015/0132319 A1 * | 5/2015 | Van Snick | C07K 16/22 424/158.1 |
| 2015/0203579 A1 * | 7/2015 | Papadopoulos | A61K 39/3955 424/142.1 |

FOREIGN PATENT DOCUMENTS

| | | |
|---|---|---|
| WO | WO-87/05330 A1 | 9/1987 |
| WO | WO-88/07378 A1 | 10/1988 |
| WO | WO-91/00906 A1 | 1/1991 |
| WO | WO-91/17271 A1 | 11/1991 |
| WO | WO-92/01047 A1 | 1/1992 |
| WO | WO-92/09690 A2 | 6/1992 |
| WO | WO-92/15679 A1 | 9/1992 |
| WO | WO-92/18619 A1 | 10/1992 |
| WO | WO-92/20791 A1 | 11/1992 |
| WO | WO-93/01288 A1 | 1/1993 |
| WO | WO-93/11161 A1 | 6/1993 |
| WO | WO-94/02602 A1 | 2/1994 |
| WO | WO-96/11953 A1 | 4/1996 |
| WO | WO-96/27011 A1 | 9/1996 |
| WO | WO-96/30498 A1 | 10/1996 |
| WO | WO-96/33735 A1 | 10/1996 |
| WO | WO-96/34096 A1 | 10/1996 |
| WO | WO-98/24893 A2 | 6/1998 |
| WO | WO-99/10494 A2 | 3/1999 |

OTHER PUBLICATIONS

Amstutz et al., In vitro display technologies: novel developments and applications, Curr. Opin. Biotechnol., 12(4):400-5 (2001).

Aplin et al., Preparation, properties, and applications of carbohydrate conjugates of proteins and lipids, CRC Crit. Rev. Biochem., 10(4):259-306 (1981).

Ascierto et al., The role of BRAF V600 mutation in melanoma, J. Transl. Med., 10:85 (2012).

Balmain et al., Functional loss of tumour suppressor genes in multistage chemical carcinogenesis, Princess Takamatsu Symp., 22:97-108 (1991).

Barbas et al., Assembly of combinatorial antibody libraries on phage surfaces: the gene III site, Proc. Natl. Acad. Sci. USA, 88(18):7978-82 (1991).

Batra et al., Recombinant anti-erbB2 immunotoxins containing Pseudomonas exotoxin, Proc. Natl. Acad. Sci. USA, 89(13):5867-71 (1992).

Bayer et al., The avidin-biotin complex in affinity cytochemistry, Methods Enzymol., 62:308-15 (1979).

Better et al., *Escherichia coli* secretion of an active chimeric antibody fragment. Science. 240: 1041-3 (1988).

Better et al., Potent anti-CD5 ricin A chain immunoconjugates from bacterially produced Fab' and F(ab')2. Proc. Natl. Acad. Sci. USA. 90: 457-61 (1993).

Bird et al., Single-chain antigen-binding proteins, Science, 242(4877):423-6 (1988).

Border et al., Transforming growth factor beta in tissue fibrosis, N. Engl. J. Med., 331(19):1286-92 (1994).

Brennan et al., Preparation of bispecific antibodies by chemical recombination of monoclonal immunoglobulin G1 fragments, Science, 229(4708):81-3 (1985).

Brinkmann et al., B3(Fv)-PE38KDEL, a single-chain immunotoxin that causes complete regression of a human carcinoma in mice, Proc. Natl. Acad. Sci. USA, 88(19):8616-20 (1991).

Brown et al., Blockade of programmed death-1 ligands on dendritic cells enhances T cell activation and cytokine production, J. Immunol., 170(3):1257-66 (2003).

Bruggermann et al., Designer mice: the production of human antibody repertoires in transgenic animals, Year Immunol., 7:33-40 (1993).

Burns et al., Loss of heterozygosity and mutational alterations of the p53 gene in skin tumours of interspecific hybrid mice, Oncogene, 6(12):2363-9 (1991).

Burton et al., Human antibodies from combinatorial libraries, Adv. Immunol., 57:191-280 (1994).

Caravella et al., Design of next-generation protein therapeutics, Curr. Opin. Chem. Biol., 14(4):520-8 (2010).

Caron et al., Engineered humanized dimeric forms of IgG are more effective antibodies, J. Exp. Med., 176(4):1191-5 (1992).

Carter et al., High level *Escherichia coli* expression and production of a bivalent humanized antibody fragment. Bio/Technology 10: 163-7 (1992).

Chaudhary et al., A recombinant immunotoxin consisting of two antibody variable domains fused to Pseudomonas exotoxin, Nature, 339(6223):394-7 (1989).

Chothia et al., Canonical structures for the hypervariable regions of immunoglobulins, J. Mol. Biol., 196(4):901-17 (1987).

Chothia et al., Conformations of immunoglobulin hypervariable regions, Nature, 342(6252):877-83 (1989).

Clackson et al., Making antibody fragments using phage display libraries, Nature, 352(6336):624-8 (1991).

Cortez-Ramamozo et al., Efficient cancer therapy with a nanobody-based conjugate, Cancer Res., 64(8):2853-7 (2004).

Danielpour et al., Immunodetection and quantitation of the two forms of transforming growth factor-beta (TGF-beta 1 and TGF-beta 2) secreted by cells in culture, J. Cell Physiol., 138(1):79-86 (1989).

Danielpour et al., Sandwich enzyme-linked immunosorbent assays (SELISAs) quantitate and distinguish two forms of transforming growth factor-beta (TGF-beta 1 and TGF-beta 2) in complex biological fluids, Growth Factors, 2(1):61-71 (1989).

Darling et al., Kinetic exclusion assay technology: characterization of molecular interactions, Assay Drug Dev. Technol., 2(6):647-57 (2004).

De Martin et al., Complementary DNA for human glioblastoma-derived T cell suppressor factor, a novel member of the transforming growth factor-beta gene family, EMBO J., 6(12):3673-7 (1987).

Demetriou et al., Fetuin/alpha2-HS glycoprotein is a transforming growth factor-beta type II receptor mimic and cytokine antagonist, J. Biol. Chem., 271(22):12755-61 (1996).

Deonarain et al., Tumor Targeting, 1:177 (1995).

Derynck et al., Synthesis of messenger RNAs for transforming growth factors alpha and beta and the epidermal growth factor receptor by human tumors, Cancer Res., 47(3):707-12 (1987).

(56) References Cited

OTHER PUBLICATIONS

Desmyter et al., Antigen specificity and high affinity binding provided by one single loop of a camel single-domain antibody, J. Biol. Chem., 276(28):26285-90 (2001).
Dohlsten et al., Monoclonal antibody-superantigen fusion proteins: tumor-specific agents for T-cell-based tumor therapy, Proc. Natl. Acad. Sci. USA, 91(19):8945-9).
Doronina et al., Development of potent monoclonal antibody auristatin conjugates for cancer therapy, Nat. Biotechnol., 21(7):778-84 (2003).
Dunker et al., Targeted mutations of transforming growth factor-beta genes reveal important roles in mouse development and adult homeostasis, Eur. J. Biochem., 267(24):6982-8 (2000).
Edge et al., Deglycosylation of glycoproteins by trifluoromethanesulfonic acid, Anal. Biochem., 118(1):131-7 (1981).
Engvall et al., Enzyme-linked immunosorbent assay, Elisa. 3. Quantitation of specific antibodies by enzyme-labeled anti-immunoglobulin in antigen-coated tubes, J. Immunol., 109(1):129-35 (1972).
Ferrara et al., Modulation of therapeutic antibody effector functions by glycosylation engineering: influence of Golgi enzyme localization domain and co-expression of heterologous beta1, 4-N-acetylglucosaminyltransferase III and Golgi alpha-mannosidase II, Biotechnol. Bioeng., 93(5):851-61 (2006).
Fishwild et al., High-avidity human IgG kappa monoclonal antibodies from a novel strain of minilocus transgenic mice, Nat. Biotechnol., 14(7):845-51 (1996).
Fix, Strategies for delivery of peptides utilizing absorption-enhancing agents, J. Pharm. Sci., 85(12):1282-5 (1996).
Flavell et al., The polarization of immune cells in the tumour environment by TGFbeta, Nat. Rev. Immunol., 10(8):554-67 (2010).
Florini et al., Transforming growth factor-beta. A very potent inhibitor of myoblast differentiation, identical to the differentiation inhibitor secreted by Buffalo rat liver cells, J. Biol. Chem., 261(35):16509-13 (1986).
Fominaya et al., Target cell-specific DNA transfer mediated by a chimeric multidomain protein. Novel non-viral gene delivery system, J. Biol. Chem., 271(18)10560-8 (1996).
Frame et al., Epithelial carcinogenesis in the mouse: correlating the genetics and the biology, Philos. Trans. R Soc. Lond. B Biol. Sci., 353(1370):839-45 (1998).
Francisco et al., The PD-1 pathway in tolerance and autoimmunity, Immunol. Rev., 236:219-42 (2010).
Freeman et al., Engagement of the PD-1 immunoinhibitory receptor by a novel B7 family member leads to negative regulation of lymphocyte activation, J. Exp. Med., 192(7):1027-34 (2000).
Friedman et al., Antitumor activity of the single-chain immunotoxin BR96 sFv-PE40 against established breast and lung tumor xenografts, J. Immunol., 150(7):3054-61 (1991).
Fuchs et al., Targeting recombinant antibodies to the surface of *Escherichia coli*: fusion to a peptidoglycan associated lipoprotein, Bio/Technology, 9:1369-73 (Dec. 1991).
Garrard et al., Fab assembly and enrichment in a monovalent phage display system, Bio/Technology, 9(12):1373-7 (1991).
Goding, Conjugation of antibodies with fluorochromes: modifications to the standard methods, J. Immunol. Methods, 13(3-4):215-26 (1976).
Goldenberg, New developments in monoclonal antibodies for cancer detection and therapy, CA Cancer J. Clin., 44(1):43-64 (1994).
Graham et al., Characteristics of a human cell line transformed by DNA from human adenovirus type 5. J. Gen. Virol. 36: 59-74 (1977).
Gram et al., In vitro selection and affinity maturation of antibodies from a naive combinatorial immunoglobulin library, Proc. Natl. Acad. Sci. USA, 89(8):3576-80 (1992).
Green et al., Transgenic mouse strains as platforms for the successful discovery and development of human therapeutic monoclonal antibodies, Curr. Drug Discov. Technol., 11(1):74-84 (2014).
Greenberg et al., A new antigen receptor gene family that undergoes rearrangement and extensive somatic diversification in sharks, Nature, 374(6518):168-73 (1995).
Griffiths et al., Human anti-self antibodies with high specificity from phage display libraries, EMBO J., 12(2):725-34 (1993).
Gruber et al., Efficient tumor cell lysis mediated by a bispecific single chain antibody expressed in *Escherichia coli*, J. Immunol., 152(11):5368-74 (1994).
Guss et al., Structure of the IgG-binding regions of streptococcal protein G.*EMBO* 5: 1567-75 (1986).
Hakimuddin et al., A chemical method for the deglycosylation of proteins, Arch. Biochem. Biophys., 259:52-7 (1987).
Hamers-Casterman et al., Naturally occurring antibodies devoid of light chains, Nature, 363(6428):446-8 (1993).
Hanes et al., In vitro selection and evolution of functional proteins by using ribosome display, Proc. Natl. Acad. Sci. USA, 94(10):4937-42 (1997).
Hay et al., Bacteriophage cloning and *Escherichia coli* expression of a human IgM Fab, Hum. Antibodies Hybridomas, 3(2):81-5 (1992).
Hinman et al., Preparation and characterization of monoclonal antibody conjugates of the calicheamicins: a novel and potent family of antitumor antibiotics, Cancer Res., 53(14):3336-42 (1993).
Holley et al., Purification of kidney epithelial cell growth inhibitors, Proc. Natl. Acad. Sci. USA, 77(10):5989-92 (1980).
Holliger et al., "Diabodies": small bivalent and bispecific antibody fragments, Proc. Natl. Acad. Sci. USA, 90(14):6444-8 (1993).
Holliger et al., Engineered antibody fragments and the rise of single domains, Nat. Biotechnol., 23(9):1126-36 (2005).
Hoogenboom et al., By-passing immunisation. Human antibodies from synthetic repertoires of germline VH gene segments rearranged in vitro, J. Mol. Biol., 227(2):381-8 (1992).
Hoogenboom et al., Multi-subunit proteins on the surface of filamentous phage: methodologies for displaying antibody (Fab) heavy and light chains, Nucleic Acids Res., 19(15):413-7 (1991).
Huang et al., Modeling cutaneous squamous carcinoma development in the mouse, Cold Spring Harb. Perspect. Med., 4(9):a013623 (2014).
Huse et al., Generation of a large combinatorial library of the immunoglobulin repertoire in phage lambda, Science, 246-1275-81 (1989).
Huston et al., Protein engineering of antibody binding sites: recovery of specific activity in an anti-digoxin single-chain FV analogue produced in *Escherichia coli*, Proc. Natl. Acad. Sci. USA, 85(16):5879-83 (1988).
International Search Report and Written Opinion, International Application No. PCT/US2016/025802, dated Oct. 19, 2016.
Ishida et al., Induced expression of PD-1, a novel member of the immunoglobulin gene superfamily, upon programmed cell death, EMBO J., 11(11):3887-95 (1992).
Ishida et al., Production of human monoclonal and polyclonal antibodies in TransChromo animals, Cloning Stem Cells, 4(1):91-102 (2002).
Jakobovits et al., Analysis of homozygous mutant chimeric mice: deletion of the immunoglobulin heavy-chain joining region blocks B-cell development and antibody production, Proc. Natl. Acad. Sci. USA, 90(6):2551-5 (1993).
Jespers et al., Guiding the selection of human antibodies from phage display repertoires to a single epitope of an antigen, Bio/Technology, 12(9):899-903 (1994).
Jones et al., Replacing the complementarity-determining regions in a human antibody with those from a mouse, Nature, 321(6069):522-5 (1986).
Kabat et al., Sequences of Proteins of Immunological Interests, National Institutes of Health, Bethesda, Md., (1987 and 1991).
Kettleborough et al., Humanization of a mouse monoclonal antibody by CDR-grafting: the importance of framework residues on loop conformation, Protein Eng., 4(7):773-83 (1991).
Kohler et al., Continuous cultures of fused cells secreting antibody of predefined specificity, Nature, 256(5517):495-7 (1975).
Kostelny et al., Formation of a bispecific antibody by the use of leucine zippers, J. Immunol., 148(5):1547-53 (1992).
Kreitman et al., Cytotoxic activities of recombinant immunotoxins composed of Pseudomonas toxin or diphtheria toxin toward lymphocytes from patients with adult T-cell leukemia, Leukemia, 7(4):553-62 (1993).

(56) References Cited

OTHER PUBLICATIONS

Kuan et al., Recombinant immunotoxin containing a disulfide-stabilized Fv directed at erbB2 that does not require proteolytic activation, Biochemistry, 35(9):2872-7 (1996).
Kuppner et al., The glioblastoma-derived T-cell suppressor factor/transforming growth factor beta 2 inhibits the generation of lymphokine-activated killer (LAK) cells, Int. J. Cancer, 42(4):562-7 (1988).
Latchman et al., PD-L2 is a second ligand for PD-1 and inhibits T cell activation, Nat. Immunol., 2(3):261-8 (2001).
Lee et al., Complete humanization of the mouse immunoglobulin loci enables efficient therapeutic antibody discovery, Nat. Biotechnol., 32(4):356-63 (2014).
Lee et al., Microbial cell-surface display, Trends Biotechnol., 21(1):45-52 (2003).
Lee et al., The application of transgenic mice for therapeutic antibody discovery, Methods Mol. Biol., 901:137-48 (2012).
Lefranc et al., IMGT unique numbering for immunoglobulin and T cell receptor variable domains and Ig superfamily V-like domains, Dev. Comp. Immunol., 27(1):55-77 (2003).
Lefranc, The IMGT unique numbering for immunoglobulins, T-cell receptors, and Ig-like domains, Immunologist 7(4):132-6 (1999).
Li et al., Cancer-expanded myeloid-derived suppressor cells induce anergy of NK cells through membrane-bound TGF-beta 1, J. Immunol., 182(1):240-9 (2009).
Linardou et al., Deoxyribonuclease I (DNAse I). A novel approach for targeted cancer therapy, Cell Biophys., 25:243-8 (1994).
Lindmark et al., Binding of immunoglobulins to protein A and immunoglobulin levels in mammalian sera. *J. Immunol. Meth.* 62: 1-13 (1983).
Liu et al., Eradication of large colon tumor xenografts by targeted delivery of maytansinoids, Proc. Natl. Acad. Sci. USA, 93(16):8618-23 (1996).
Lode et al., Targeted therapy with a novel enediyene antibiotic calicheamicin $\Theta^1{}_1$ effectively suppresses growth and dissemination of liver metastases in a syngeneic model of murine neuroblastoma, Cancer Res., 58:2925-8 (1998).
Lutjen-Drecoll, Morphological changes in glaucomatous eyes and the role of TGFbeta2 for the pathogenesis of the disease, Exp. Eye Res., 81(1):1-4 (2005).
Mandler et al., Immunoconjugates of geldanamycin and anti-HER2 monoclonal antibodies: antiproliferative activity on human breast carcinoma cell lines, J. Natl. Cancer Inst., 92(19):1573-81 (2000).
Mandler et al., Synthesis and evaluation of antiproliferative activity of a geldanamycin-Herceptin immunoconjugate, Bioorg. Med. Chem. Lett., 10(10):1025-8 (2000).
Marks et al., By-passing immunization. Human antibodies from V-gene libraries displayed on phage, J. Mol. Biol., 222(3):581-97 (1991).
Massey, Catalytic antibodies catching on. *Nature*, 328: 457-8 (1987).
Mather et al., Culture of testicular cells in hormone-supplemented serum-free medium. *Annals N.Y. Acad. Sci.* 383: 44-68 (1982).
Mather, Establishment and characterization of two distinct mouse testicular epithelial cell lines. *Biol. Reprod.* 23: 243-251 (1980).
McCafferty et al., Phage antibodies: filamentous phage displaying antibody variable domains, Nature, 348(6301):552-4 (1990).
Morrison et al., Chimeric human antibody molecules: mouse antigen-binding domains with human constant region domains, Proc. Natl. Acad. Sci. USA, 81(21):6851-5 (1984).
Morrison et al., Genetically engineered antibody molecules, Adv. Immunol., 44:65-92 (1989).
Nagaraj et al., Targeting the transforming growth factor-beta signaling pathway in human cancer, Expert Opin. Investig. Drugs, 19(1):77-91 (2010).
Neri et al., High-affinity antigen binding by chelating recombinant antibodies (CRAbs), J. Mol. Biol., 246(3):367-73 (1995).
Neuberger et al., Recombinant antibodies possessing novel effector functions. *Nature*, 312: 604-8 (1984).
Nicholls et al., Characterization of single-chain antibody (sFv)-toxin fusion proteins produced in vitro in rabbit reticulocyte lysate, J. Biol. Chem., 268(7):5302-8 (1993).
Nuttall et al., Isolation of the new antigen receptor from wobbegong sharks, and use as a scaffold for the display of protein loop libraries, Mol. Immunol., 38(4):313-26 (2001).
Oliyai et al., Prodrugs of peptides and proteins for improved formulation and delivery, Annu. Rev. Pharmacol. Toxicol., 33:521-44 (1993).
Padlan, A possible procedure for reducing the immunogenicity of antibody variable domains while preserving their ligand-binding properties, Mol. Immunol., 28(4-5):489-98 (1991).
Padlan, Anatomy of the antibody molecule, Mol. Immunol., 31(3):169-217 (1994).
Pastan et al., Immunotoxins. *Cell*, 47: 641-8 (1986).
Philips et al., Therapeutic uses of anti-PD-1 and anti-PD-L1 antibodies, Int. Immunol., 27(1):39-46 (2015).
Pohlers et al., TGF-beta and fibrosis in different organs—molecular pathway imprints, Biochim. Biophys. Acta, 1792(8):746-56 (2009).
Poljak, Production and structure of diabodies, Structure, 2(12):1121-3 (1994).
Quintanilla et al., Carcinogen-specific mutation and amplification of Ha-ras during mouse skin carcinogenesis, Nature, 322(6074):78-80 (1986).
Reichman et al., Single domain antibodies: comparison of camel VH and camelised human VH domains, J. Immunol. Methods, 231:25-38 (1999).
Riechmann et al., Reshaping human antibodies for therapy, Nature, 332(6162):323-7 (1988).
Roberts et al., New class of transforming growth factors potentiated by epidermal growth factor: isolation from non-neoplastic tissues, Proc. Natl. Acad. Sci. USA, 78(9):5339-43 (1981).
Roberts et al., Transforming growth factor-beta: possible roles in carcinogenesis, Br. J. Cancer, 57(6):594-600 (1988).
Sanger et al., DNA sequencing with chain-terminating inhibitors, Proc. Natl. Acad. Sci. USA, 74(12):5463-7 (1977).
Sarmay et al., Mapping and comparison of the interaction sites on the Fc region of IgG responsible for triggering antibody dependent cellular cytotoxicity (ADCC) through different types of human Fc gamma receptor, Mol. Immunol., 29(5):633-9 (1992).
Scatchard, The attractions of proteins for small molecules and ions, Ann. NY Acad. Sci., 51:660-72 (1949).
Schmidt et al., A bivalent single-chain antibody-toxin specific for ErbB-2 and the EGF receptor, Int. J. Cancer, 65(4):538-46 (1996).
Sergeeva et al., Display technologies: application for the discovery of drug and gene delivery agents, Adv. Drug Deliv. Rev., 58(15):1622-54 (2006).
Seyedin et al., Purification and characterization of two cartilage-inducing factors from bovine demineralized bone, Proc. Natl. Acad. Sci. USA, 82(8):2267-71 (1985).
Shalaby et al., Development of humanized bispecific antibodies reactive with cytotoxic lymphocytes and tumor cells overexpressing the HER2 protooncogene, J. Exp. Med., 175(1):217-25 (1992).
Shields et al., Lack of fucose on human IgG1 N-linked oligosaccharide improves binding to human Fcgamma RIII and antibody-dependent cellular toxicity, J. Biol. Chem., 277(30):26733-40 (2002).
Shih et al., A fluorouridine-anti-CEA immunoconjugate is therapeutically effective in a human colonic cancer xenograft model, Int. J. Cancer, 46(6):1101-6 (1990).
Shih et al., Site-specific linkage of methotrexate to monoclonal antibodies using an intermediate carrier, Int. J. Cancer, 41(6):832-9 (1988).
Shinkawa et al., The absence of fucose but not the presence of galactose or bisecting N-acetylglucosamine of human IgG1 complex-type oligosaccharides shows the critical role of enhancing antibody-dependent cellular cytotoxicity, J. Biol. Chem., 278(5):3466-73 (2003).
Shinohara et al., Structure and chromosomal localization of the human PD-1 gene (PDCD1), Genomics, 23(3):704-6 (1994).
Shopes et al., A genetically engineered human IgG mutant with enhanced cytolytic activity, J. Immunol., 148(9):2918-22 (1992).
Singh et al., Successful shape-based virtual screening: the discovery of a potent inhibitor of the type I TGFbeta receptor kinase (TbetaRI), Bioorg. Med. Chem. Lett., 13(24):4355-9 (2003).

(56) References Cited

OTHER PUBLICATIONS

Spasevska, An outlook on bispecific antibodies: Methods of production and therapeutic benefits, BioSciences Master Reviews, 7 pp. (Jan. 2014).
Sporn et al., Transforming growth factor-beta: recent progress and new challenges, J. Cell Biol., 119(5):1017-21 (1992).
Sternberger et al., The unlabeled antibody enzyme method of immunohistochemistry: preparation and properties of soluble antigen-antibody complex (horseradish peroxidase-antihorseradish peroxidase) and its use in identification of spirochetes, J. Histochem. Cytochem., 18(5):315-33 (1970).
Stevenson et al., A chimeric antibody with dual Fc regions (bisFabFc) prepared by manipulations at the IgG hinge, Anticancer Drug Des., 3(4):219-30 (1989).
Studnicka et al., Human-engineered monoclonal antibodies retain full specific binding activity by preserving non-CDR complementarity-modulating residues, Protein Eng., 7(6):805-14 (1994).
Thompson et al., An anti-CD3 single-chain immunotoxin with a truncated diphtheria toxin avoids inhibition by pre-existing antibodies in human blood, J. Biol. Chem., 270(47):28037-41 (1995).
Thotakura et al., Enzymatic deglycosylation of glycoproteins, Methods Enzymol., 138:350-9 (1987).
Tutt et al., Trispecific F(ab')3 derivatives that use cooperative signaling via the TCR/CD3 complex and CD2 to activate and redirect resting cytotoxic T cells, J. Immunol., 147(1):60-9 (1991).
Umana et al., Engineered glycoforms of an antineuroblastoma IgG1 with optimized antibody-dependent cellular cytotoxic activity, Nat. Biotechnol., 17(2):176-80 (1999).
Urlaub et al., Isolation of Chinese hamster cell mutants deficient in dihydrofolate reductase activity. *Proc. Natl. Acad. Sci. USA*. 77: 4216-20 (1980).
Vallera et al., Anti-graft-versus-host disease effect of DT390-anti-CD3sFv, a single-chain Fv fusion immunotoxin specifically targeting the CD3 epsilon moiety of the T-cell receptor, Blood, 88(6):2342-53 (1996).
Van Assche et al., Medical therapy for Crohn's disease strictures, Inflamm. Bowel. Dis., 10(1):55-60 (2004).
Wang et al., Abstacts of the 209th ACS National Meeting, Anaheim, Calif., Apr. 2-6, 1995, Part 1, BIOT005.
Wang et al., In vitro characterization of the anti-PD-1 antibody nivolumab, BMS-936558, and in vivo toxicology in non-human primates, Cancer Immunol. Res., 2(9):846-56 (2014).
Ward et al., Binding activities of a repertoire of single immunoglobulin variable domains secreted from *Escherichia coli*, Nature, 341(6242):544-6 (1989).
Watkins, Screening of phage-expressed antibody libraries by capture lift, Methods Mol. Biol., 178:187-93 (2002).
Wei et al., Tumor-induced immune suppression of in vivo effector T-cell priming is mediated by the B7-H1/PD-1 axis and transforming growth factor beta, Cancer Res., 68(13):5432-8 (2008).
Wels et al., EGF receptor and p185erbB-2-specific single-chain antibody toxins differ in their cell-killing activity on tumor cells expressing both receptor proteins, Int. J. Cancer, 60(1):137-44 (1995).
Winter et al., Making antibodies by phage display technology, Annu. Rev. Immunol., 12:433-55 (1994).
Wittrup, Protein engineering by cell-surface display, Curr. Opin. Biotechnol., 12(4):395-9 (2001).
Wolff et al., Monoclonal antibody homodimers: enhanced antitumor activity in nude mice, Cancer Res., 53(11):2560-5 (1993).
Wong et al., Blockade of programmed death-1 in young (New Zealand Black x New Zealand White)F1 mice promotes the suppressive capacity of CD4+ regulatory T cells protecting from lupus-like disease, J. Immunol., 190(11):5402-11 (2013).
Wrana et al., TGF beta signals through a heteromeric protein kinase receptor complex, Cell, 71(6):1003-14 (1992).
Wrann et al., T cell suppressor factor from human glioblastoma cells is a 12.5-kd protein closely related to transforming growth factor-beta, EMBO J., 6(6):1633-6 (1987).
Xiang et al., Induction of myeloid-derived suppressor cells by tumor exosomes, Int. J. Cancer, 124(11):2621-33 (2009).
Yamane-Ohnuki et al., Establishment of FUT8 knockout Chinese hamster ovary cells: an ideal host cell line for producing completely defucosylated antibodies with enhanced antibody-dependent cellular cytotoxicity, Biotechnol. Bioeng., 87(5):614-22 (2004).
Yang et al., TGF-beta and immune cells: an important regulatory axis in the tumor microenvironment and progression, Trends Immunol., 31(6):220-7 (2010).
Yu et al., Peptide-antibody conjugates for tumour therapy: a MHC-class-II-restricted tetanus toxin peptide coupled to an anti-Ig light chain antibody can induce cytotoxic lysis of a human B-cell lymphoma by specific CD4 T cells, Int. J. Cancer, 56(2):244-8 (1994).
Yuspa et al., Multistage carcinogenesis in the skin, J. Investig. Dermatol. Symp. Proc., 1(2):147-50 (1996).
Zapata et al., Engineering linear F(ab')2 fragments for efficient production in *Escherichia coli* and enhanced antiproliferative activity, Protein Eng., 8(10):1057-62 (1995).
International Preliminary Report on Patentability, International application No. PCT/US2016/025802, dated Oct. 3, 2017.

\* cited by examiner

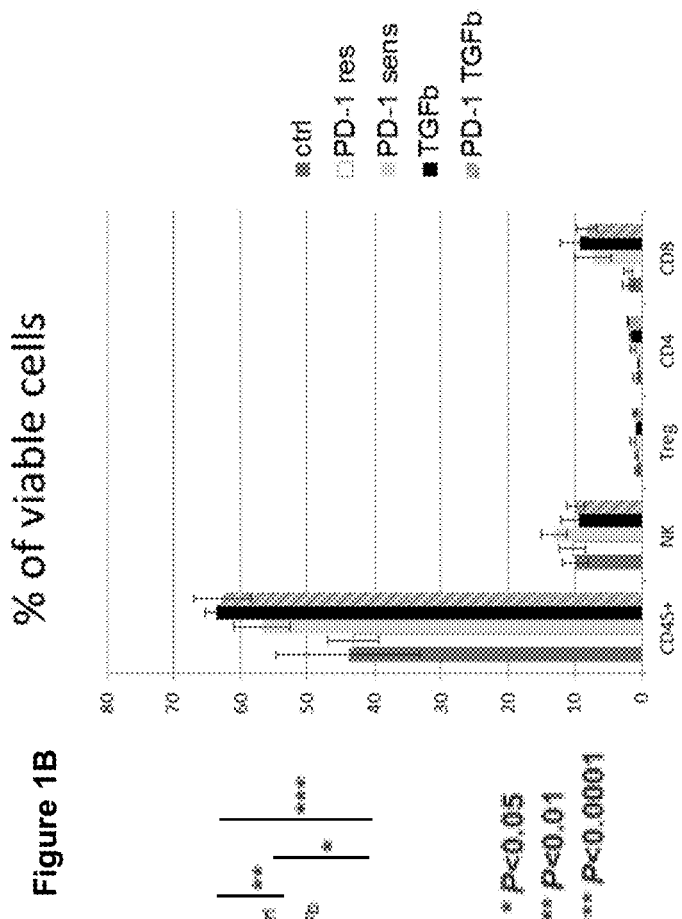
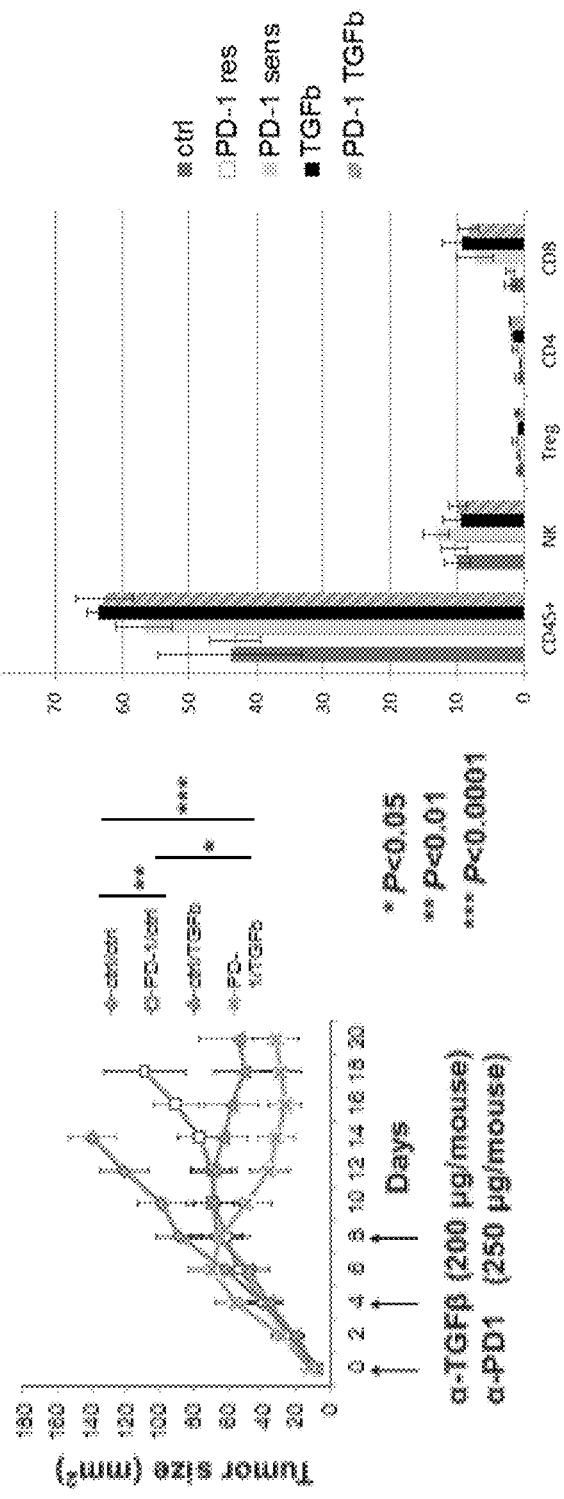
Figure 1A
Figure 1B

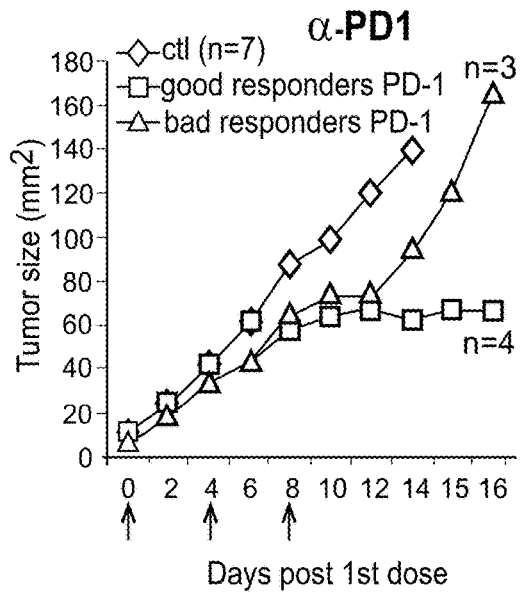
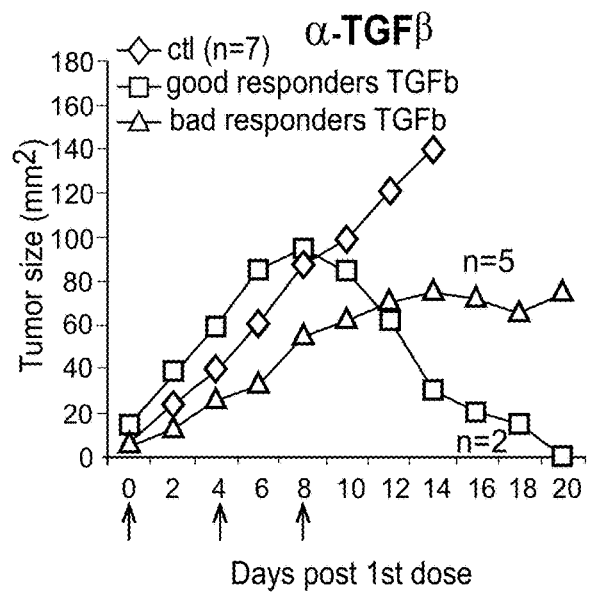
FIG. 2A
FIG. 2B
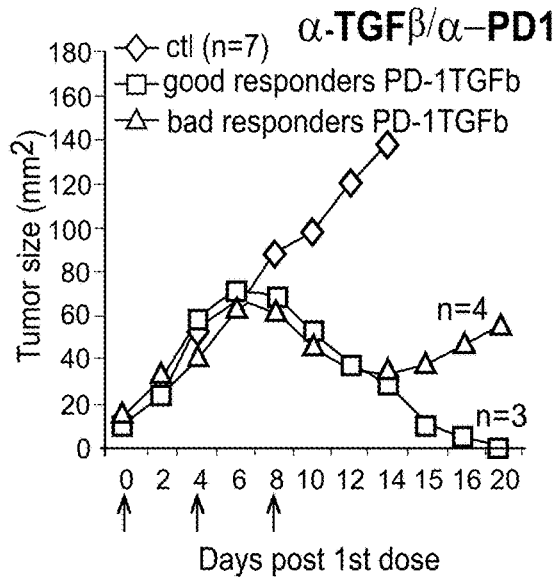
FIG. 2C

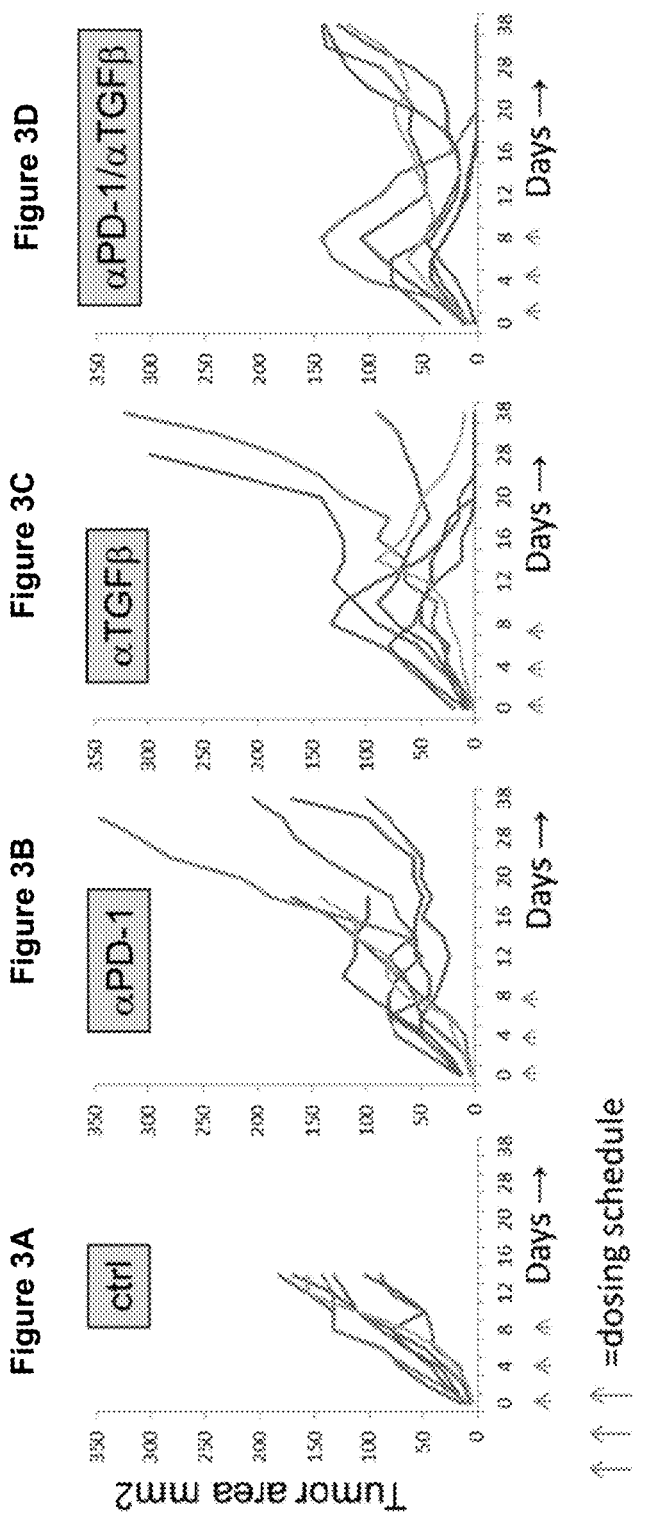

SEQUENCE LISTING

<160> NUMBER OF SEQ ID NOS: 30

<210> SEQ ID NO 1
<211> LENGTH: 366
<212> TYPE: DNA
<213> ORGANISM: Artificial Sequence
<220> FEATURE:
<223> OTHER INFORMATION: Synthetic nucleotide
<220> FEATURE:
<221> NAME/KEY: misc_feature
<223> OTHER INFORMATION: Clone XPA.42.068 heavy chain

<400> SEQUENCE: 1
caggttcagc tggtgcagtc tggggctgag gtgaagaagc ctggggcctc agtgaaggtc    60
tcctgcaagg cttctggata caccttcacc ggctactata tgcactgggt gcgacaggcc   120
cctggacaag gcttgagtg gatgggatgg atcaaccta acactggtgg cacaaactat   180
gcacagaagt ttcagggcag ggtcaccatg accagggaca cgtccatcag cacagcctac   240
atggagctga gcaggctgag atctgacgac acggccgttt attactgtgc gagatcattc   300
ctgtggctgg ttccctctga tgcttttgat atctggggcc aagggacaat ggtcaccgtc   360
tcttca                                                              366

<210> SEQ ID NO 2
<211> LENGTH: 122
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42.068 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(111)
<223> OTHER INFORMATION: H-CDR3

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Thr Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Phe Leu Trp Leu Val Pro Ser Asp Ala Phe Asp Ile Trp
            100                 105                 110

Gly Gln Gly Thr Met Val Thr Val Ser Ser
        115                 120

<210> SEQ ID NO 3
<211> LENGTH: 327
<212> TYPE: DNA
<213> ORGANISM: Artificial Sequence
<220> FEATURE:
<223> OTHER INFORMATION: Synthetic nucleotide
<220> FEATURE:
<221> NAME/KEY: misc_feature
<223> OTHER INFORMATION: Clone XPA.42.068 light chain -continued

<400> SEQUENCE: 3

```
tcttctgagc tgactcagcc accctcagtg tccgtggccc caggagagaa ggccaggatt      60
acctgtgggg gaataacat tggacgtaaa agtgtacatt ggtaccagca gaggccaggc      120
caggcccctg ttgtggtcct ctactatgat agagtcagac cctcagggat ccctgagcga      180
ttttctggct ccaactctgg gaacacggcc accctgacca tcaccagggt cgaagccggg      240
gatgaggccg actattttg tcaggtgtgg gataacacta gtgagcatgt ggtcttcggc      300
ggaggcaccc agctgaccgt cctaggc                                         327
```

<210> SEQ ID NO 4
<211> LENGTH: 109
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42.068 light chain
<220> FEATURE:
<221> NAME/KEY: MISC_FEATURE
<222> LOCATION: (26)..(31)
<223> OTHER INFORMATION: L-CDR1
<220> FEATURE:
<221> NAME/KEY: MISC_FEATURE
<222> LOCATION: (49)..(51)
<223> OTHER INFORMATION: L-CDR2
<220> FEATURE:
<221> NAME/KEY: MISC_FEATURE
<222> LOCATION: (88)..(97)
<223> OTHER INFORMATION: L-CDR3

<400> SEQUENCE: 4

```
Ser Ser Glu Leu Thr Gln Pro Pro Ser Val Ser Val Ala Pro Gly Glu
1               5                   10                  15

Lys Ala Arg Ile Thr Cys Gly Gly Asn Asn Ile Gly Arg Lys Ser Val
            20                  25                  30

His Trp Tyr Gln Gln Arg Pro Gly Gln Ala Pro Val Val Val Leu Tyr
        35                  40                  45

Tyr Asp Arg Val Arg Pro Ser Gly Ile Pro Glu Arg Phe Ser Gly Ser
    50                  55                  60

Asn Ser Gly Asn Thr Ala Thr Leu Thr Ile Thr Arg Val Glu Ala Gly
65                  70                  75                  80

Asp Glu Ala Asp Tyr Phe Cys Gln Val Trp Asp Asn Thr Ser Glu His
                85                  90                  95

Val Val Phe Gly Gly Gly Thr Gln Leu Thr Val Leu Gly
            100                 105
```

<210> SEQ ID NO 5
<211> LENGTH: 363
<212> TYPE: DNA
<213> ORGANISM: Artificial Sequence
<220> FEATURE:
<223> OTHER INFORMATION: Synthetic nucleotide
<220> FEATURE:
<221> NAME/KEY: misc_feature
<223> OTHER INFORMATION: Clone XPA.42.089 heavy chain

<400> SEQUENCE: 5

```
caggtgcagc tggtacagtc tggggctgag gtgaagaagc ctgggtcctc ggtgaaggtc      60
tcctgcaagg cttctggagg caccttcagc agctatgcta tcagctgggt gcgacaggcc      120
cctggacaag gcttgagtg gatgggaggg atcatcccta tctttggtac agcaaactac      180
```

```
gcacagaagt tccagggcag agtcacgatt accgcggacg aatccacgag cacagcctac    240
atggagctga gcagcctgag atctgaggac acggccgtgt attactgtgc gaggggacta    300
tgggaggttc gggcccttcc gtcggtctac tggggccagg gaaccctggt caccgtctcc    360
tca                                                                  363
```

```
<210> SEQ ID NO 6
<211> LENGTH: 121
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42.089 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(110)
<223> OTHER INFORMATION: H-CDR3

<400> SEQUENCE: 6
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Trp Glu Val Arg Ala Leu Pro Ser Val Tyr Trp Gly
            100                 105                 110

Gln Gly Thr Leu Val Thr Val Ser Ser
        115                 120

```
<210> SEQ ID NO 7
<211> LENGTH: 327
<212> TYPE: DNA
<213> ORGANISM: Artificial Sequence
<220> FEATURE:
<223> OTHER INFORMATION: Synthetic nucleotide
<220> FEATURE:
<221> NAME/KEY: misc_feature
<223> OTHER INFORMATION: Clone XPA.42.089 light chain

<400> SEQUENCE: 7
```

```
tcctatgagc tgacacagcc accctcagtg tccgtggccc cgggacagac ggccagaatt    60
acctgtgggg caaatgacat tggaagtaaa agtgtccact ggtaccagca gaaggcaggc    120
caggcccctg tactggtcgt ctctgaagat atcatccggc cctcaggat  ccctgagcga    180 atctctggct ccaactctgg gaacacggcc accctgacca tcagcagggt cgaagccggg    240
```

```
gatgaggccg actattactg tcaagtttgg datagggata gtgatcaata tgtctttgga      300
actgggacca aggtcaccgt cctaggc                                         327
```

<210> SEQ ID NO 8
<211> LENGTH: 109
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42.089 light chain
<220> FEATURE:
<221> NAME/KEY: MISC_FEATURE
<222> LOCATION: (26)..(31)
<223> OTHER INFORMATION: L-CDR1
<220> FEATURE:
<221> NAME/KEY: MISC_FEATURE
<222> LOCATION: (49)..(51)
<223> OTHER INFORMATION: L-CDR2
<220> FEATURE:
<221> NAME/KEY: MISC_FEATURE
<222> LOCATION: (88)..(97)
<223> OTHER INFORMATION: L-CDR3

<400> SEQUENCE: 8

Ser Tyr Glu Leu Thr Gln Pro Pro Ser Val Ser Val Ala Pro Gly Gln
1               5                   10                  15

Thr Ala Arg Ile Thr Cys Gly Ala Asn Asp Ile Gly Ser Lys Ser Val
            20                  25                  30

His Trp Tyr Gln Gln Lys Ala Gly Gln Ala Pro Val Leu Val Val Ser
        35                  40                  45

Glu Asp Ile Ile Arg Pro Ser Gly Ile Pro Glu Arg Ile Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Arg Asp Ser Asp Gln
                85                  90                  95

Tyr Val Phe Gly Thr Gly Thr Lys Val Thr Val Leu Gly
            100                 105

<210> SEQ ID NO 9
<211> LENGTH: 366
<212> TYPE: DNA
<213> ORGANISM: Artificial Sequence
<220> FEATURE:
<223> OTHER INFORMATION: Synthetic nucleotide
<220> FEATURE:
<221> NAME/KEY: misc_feature
<223> OTHER INFORMATION: Clone XPA.42.681 heavy chain

<400> SEQUENCE: 9

```
caggttcagc tggtgcagtc tggggctgag gtgaagaagc ctggggcctc agtgaaggtc      60
tcctgcaagg cttctggata caccttcacc ggctactata tgcactgggt gcgacaggcc     120
cctggacaag gcttgagtg gatgggatgg atcaacccta acactggtgg cacaaactat      180
gcacagaagt tcagggcag ggtcaccatg accaggaca cgtccatcag cacagcctac      240
atggagctga gcaggctgag atctgacgac acggccgttt attactgtgc gagatcattc     300
ctgtggctgg ttccctctga tgcttttgat atctggggcc aagggacaat ggtcaccgtc     360
tcttca                                                                366
```

<210> SEQ ID NO 10

<211> LENGTH: 122
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42.681 heavy chain
<220> FEATURE:
<221> NAME/KEY: MISC_FEATURE
<222> LOCATION: (26)..(33)
<223> OTHER INFORMATION: H-CDR1
<220> FEATURE:
<221> NAME/KEY: MISC_FEATURE
<222> LOCATION: (51)..(58)
<223> OTHER INFORMATION: H-CDR2
<220> FEATURE:
<221> NAME/KEY: MISC_FEATURE
<222> LOCATION: (97)..(111)
<223> OTHER INFORMATION: H-CDR3

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Thr Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Phe Leu Trp Leu Val Pro Ser Asp Ala Phe Asp Ile Trp
            100                 105                 110

Gly Gln Gly Thr Met Val Thr Val Ser Ser
        115                 120

<210> SEQ ID NO 11
<211> LENGTH: 327
<212> TYPE: DNA
<213> ORGANISM: Artificial Sequence
<220> FEATURE:
<223> OTHER INFORMATION: Synthetic nucleotide
<220> FEATURE:
<221> NAME/KEY: misc_feature
<223> OTHER INFORMATION: Clone XPA.42.681 light chain

<400> SEQUENCE: 11
tcctatgtgc tgactcagcc accctcagtg tccgtggccc caggaaagac ggccaggatt      60
acctgtgggg gaaacaacat tggatttaga agtgtgcact ggtaccaaca gaagtcaggc     120 caggccctg tcctggtcat ctattttgat cgcgcccggc cctcagggat ccctgagcga      180
ttctctgcct ccaactctga gaacacggcc acctgaccat caggagggt cgaagccggg      240 gatgaggccg actattactg tcaggtgtgg gatagtgaca gtgatgatct agtcttcggc     300
ggaggcaccc agctgaccgt cctaggt                                         327

<210> SEQ ID NO 12
<211> LENGTH: 109
<212> TYPE: PRT
<213> ORGANISM: Artificial Sequence
<220> FEATURE:
<223> OTHER INFORMATION: Synthetic peptide

```
<220> FEATURE:
<221> NAME/KEY: MISC_FEATURE
<223> OTHER INFORMATION: Clone XPA.42.681 light chain
<220> FEATURE:
<221> NAME/KEY: MISC_FEATURE
<222> LOCATION: (26)..(31)
<223> OTHER INFORMATION: L-CDR1
<220> FEATURE:
<221> NAME/KEY: MISC_FEATURE
<222> LOCATION: (49)..(51)
<223> OTHER INFORMATION: L-CDR2
<220> FEATURE:
<221> NAME/KEY: MISC_FEATURE
<222> LOCATION: (88)..(98)
<223> OTHER INFORMATION: L-CDR3

<400> SEQUENCE: 12

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Phe Arg Ser Val
            20                  25                  30

His Trp Tyr Gln Gln Lys Ser Gly Gln Ala Pro Val Leu Val Ile Tyr
        35                  40                  45

Phe Asp Arg Ala Arg Pro Ser Gly Ile Pro Glu Arg Phe Ser Ala Ser
50                  55                  60

Asn Ser Glu Asn Thr Ala Thr Leu Thr Ile Arg Arg Val Glu Ala Gly
65                  70                  75                  80

Asp Glu Ala Asp Tyr Tyr Cys Gln Val Trp Asp Ser Asp Ser Asp Asp
                85                  90                  95

Leu Val Phe Gly Gly Gly Thr Gln Leu Thr Val Leu Gly
            100                 105

<210> SEQ ID NO 13
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42.068 - H-CDR1

<400> SEQUENCE: 13

Gly Tyr Thr Phe Thr Gly Tyr Tyr
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42.068 - H-CDR2

<400> SEQUENCE: 14

Ile Asn Pro Asn Thr Gly Gly Thr
1               5

<210> SEQ ID NO 15
<211> LENGTH: 15
<212> TYPE: PRT
<213> ORGANISM: Artificial Sequence
<220> FEATURE:
<223> OTHER INFORMATION: Synthetic peptide
<220> FEATURE:
```

<221> NAME/KEY: MISC_FEATURE
<223> OTHER INFORMATION: Clone XPA.42.068 - H-CDR3

<400> SEQUENCE: 15

Ala Arg Ser Phe Leu Trp Leu Val Pro Ser Asp Ala Phe Asp Ile
1               5                   10                  15

<210> SEQ ID NO 16
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42.068 - L-CDR1

<400> SEQUENCE: 16

Asn Ile Gly Arg Lys Ser
1               5

<210> SEQ ID NO 17
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42.068 - L-CDR2

<400> SEQUENCE: 17

Tyr Asp Arg
1

<210> SEQ ID NO 18
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42.068 - L-CDR3

<400> SEQUENCE: 18

Gln Val Trp Asp Asn Thr Ser Glu His Val
1               5                   10

<210> SEQ ID NO 19
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42.089 - H-CDR1

<400> SEQUENCE: 19

Gly Gly Thr Phe Ser Ser Tyr Ala
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic peptide

```
<220> FEATURE:
<221> NAME/KEY: MISC_FEATURE
<223> OTHER INFORMATION: Clone XPA.42.089 - H-CDR2

<400> SEQUENCE: 20

Ile Ile Pro Ile Phe Gly Thr Ala
1               5

<210> SEQ ID NO 21
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42.089 - H-CDR3

<400> SEQUENCE: 21

Ala Arg Gly Leu Trp Glu Val Arg Ala Leu Pro Ser Val Tyr
1               5                   10

<210> SEQ ID NO 22
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42.089 - L-CDR1

<400> SEQUENCE: 22

Asp Ile Gly Ser Lys Ser
1               5

<210> SEQ ID NO 23
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42.089 - L-CDR2

<400> SEQUENCE: 23

Glu Asp Ile
1

<210> SEQ ID NO 24
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42.089 - L-CDR3

<400> SEQUENCE: 24

Gln Val Trp Asp Arg Asp Ser Asp Gln Tyr
1               5                   10

<210> SEQ ID NO 25
<211> LENGTH: 8
<212> TYPE: PRT
<213> ORGANISM: Artificial Sequence
<220> FEATURE:
```

<223> OTHER INFORMATION: Synthetic peptide
<220> FEATURE:
<221> NAME/KEY: MISC_FEATURE
<223> OTHER INFORMATION: Clone XPA.42-681 - H-CDR1

<400> SEQUENCE: 25

Gly Tyr Thr Phe Thr Gly Tyr Tyr
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42-681 - H-CDR2

<400> SEQUENCE: 26

Ile Asn Pro Asn Thr Gly Gly Thr
1               5

<210> SEQ ID NO 27
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42-681 - H-CDR3

<400> SEQUENCE: 27

Ala Arg Ser Phe Leu Trp Leu Val Pro Ser Asp Ala Phe Asp Ile
1               5                   10                  15

<210> SEQ ID NO 28
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42-681 - L-CDR1

<400> SEQUENCE: 28

Asn Ile Gly Phe Arg Ser
1               5

<210> SEQ ID NO 29
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Clone XPA.42-681 - L-CDR2

<400> SEQUENCE: 29

Phe Asp Arg
1

<210> SEQ ID NO 30
<211> LENGTH: 11
<212> TYPE: PRT
<213> ORGANISM: Artificial Sequence

```
<220> FEATURE:
<223> OTHER INFORMATION: Synthetic peptide
<220> FEATURE:
<221> NAME/KEY: MISC_FEATURE
<223> OTHER INFORMATION: Clone XPA.42-681 - L-CDR3

<400> SEQUENCE: 30

Gln Val Trp Asp Ser Asp Ser Asp Asp Leu Val
1               5                   10
```

TREATMENT OF CANCER USING ANTI-TGF-BETA AND PD-1 ANTIBODIES

This application claims the priority benefit of U.S. Provisional Patent Application No. 62/143,016, filed Apr. 3, 2015 and U.S. Provisional Patent Application No. 62/191,797, filed Jul. 13, 2015, herein incorporated by reference in their entirety.

This invention was made with government support under Grant Number R21CA164772 and U01CA084244 awarded by the National Institutes of Health. The government has certain rights in the invention.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: One 17,107 byte ASCII (Text) file named "49343_SeqListing.txt" created on Apr. 1, 2016.

FIELD OF THE INVENTION

The present disclosure relates, in general, to combination therapy for treating cancer or preventing the recurrence of cancer comprising administering to a subject in need thereof a therapeutically effective amount of an inhibitor of transforming growth factor beta (TGFβ) and an inhibitor of programmed cell death protein 1 (PD-1).

BACKGROUND

Cancer immunotherapy refers to methods of activating the immune system to induce tumor regression and disease stabilization (Mellman I et al., Nature. 480, 7378: 480-9 (2011)). Antibody therapy directed against certain negative immunologic regulators (immune checkpoints) has been shown to be successful as an anti-tumor treatment in several cancer types (Postow et al., J Clin Oncol 33: 9, (2015)).

The transforming growth factor beta (TGFβ) protein family consists of three distinct isoforms found in mammals (TGFβ1, TGFβ2, and TGFβ3). The TGFβ proteins activate and regulate multiple gene responses that influence disease states, including cell proliferative, inflammatory, and cardiovascular conditions. TGFβ is a multifunctional cytokine originally named for its ability to transform normal fibroblasts to cells capable of anchorage-independent growth. The TGFβ molecules are produced primarily by hematopoietic and tumor cells and can regulate, i.e., stimulate or inhibit, the growth and differentiation of cells from a variety of both normal and neoplastic tissue origins (Sporn et al., Science, 233: 532 (1986)), and stimulate the formation and expansion of various stromal cells.

The TGFβs are known to be involved in many proliferative and non-proliferative cellular processes such as cell proliferation and differentiation, embryonic development, extracellular matrix formation, bone development, wound healing, hematopoiesis, and immune and inflammatory responses. See e.g., Pircher et al, Biochem. Biophys. Res. Commun., 136: 30-37 (1986); Wakefield et al., Growth Factors, 1: 203-218 (1989); Roberts and Sporn, pp 419-472 in Handbook of Experimental Pharmacology eds M. B. Sporn & A. B. Roberts (Springer, Heidelberg, 1990); Massague et al., Annual Rev. Cell Biol., 6: 597-646 (1990); Singer and Clark, New Eng. J. Med., 341: 738-745 (1999). Also, TGFβ is used in the treatment and prevention of diseases of the intestinal mucosa (WO 2001/24813). TGFβ is also known to have strong immunosuppressive effects on various immunologic cell types, including cytotoxic T lymphocyte (CTL) inhibition (Ranges et al., J. Exp. Med., 166: 991, 1987), Espevik et al., J. Immunol., 140: 2312, 1988), depressed B cell lymphopoiesis and kappa light-chain expression (Lee et al., J. Exp. Med., 166: 1290, 1987), negative regulation of hematopoiesis (Sing et al., Blood, 72: 1504, 1988), down-regulation of HLA-DR expression on tumor cells (Czarniecki et al., J. Immunol., 140: 4217, 1988), and inhibition of the proliferation of antigen-activated B lymphocytes in response to B-cell growth factor (Petit-Koskas et al., Eur. J. Immunol., 18: 111, 1988). See also U.S. Pat. No. 7,527,791.

TGFβ isoform expression in cancer is complex and variable with different combinations of TGFβ isoforms having different roles in particular cancers. TGFβ molecules can act both as tumor suppressors and tumor promoters. For example, deletion or downregulation of TGFβ signaling in animals can result in increased breast cancer, intestinal cancer, pancreatic cancer, colon cancer and squamous cell carcinoma, indicating the presence of TGFβ is important to prevent or slow tumor progression (Yang et al., Trends Immunol 31:220-27, 2010). However, overexpression of TGFβ is known to be pro-oncogenic and increased expression is detected in many tumor types (Yang et al., supra).

Antibodies to TGFβ have been described in U.S. Pat. Nos. 7,527,791; 7,927,593; 7,494,651; 7,369,111; 7,151,169; 6,492,497; 6,419,928; 6,090,383; 5,783,185; 5,772,998; 5,571,714; and U.S. Pat. Nos. 7,723,486 and 8,569,462.

Programmed cell death protein 1 (PD-1), also known as cluster of differentiation 279 (CD279), is a cell surface co-inhibitory receptor expressed on activated T cells, B cells and macrophages, and is a component of immune checkpoint blockade (Shinohara et al., Genomics., 23(3):704, (1994); Francisco et al., Immunol Rev., 236: 219, (2010)). PD-1 limits the activity of T cells upon interaction with its two ligands PD-L1 (also known as B7-H1; CD274) and PD-L2 (B7-DC; CD273) (Postow et al., J Clin Oncol., 33: 9, (2015)). Interaction of PD-1 with PD-L1 and PD-L2, reduces T-cell proliferation, cytokine production, and cytotoxic activity (Freeman G J et al., J Exp Med., 192:1027-34, (2000); Brown J A et al., J Immunol., 170:1257-66, (2003)).

Recently, two monoclonal antibodies have been approved by the U.S. Food and Drug Administration (FDA) for the inhibition of PD-1 immunotherapy. Pembrolizumab (KEYTRUDA®, Merck Sharp & Dohme Corp.) is approved for use in metastatic melanoma, and nivolumab (Opdivo®, Bristol-Myers Squibb) is approved for use in metastatic melanoma and metastatic squamous non-small cell lung cancer (NSCLC). Both of these antibodies bind to the PD-1 receptor and block its interaction with its ligands, PD-L1 and PD-L2.

Inhibitors of PD-L1 have also been shown to be effective at inhibiting solid tumors in bladder cancer, head and neck cancer, and gastrointestinal cancers (Herbst R S et al., J Clin Oncol., 31: 3000 (2013); Heery C R et al., J Clin Oncol., 32: 5s, 3064 (2014); Powles T et al., J Clin Oncol, 32: 5s, 5011(2014); Segal N H et al., J Clin Oncol., 32: 5s, 3002 (2014)).

Antibodies to PD-1 have been described in U.S. Pat. Nos. 8,735,553; 8,617,546; 8,008,449; 8,741,295; 8,552,154; 8,354,509; 8,779,105; 7,563,869; 8,287,856; 8,927,697; 8,088,905; 7,595,048; 8,168,179; 6,808,710; 7,943,743; 8,246,955; and 8,217,149.

In the setting of cancer, multiple mechanisms of immune suppression may prevent immunotherapy from being effective. In some cases tumors are refractory to mono-immunotherapy and only a minor fraction of cancers fully respond. Therefore the use of combinations of immunotherapeutic agents will likely be required for optimal patient responses (Hodi F S et al., Adv Immunol., 90:341-68, 2006; Postow et al., J Clin Oncol., 33: 9, 2015).

Recently TGFβ inhibition combined with inhibition of immune checkpoint protein CTLA-4 has been demonstrated to be effective at suppressing melanoma tumor growth and metastasis (Hanks et al., J Clin Oncol 32: 5s, 2014). Combinational immunotherapy approaches using inhibitors of PD-1/PD-L1 and CTLA-4 are currently being evaluated (Sznol M et al., J Clin Oncol., 32: 5s, 2014; Wolchok J D et al., N Engl J Med., 369: 122-133, 2013; Callahan et al., J Clin Oncol., 32:5s, 2014 and reviewed in Postow et al., J Clin Oncol., 33: 9, (2015)). Studies have described synergistic upregulation of IFNγ in effector T cells from tumor-draining lymph nodes following simultaneous blockade of PD-L1 and TGFβ using a combination of monoclonal antibodies implicating PD-L1 and TGFβ in suppressing cellular responses to active immunization in the tumor-bearing host (Wei et al., Cancer Res, 68: 13, 2008).

SUMMARY OF THE INVENTION

The present disclosure relates, in general, to materials and methods for treating cancer or preventing the recurrence of cancer using inhibitors of TGFβ and PD-1 in combinational therapy. Inhibition of TGFβ has been demonstrated to stimulate chemokine secretion and inflammation, while PD-1 blockade has been shown to suppress immune inhibitory mechanisms. The data presented herein demonstrate that inhibitors of TGFβ, in particular when administered with inhibitors of PD-1, elicit tumor regression in mouse models of cancer.

In various embodiments, the present disclosure provides a method for treating cancer or preventing the recurrence of cancer comprising administering to a subject in need thereof therapeutically effective amounts of an inhibitor of transforming growth factor beta (TGFβ) and an inhibitor of Programmed cell death protein 1 (PD-1).

In various embodiments, the methods contemplate use of an antibody that binds transforming growth factor beta (TGFβ)1, TGFβ2 and TGFβ3. In some embodiments, the antibody neutralizes activity of TGFβ1 and TGFβ2 to a greater extent than TGFβ3. In some embodiments, antibody neutralization of TGFβ1 and TGFβ2 is at least 2-50 fold, 10-100 fold, 2-fold, 5-fold, 10-fold, 25-fold, 50-fold or 100-fold, or 20-50%, 50-100%, 20%, 25%, 30%, 40%, 50%, 60%, 70%, 80%, 90% or 100% more potent that neutralization of TGFβ3. Exemplary neutralization assays contemplated herein include, but are not limited to, an interleukin-11 release assay and an HT-2 cell proliferation assay. In addition, a TGFβ activity assay can be carried out to determine if an antibody disclosed herein inhibits one TGFβ isoform preferentially, including a pSMAD phosphorylation assay or an rhLAP binding assay. In a further embodiment, the antibody has a lower IC50 (i.e., better binding, greater potency) for TGFβ1 and TGFβ2 compared to TGFβ.

In various embodiments, the methods contemplate use of an antibody that binds TGFβ, TGFβ2 and TGFβ3 comprising: a heavy chain complementary determining repeat (CDR), CDR1 amino acid sequence set forth in SEQ ID NOs: 13, 19 and 25, or a variant thereof having at least 85% identity thereto; a heavy chain CDR2 amino acid sequence set forth in SEQ ID NOs: 14, 20 and 26, or a variant thereof having at least 85% identity thereto; a heavy chain CDR3 amino acid sequence set forth in SEQ ID NOs: 15, 21 and 27, or a variant thereof having at least 85% identity thereto; a light chain CDR1 amino acid sequence set forth in SEQ ID NOs: 16, 22 and 28, or a variant thereof having at least 85% identity thereto; a light chain CDR2 amino acid sequence set forth in SEQ ID NOs: 17, 23 and 29, or a variant thereof having at least 85% identity thereto; and a light chain CDR3 amino acid sequence set forth in SEQ ID NOs: 18, 24 and 30, or a variant thereof having at least 85% identity thereto. In some embodiments, it is contemplated that an antibody useful in the methods comprises an amino acid sequence at least 85% identical to a heavy chain variable region amino acid sequence set forth in SEQ ID NOs: 2, 6 and 10. In a related embodiment, the antibody comprises an amino acid sequence at least 95% identical to a heavy chain variable region amino acid sequence set forth in SEQ ID NOs: 2, 6 and 10.

In a related embodiment, the antibody comprises an amino acid sequence at least 85% identical to a light chain variable region amino acid sequence set forth in SEQ ID NOs: 4, 8 and 12. In a further embodiment, the antibody comprises an amino acid sequence at least 95% identical to a light chain variable region amino acid sequence set forth in SEQ ID NOs: 4, 8 and 12. In still another embodiment, the antibody comprises a light chain variable region amino acid sequence set forth in SEQ ID NOs: 4, 8 and 12.

In various embodiments, the methods contemplate use of an antibody that binds to TGFβ1 and TGFβ2 with greater affinity than to TGFβ3 comprising: a heavy chain CDR1 amino acid sequence set forth in SEQ ID NO: 19, or a variant thereof in which one or two amino acids have been changed; a heavy chain CDR2 amino acid sequence set forth in SEQ ID NO: 20, or a variant thereof in which one or two amino acids have been changed; a heavy chain CDR3 amino acid sequence set forth in SEQ ID NO: 21, or a variant thereof in which one or two amino acids have been changed; a light chain CDR1 amino acid sequence set forth in SEQ ID NO: 22, or a variant thereof in which one or two amino acids have been changed; a light chain CDR2 amino acid sequence set forth in SEQ ID NO: 23, or a variant thereof in which one or two amino acids have been changed; and a light chain CDR3 amino acid sequence set forth in SEQ ID NO: 24, or a variant thereof in which one or two amino acids have been changed.

In various embodiments, the methods contemplate use of an antibody that neutralizes activity of TGFβ1 and TGFβ2 to a greater extent than it neutralizes the activity of TGFβ3 comprising: a heavy chain CDR1 amino acid sequence set forth in SEQ ID NO: 19, or a variant thereof in which one or two amino acids have been changed; a heavy chain CDR2 amino acid sequence set forth in SEQ ID NO: 20, or a variant thereof in which one or two amino acids have been changed; a heavy chain CDR3 amino acid sequence set forth in SEQ ID NO: 21, or a variant thereof in which one or two amino acids have been changed; a light chain CDR1 amino acid sequence set forth in SEQ ID NO: 22, or a variant thereof in which one or two amino acids have been changed; a light chain CDR2 amino acid sequence set forth in SEQ ID NO: 23, or a variant thereof in which one or two amino acids have been changed; and a light chain CDR3 amino acid sequence set forth in SEQ ID NO: 24, or a variant thereof in which one or two amino acids have been changed.

In one aspect, the methods contemplate use of an antibody that binds TGFβ1, TGFβ2 and TGFβ3 comprising: (a) a heavy chain CDR1 amino acid sequence set forth in SEQ ID NO: 25, or a variant thereof in which one or two amino acids have been changed; (b) a heavy chain CDR2 amino acid sequence set forth in SEQ ID NO: 26, or a variant thereof in which one or two amino acids have been changed; (c) a heavy chain CDR3 amino acid sequence set forth in SEQ ID NO: 27, or a variant thereof in which one or two amino acids have been changed; (d) a light chain CDR1 amino acid sequence set forth in SEQ ID NO: 28, or a variant thereof in which one or two amino acids have been changed; (e) a light chain CDR2 amino acid sequence set forth in SEQ ID NO: 29, or a variant thereof in which one or two amino acids have been changed; and (f) a light chain CDR3 amino acid sequence set forth in SEQ ID NO: 30, or a variant thereof in which one or two amino acids have been changed.

In another aspect, an antibody described herein comprises (a) a heavy chain CDR1 amino acid sequence set forth in SEQ ID NO: 13, or a variant thereof in which one or two amino acids have been changed; (b) a heavy chain CDR2 amino acid sequence set forth in SEQ ID NO: 14, or a variant thereof in which one or two amino acids have been changed; (c) a heavy chain CDR3 amino acid sequence set forth in SEQ ID NO: 15, or a variant thereof in which one or two amino acids have been changed; (d) a light chain CDR1 amino acid sequence set forth in SEQ ID NO: 16, or a variant thereof in which one or two amino acids have been changed; (e) a light chain CDR2 amino acid sequence set forth in SEQ ID NO: 17, or a variant thereof in which one or two amino acids have been changed; and (f) a light chain CDR3 amino acid sequence set forth in SEQ ID NO: 18, or a variant thereof in which one or two amino acids have been changed.

In various embodiments, a TGFβ inhibitor useful in the methods is an antibody comprising: a heavy chain CDR1 amino acid sequence set forth in SEQ ID NO: 19, or a variant thereof in which one or two amino acids have been changed; a heavy chain CDR2 amino acid sequence set forth in SEQ ID NO: 20, or a variant thereof in which one or two amino acids have been changed; a heavy chain CDR3 amino acid sequence set forth in SEQ ID NO: 21, or a variant thereof in which one or two amino acids have been changed; a light chain CDR1 amino acid sequence set forth in SEQ ID NO: 22, or a variant thereof in which one or two amino acids have been changed; a light chain CDR2 amino acid sequence set forth in SEQ ID NO: 23, or a variant thereof in which one or two amino acids have been changed; and a light chain CDR3 amino acid sequence set forth in SEQ ID NO: 24, or a variant thereof in which one or two amino acids have been changed.

In a related embodiment, an antibody described herein comprises the heavy chain variable region amino acid sequence as set forth in SEQ ID NO: 10 and the light chain variable region amino acid sequence as set forth in SEQ ID NO: 12.

In a related embodiment, an antibody described herein comprises the heavy chain variable region amino acid sequence is set forth in SEQ ID NO: 2 and the light chain variable region amino acid sequence is set forth in SEQ ID NO: 4.

In a related embodiment, an antibody described herein comprises the heavy chain variable region amino acid sequence is set forth in SEQ ID NO: 6 and the light chain variable region amino acid sequence is set forth in SEQ ID NO: 8.

In some embodiments, an antibody useful in the methods further comprises a heavy chain constant region, wherein the heavy chain constant region is a modified or unmodified IgG, IgM, IgA, IgD, IgE, a fragment thereof, or combinations thereof.

In one embodiment, an antibody used herein further comprises a human light chain constant region attached to said light chain variable region. In some embodiments, the light chain constant region is a modified or unmodified lambda light chain constant region, a kappa light chain constant region, a fragment thereof, or combinations thereof.

In some embodiments, it is contemplated that the PD-1 inhibitor is an antibody that binds PD-1 such as a monoclonal antibody disclosed in the Detailed Description. In various embodiments, the anti-PD-1 antibody inhibits or blocks binding of the PD-1 receptor to one or both of its ligands, PD-L1 and PD-L2.

In a related aspect, the disclosure describes the use of a PD-1 inhibitor used in combination with one or more of the above TGFβ monoclonal antibodies.

In a related aspect, the disclosure provides a method for treating cancer or preventing the reoccurrence of cancer comprising administering to a subject in need thereof a therapeutically effective amount of the antibodies or pharmaceutical compositions contemplated herein. In certain embodiments, the cancer is selected from the group consisting of esophageal cancer, pancreatic cancer, metastatic pancreatic cancer, metastatic adenocarcinoma of the pancreas, bladder cancer, stomach cancer, fibrotic cancer, glioma, malignant glioma, diffuse intrinsic pontine glioma, recurrent childhood brain neoplasm renal cell carcinoma, clear-cell metastatic renal cell carcinoma, kidney cancer, prostate cancer, metastatic castration resistant prostate cancer, stage IV prostate cancer, metastatic melanoma, melanoma, malignant melanoma, recurrent melanoma of the skin, melanoma brain metastases, stage IIIA skin melanoma; stage IIIB skin melanoma, stage IIIC skin melanoma; stage IV skin melanoma, malignant melanoma of head and neck, lung cancer, non small cell lung cancer (NSCLC), squamous cell non-small cell lung cancer, breast cancer, recurrent metastatic breast cancer, hepatocellular carcinoma, hodgkin's lymphoma, follicular lymphoma, non-hodgkin's lymphoma, advanced B-cell NHL, HL including diffuse large B-cell lymphoma (DLBCL) including DLBCL following autologous stem cell transplantation, multiple myeloma, chronic myeloid leukemia, adult acute myeloid leukemia in remission; adult acute myeloid leukemia with Inv(16)(p13.1q22); CBFB-MYH11; adult acute myeloid leukemia with t(16;16) (p13.1;q22); CBFB-MYH11; adult acute myeloid leukemia with t(8;21)(q22;q22); RUNX1-RUNX1T1; adult acute myeloid leukemia with t(9;11)(p22;q23); MLLT3-MLL; adult acute promyelocytic leukemia with t(15;17)(q22;q12); PML-RARA; alkylating agent-related acute myeloid leukemia, chronic lymphocytic leukemia, richter's syndrome; waldenstrom macroglobulinemia, adult glioblastoma; adult gliosarcoma, recurrent glioblastoma, recurrent childhood rhabdomyosarcoma, recurrent ewing sarcoma/peripheral primitive neuroectodermal tumor, recurrent neuroblastoma; recurrent osteo sarcoma, colorectal cancer, MSI positive colorectal cancer; MSI negative colorectal cancer, nasopharyngeal nonkeratinizing carcinoma; recurrent nasopharyngeal undifferentiated carcinoma, cervical adenocarcinoma; cervical adenosquamous carcinoma; cervical squamous cell carcinoma; recurrent cervical carcinoma; stage IVA cervical cancer; stage IVB cervical cancer, anal canal squamous cell carcinoma; metastatic anal canal carcinoma; recurrent anal canal carcinoma, recurrent head and neck cancer; head and neck squamous cell carcinoma (HNSCC), ovarian carcinoma, colon cancer, gastric cancer, advanced GI cancer, gastric adenocarcinoma; gastroesophageal junction adenocarcinoma, bone neoplasms, soft tissue sarcoma; bone sarcoma, thymic carcinoma, urothelial carcinoma, recurrent merkel cell carcinoma; stage III merkel cell carcinoma; stage IV merkel cell carcinoma, myelodysplastic syndrome and recurrent mycosis fungoides and Sezary syndrome.

In a related aspect, the disclosure provides a method for treating cancer or preventing the reoccurrence of cancer comprising administering to a subject in need thereof a therapeutically effective amount of the antibodies or pharmaceutical compositions contemplated herein. In certain embodiments, the cancer is selected from the group consisting of non small cell lung carcinoma (NSCLC), head and neck cancer, skin cancer, melanoma and squamous cell carcinoma (SCC).

In certain embodiments, the cancer has a mutation in the V-Ki-ras2 Kirsten rat sarcoma viral oncogene homolog (KRAS) oncogene.

In certain embodiments, the cancer has a mutation in the Harvey rat sarcoma viral oncogene homolog (HRAS) oncogene.

In certain embodiments, the cancer has a mutation in the neuroblastoma RAS viral (v-ras) oncogene homolog (NRAS) oncogene.

In certain embodiments, the cancer has mutations in the RAS oncogene.

In a related aspect, the cancer is selected from the group consisting of lung adenocarcinoma, mucinous adenoma, ductal carcinoma of the pancreas and colorectal carcinoma, brain lower grade glioma, breast invasive carcinoma, glioblastoma multiforme, melanoma, thyroid, rectum adenocarcinoma, kidney cancer, renal cancer, liver cancer, acute myeloid leukemia, gastric adenocarcinoma, esophageal adenocarcinoma, uterine corpus endometrioid carcinoma, bladder cancer, prostate cancer, oral cancer, large intestine cancer and lymphoma.

It is contemplated that the methods herein reduce tumor size or tumor burden in the subject, and/or reduce metastasis in the subject. In various embodiments, the methods reduce the tumor size by 10%, 20%, 30% or more. In various embodiments, the methods reduce tumor size by 10%, 15%, 20%, 25%, 30%, 35%, 40%, 45%, 50%, 55%, 60%, 65%, 70%, 75%, 80%, 85%, 90%, 95% or 100%.

It is contemplated that the methods herein reduce tumor burden, and also reduce or prevent the recurrence of tumors once the cancer has gone into remission.

In another aspect, the disclosure provides a method for treating a disease, condition or disorder associated with TGFβ and PD-1 signaling and/or expression comprising the step of administering to a subject in need thereof a therapeutically effective amount of an antibody or a pharmaceutical composition contemplated herein. In certain embodiments, the disease, condition or disorder is selected from a group of cancers.

The disclosure further contemplates a sterile pharmaceutical composition comprising a TGFβ inhibitor, a PD-1 inhibitor and a pharmaceutically acceptable carrier.

The disclosure further contemplates a sterile pharmaceutical composition comprising a separate TGFβ inhibitor and a pharmaceutically acceptable carrier.

The disclosure further contemplates a sterile pharmaceutical composition comprising a separate PD-1 inhibitor and a pharmaceutically acceptable carrier.

It is contemplated that inhibitors, such as antibodies, of the present disclosure may be given simultaneously, in the same formulation. It is further contemplated that the inhibitors are administered in a separate formulation and administered concurrently, with concurrently referring to agents given within 30 minutes of each other. It is further contemplated that a third agent may be given simultaneously with the inhibitors.

In another aspect, the disclosure provides a method for treating or preventing recurrence of a disease, condition or disorder associated with TGFβ and PD-1 signaling and/or expression comprising the step of administering to a subject in need thereof a therapeutically effective amount of an antibody or a pharmaceutical composition contemplated herein wherein the administration prevents the reoccurrence of cancer in a subject that has received inhibitor therapy.

In some embodiments, the TGFβ antibody and/or PD-1 antibody and combinations thereof or compositions described herein increases the number of natural killer (NK) cells in a tumor. In various embodiments, the antibody or composition increases cytolytic activity of NK cells. For example, in various embodiments, the antibodies or composition described herein increases perforin and granzyme production by NK cells.

In various embodiments, the TGFβ antibody and/or PD-1 antibody and combinations thereof or compositions described herein decreases the number of regulatory T cells in a tumor and/or inhibits regulatory T cell function. For example, in various embodiments, the antibodies or composition described herein inhibits the ability of Tregs to down-regulate an immune response or to migrate to a site of an immune response.

In various embodiments, the TGFβ antibody and/or PD-1 antibody and combinations thereof or compositions described herein increases the number of cytotoxic T cells in a tumor and/or enhances CTL activity, e.g., boosts, increases or promotes CTL activity. For example, in various embodiments, the antibodies or composition described herein increases perforin and granzyme production by CTL and increases cytolytic activity of the CTL.

In various embodiments, the TGFβ antibody and/or PD-1 antibody and combinations thereof or compositions described herein increases the number of dendritic cells (DC) in a tumor and/or inhibits the tolerogenic function (e.g., tolerogenic effect) of dendritic cells. For example, in various embodiments, the antibodies or composition described herein decreases the tolerogenic effect of CD8+ dendritic cells.

In various embodiments, administration of the TGFβ antibody and/or PD-1 antibody and combinations thereof or compositions described herein increases the ratio of effector T cells to regulatory T cells in a tumor.

In various embodiments, the disclosure provides a method for increasing the ratio of effector T cells to regulatory T cells in a tumor comprising administering to a subject in need thereof therapeutically effective amounts of an inhibitor of transforming growth factor beta (TGFβ3) and an inhibitor of Programmed cell death protein 1 (PD-1).

In various embodiments, therapy is administered on a period basis, for example, hourly, daily, twice weekly, weekly, every 2 weeks, every 3 weeks, monthly, once every two months or at a longer interval. In a related embodiment, in exemplary treatments, a TGFβ inhibitor is administered in a dose range of 0.1 to 15 mg/kg and a PD-1 inhibitor is administered in a dose range from 0.1 to 15 mg/kg. These concentrations may be administered as a single dosage form or as multiple doses.

In various embodiments, the inhibitors are administered with a third agent. In one embodiment, the third agent is selected from the group consisting of an extracellular matrix degrading protein, an anti-fibrotic agent, surgical therapy, chemotherapy (e.g. cisplatin plus pemetrexed, carboplatin plus paclitaxel), a cytotoxic agent (e.g. lenalidomide, dexamethasone), or radiation therapy (Philips and Atkins, Int Immunol., 27(1):39-46 (2015) which is incorporated herein by reference). Exemplary third agents are disclosed in greater detail in the Detailed Description.

Also contemplated is a composition comprising any of the foregoing antibodies or compositions of the disclosure that bind TGFβ or PD-1, or use thereof in preparation of a medicament, for treatment of any of the disorders described herein associated with TGFβ and PD-1 signaling and/or expression. Syringes, e.g., single use or pre-filled syringes, sterile sealed containers, e.g. vials, bottle, vessel, and/or kits or packages comprising any of the foregoing antibodies or compositions, optionally with suitable instructions for use, are also contemplated.

It is understood that each feature or embodiment, or combination, described herein is a non-limiting, illustrative example of any of the aspects of the invention and, as such, is meant to be combinable with any other feature or embodiment, or combination, described herein. For example, where features are described with language such as "one embodiment", "some embodiments", "certain embodiments", "further embodiment", "specific exemplary embodiments", and/ or "another embodiment", each of these types of embodiments is a non-limiting example of a feature that is intended to be combined with any other feature, or combination of features, described herein without having to list every possible combination. Such features or combinations of features apply to any of the aspects of the invention. Where examples of values falling within ranges are disclosed, any of these examples are contemplated as possible endpoints of a range, any and all numeric values between such endpoints are contemplated, and any and all combinations of upper and lower endpoints are envisioned.

In one aspect, the TGFβ antibody useful in the methods is selected from the group consisting of XPA.42.089, XPA.42.068 and XPA.42.681. Heavy and light chain amino acid sequences of XPA.42.089 are set out in SEQ ID NOs: 6 and 8, respectively. Heavy and light chain amino acid sequences of XPA.42.068 are set out in SEQ ID NOs: 2 and 4, respectively, and heavy and light chain amino acid sequences of XPA.42.681 are set out in SEQ ID NOs: 10 and 12, respectively.

In one aspect, the TGFβ antibody useful in the methods is Fresolimumab (GC1008, Cambridge Antibody Technology, Genzyme and Sanofi), currently in Phase I clinical trials (Morris J C et al., PLoS One. 2014 Mar. 11; 9(3):e90353, 2014; Akhurst and Hata, Nat Rev Drug Discov., 11: 790-811, 2012) see U.S. Pat. No. 7,723,486.

In one aspect, the PD-1 antibody useful in the methods is selected from the group consisting of pembrolizumab, nivolumab and pidilizumab.

BRIEF DESCRIPTION OF THE DRAWINGS

FIG. 1A-1C show tumor inhibition in a allograft mouse model with TGFβ and PD-1 inhibitor mono- and combination therapy. FIG. 1A shows growth of tumors in mice implanted with cSCC cells. Also shown is the amount of CD45+, Natural killer (NK) cells, regulatory T (Treg) cells, CD4+ and CD8+ T cells represented as a percentage of viable cells (FIG. 1B) and as a percentage of CD45+ cells (FIG. 1C).

FIG. 2A-2C show the differential responses of individual tumors to immunotherapy. Data from FIG. 1 were segregated into "responders" and "progressors" to demonstrate the range of responses to α-PD-1 (FIG. 2A), α-TGFβ (FIG. 2B), and combination therapy (FIG. 2C).

FIG. 3A-3D show the differential responses of individual tumors to immunotherapy. Data from FIG. 1 were plotted as separate tumor measurements over time for control (ctrl) (FIG. 3A), α-PD-1 monotherapy (FIG. 3B), α-TGFβ monotherapy (FIG. 3C), and α-PD-1 and α-TGFβ in combination (FIG. 3D).

FIG. 6A shows the percentage of carcinomas displaying disease progression (continued tumor growth), complete response (i.e. inhibition/regression of carcinoma growth) or partial response to the indicated therapies. FIG. 6B shows the percentage survival of mice in response to pan specific α-TGFβ1, 2, 3 and α-PD1 monotherapy and combinational therapy in this model. FIG. 6C shows the levels of immune cell markers, CD8+ effector (Teff), CD4+ effector (Teff), CD4+ regulatory T (Treg) cells as a percentage of CD45+ and the ratio of Teff/Treg for tumors responding and not responding (i.e. progressing tumor growth) to treatment with pan specific α-TGFβ1,2,3 and PD-1 inhibitor monotherapy and combinational therapy.

DETAILED DESCRIPTION

Figure 1C:
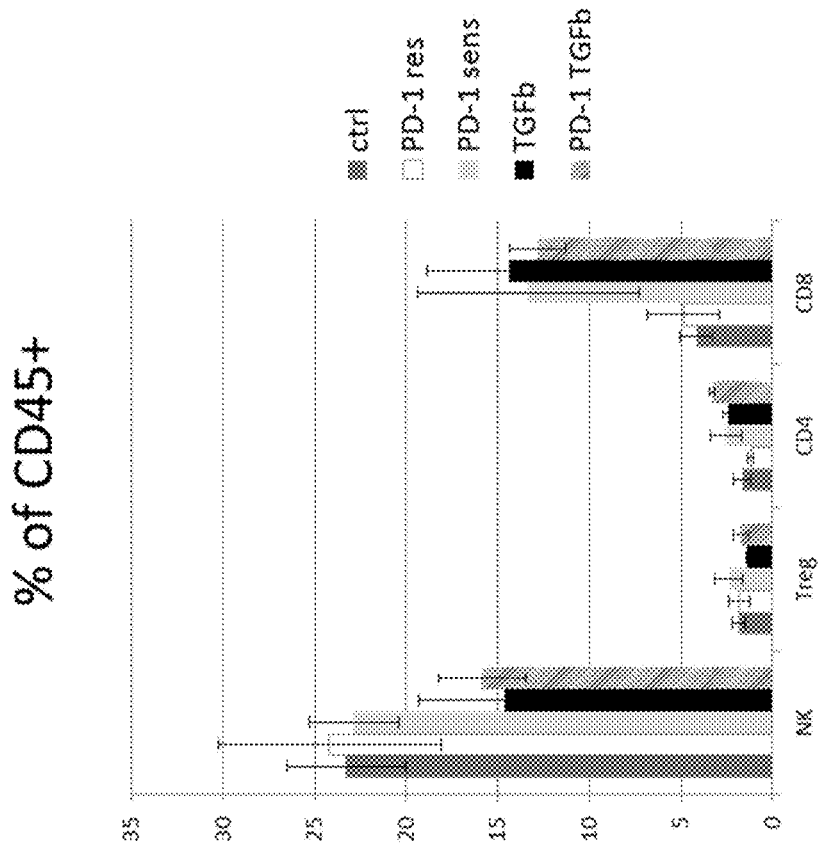

The present disclosure provides therapeutics for treating cancer or preventing the recurrence of cancer. The present disclosure provides molecules or agents that interact with TGFβ and PD-1 and inhibit one or more of their functional effects, such as for example signaling through binding partners of TGFβ or PD-1. The compositions disclosed herein advantageously have the ability to modulate immune cell activity in tumors, thereby providing, in one aspect, a method to treat cancer by affecting a cell population that directly or indirectly affects growth of the tumor.

Definitions

As used herein "TGFβ" refers to any one or more isoforms of TGFβ, including TGFβ1, TGFβ2 and TGFβ3 or variants thereof. Likewise, the term "TGFβ receptor," unless otherwise indicated, refers to any receptor that binds at least one TGFβ isoform.

As used herein "Programmed cell death protein 1" or "PD-1" refers to a cell surface receptor involved in immune checkpoint blockade mediated by binding to two ligands, PD-L1 and PD-L2. PD-1 binding to its ligands has been shown to reduce T-cell proliferation, cytokine production, and cytotoxic activity.

As used herein, the "desired biological activity" of an anti-target antibody is the ability to bind to TGFβ or PD-1 and inhibit one or more of their functional effects.

As used herein, a "condition" or "disorder" associated with a "target" in which modification of target activity by a target inhibitor described herein is beneficial and also includes other disorders in which high levels of target have been shown to be or are suspected of being either responsible for the pathophysiology of the disorder or a factor that contributes to a worsening of the disorder, as well as diseases and other disorders in which modulation of the target is associated with changes in clinical signs or symptoms. Such disorders may be evidenced, for example, by an increase in the levels of target secreted and/or on the cell surface and/or modified target signaling in the affected cells or tissues of a subject suffering from the disorder.

Exemplary diseases, conditions or disorders that can be treated with an inhibitor that inhibits TGFβ and an inhibitor that inhibits PD-1 or an inhibitor of both TGFβ and PD-1 (e.g., antibodies described herein) include cancers, such as esophageal cancer, pancreatic cancer, metastatic pancreatic cancer, metastatic adenocarcinoma of the pancreas, bladder cancer, stomach cancer, fibrotic cancer, glioma, malignant glioma, diffuse intrinsic pontine glioma, recurrent childhood brain neoplasm renal cell carcinoma, clear-cell metastatic renal cell carcinoma, kidney cancer, prostate cancer, metastatic castration resistant prostate cancer, stage IV prostate cancer, metastatic melanoma, melanoma, malignant melanoma, recurrent melanoma of the skin, melanoma brain metastases, stage IIIA skin melanoma; stage IIIB skin melanoma, stage IIIC skin melanoma; stage IV skin melanoma, malignant melanoma of head and neck, lung cancer, non small cell lung cancer (NSCLC), squamous cell non-small cell lung cancer, breast cancer, recurrent metastatic breast cancer, hepatocellular carcinoma, hodgkin's lymphoma, follicular lymphoma, non-hodgkin's lymphoma, advanced B-cell NHL, HL including diffuse large B-cell lymphoma (DLBCL), multiple myeloma, chronic myeloid leukemia, adult acute myeloid leukemia in remission; adult acute myeloid leukemia with Inv(16)(p13.1q22); CBFB-MYH11; adult acute myeloid leukemia with t(16;16)(p13.1;q22); CBFB-MYH11; adult acute myeloid leukemia with t(8;21) (q22;q22); RUNX1-RUNX1T1; adult acute myeloid leukemia with t(9;11)(p22;q23); MLLT3-MLL; adult acute promyelocytic leukemia with t(15;17)(q22;q12); PML-RARA; alkylating agent-related acute myeloid leukemia, chronic lymphocytic leukemia, richter's syndrome; waldenstrom macroglobulinemia, adult glioblastoma; adult gliosarcoma, recurrent glioblastoma, recurrent childhood rhabdomyosarcoma, recurrent ewing sarcoma/peripheral primitive neuroectodermal tumor, recurrent neuroblastoma; recurrent osteosarcoma, colorectal cancer, MSI positive colorectal cancer; MSI negative colorectal cancer, nasopharyngeal nonkeratinizing carcinoma; recurrent nasopharyngeal undifferentiated carcinoma, cervical adenocarcinoma; cervical adenosquamous carcinoma; cervical squamous cell carcinoma; recurrent cervical carcinoma; stage IVA cervical cancer; stage IVB cervical cancer, anal canal squamous cell carcinoma; metastatic anal canal carcinoma; recurrent anal canal carcinoma, recurrent head and neck cancer; carcinoma, squamous cell of head and neck, head and neck squamous cell carcinoma (HNSCC), ovarian carcinoma, colon cancer, gastric cancer, advanced GI cancer, gastric adenocarcinoma; gastroesophageal junction adenocarcinoma, bone neoplasms, soft tissue sarcoma; bone sarcoma, thymic carcinoma, urothelial carcinoma, recurrent merkel cell carcinoma; stage III merkel cell carcinoma; stage IV merkel cell carcinoma, myelodysplastic syndrome and recurrent mycosis fungoides and Sezary syndrome.

An "immunoglobulin" or "native antibody" is a tetrameric glycoprotein. In a naturally-occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa (κ) and lambda (λ) light chains. Heavy chains are classified as mu (μ), delta (Δ), gamma (γ), alpha (α), and epsilon (ε), and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology, Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains (Chothia et al., J. Mol. Biol. 196:901-917, 1987).

Immunoglobulin variable domains exhibit the same general structure of relatively conserved framework regions (FR) joined by three hypervariable regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest (National Institutes of Health, Bethesda, Md. (1987 and 1991)), or Chothia & Lesk, (J. Mol. Biol. 196:901-917, 1987); Chothia et al., (Nature 342:878-883, 1989).

The hypervariable region of an antibody refers to the CDR amino acid residues of an antibody which are responsible for antigen-binding. The hypervariable region comprises amino acid residues from a CDR [e.g., residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, 5th Ed. Public Health Service, National Institutes of Health, Bethesda, Md. (1991)] and/or those residues from a hypervariable loop (e.g., residues 26-32 (L1), 50-52 (L2) and 91-96 (L3) in the light chain variable domain and 26-32 (H1), 53-55 (H2) and 96-101 (H3) in the heavy chain variable domain as described by [Chothia et al., J. Mol. Biol. 196: 901-917 (1987)]. CDRs have also been identified and numbered according to ImMunoGenTics (IMGT) numbering (Lefranc, M.-P., The Immunologist, 7, 132-136 (1999); Lefranc, M.-P. et al., Dev. Comp. Immunol., 27, 55-77

(2003), which describes the CDR locations in the light and heavy chain variable domains as follows: CDR1, approximately residues 27 to 38; CDR2, approximately residues 56 to 65; and, CDR3, approximately residues 105 to 116 (germline) or residues 105 to 117 (rearranged). In one embodiment, it is contemplated that the CDRs are located at approximately residues 26-31 (L1), 49-51 (L2) and 88-98 (L3) in the light chain variable domain and approximately residues 26-33 (H1), 50-58 (H2) and 97-111 (H3) in the heavy chain variable domain of an antibody heavy or light chain of approximately similar length to those disclosed herein. However, one of skill in the art understands that the actual location of the CDR residues may vary from the projected residues described above when the sequence of the particular antibody is identified.

Framework or FR residues are those variable domain residues other than the hypervariable region residues.

"Heavy chain variable region" as used herein refers to the region of the antibody molecule comprising at least one complementarity determining region (CDR) of said antibody heavy chain variable domain. The heavy chain variable region may contain one, two, or three CDR of said antibody heavy chain.

"Light chain variable region" as used herein refers to the region of an antibody molecule, comprising at least one complementarity determining region (CDR) of said antibody light chain variable domain. The light chain variable region may contain one, two, or three CDRs of said antibody light chain, which may be either a kappa or lambda light chain depending on the antibody.

The term "antibody" is used in the broadest sense and includes fully assembled antibodies, tetrameric antibodies, monoclonal antibodies, polyclonal antibodies, multispecific antibodies (e.g., bispecific antibodies), antibody fragments that can bind an antigen (e.g., Fab', F'(ab)2, Fv, single chain antibodies, diabodies), and recombinant peptides comprising the forgoing as long as they exhibit the desired biological activity. An "immunoglobulin" or "tetrameric antibody" is a tetrameric glycoprotein that consists of two heavy chains and two light chains, each comprising a variable region and a constant region. Antigen-binding portions may be produced by recombinant DNA techniques or by enzymatic or chemical cleavage of intact antibodies. Antibody fragments or antigen-binding portions include, inter alia, Fab, Fab', F(ab')2, Fv, domain antibody (dAb), complementarity determining region (CDR) fragments, CDR-grafted antibodies, single-chain antibodies (scFv), single chain antibody fragments, chimeric antibodies, diabodies, triabodies, tetrabodies, minibody, linear antibody; chelating recombinant antibody, a tribody or bibody, an intrabody, a nanobody, a small modular immunopharmaceutical (SMIP), an antigen-binding-domain immunoglobulin fusion protein, a camelized antibody, a VHH containing antibody, or a variant or a derivative thereof, and polypeptides that contain at least a portion of an immunoglobulin that is sufficient to confer specific antigen binding to the polypeptide, such as one, two, three, four, five or six CDR sequences, as long as the antibody retains the desired biological activity.

"Monoclonal antibody" refers to an antibody obtained from a population of substantially homogeneous antibodies, i.e., the individual antibodies comprising the population are identical except for possible naturally occurring mutations that may be present in minor amounts.

"Antibody variant" as used herein refers to an antibody polypeptide sequence that contains at least one amino acid substitution, deletion, or insertion in the variable region of the reference antibody variable region domains. Variants may be substantially homologous or substantially identical to the unmodified antibody.

A "chimeric antibody," as used herein, refers to an antibody containing sequence derived from two different antibodies (see, e.g., U.S. Pat. No. 4,816,567) which typically originate from different species. Most typically, chimeric antibodies comprise human and rodent antibody fragments, generally human constant and mouse variable regions.

A "neutralizing antibody" is an antibody molecule which is able to eliminate or significantly reduce a biological function of a target antigen to which it binds. Accordingly, a "neutralizing" anti-target antibody is capable of eliminating or significantly reducing a biological function, such as enzyme activity, ligand binding, or intracellular signaling.

An "isolated" antibody is one that has been identified and separated and recovered from a component of its natural environment. Contaminant components of its natural environment are materials that would interfere with diagnostic or therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

As used herein, an antibody that "specifically binds" is "target specific", is "specific for" target or is "immunoreactive" with the target antigen refers to an antibody or antibody substance that binds the target antigen with greater affinity than with similar antigens. In one aspect of the disclosure, the target-binding polypeptides, or fragments, variants, or derivatives thereof, will bind with a greater affinity to human target as compared to its binding affinity to target of other, i.e., non-human, species, but binding polypeptides that recognize and bind orthologs of the target are within the scope provided.

For example, a polypeptide that is an antibody or fragment thereof "specific for" its cognate antigen indicates that the variable regions of the antibodies recognize and bind the polypeptide of interest with a detectable preference (i.e., able to distinguish the polypeptide of interest from other known polypeptides of the same family, by virtue of measurable differences in binding affinity, despite the possible existence of localized sequence identity, homology, or similarity between family members). It will be understood that specific antibodies may also interact with other proteins (for example, *S. aureus* protein A or other antibodies in ELISA techniques) through interactions with sequences outside the variable region of the antibodies, and in particular, in the constant region of the molecule. Screening assays to determine binding specificity of an antibody for use in the methods of the present disclosure are well known and routinely practiced in the art. For a comprehensive discussion of such assays, see Harlow et al. (Eds), Antibodies A Laboratory Manual; Cold Spring Harbor Laboratory; Cold Spring Harbor, N.Y. (1988), Chapter 6. Antibodies for use in the methods can be produced using any method known in the art.

The term "epitope" refers to that portion of any molecule capable of being recognized by and bound by a selective binding agent at one or more of the antigen binding regions. Epitopes usually consist of chemically active surface groupings of molecules, such as, amino acids or carbohydrate side chains, and have specific three-dimensional structural characteristics as well as specific charge characteristics. Epitopes as used herein may be contiguous or non-contiguous. Moreover, epitopes may be mimetic (mimotopes) in that they comprise a three dimensional structure that is identical to the epitope used to generate the antibody, yet comprise none or only some of the amino acid residues found in the target that were used to stimulate the antibody immune response. As used herein, a mimotope is not considered a different antigen from the epitope bound by the selective binding agent; the selective binding agent recognizes the same three-dimensional structure of the epitope and mimotope.

The term "derivative" when used in connection with antibody substances and polypeptides of the present disclosure refers to polypeptides chemically modified by such techniques as ubiquitination, conjugation to therapeutic or diagnostic agents, labeling (e.g., with radionuclides or various enzymes), covalent polymer attachment such as pegylation (derivatization with polyethylene glycol) and insertion or substitution by chemical synthesis of amino acids such as ornithine, which do not normally occur in human proteins. Derivatives retain the binding properties of underivatized molecules of the disclosure.

"Detectable moiety" or a "label" refers to a composition detectable by spectroscopic, photochemical, biochemical, immunochemical, or chemical means. For example, useful labels include 32P, 35S, fluorescent dyes, electron-dense reagents, enzymes (e.g., as commonly used in an ELISA), biotin-streptavadin, dioxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantitate the amount of bound detectable moiety in a sample.

The term "therapeutically effective amount" is used herein to indicate the amount of target-specific composition of the disclosure that is effective to ameliorate or lessen symptoms or signs of disease to be treated.

The terms "treat", "treated", "treating" and "treatment", as used with respect to methods herein refer to eliminating, reducing, suppressing or ameliorating, either temporarily or permanently, either partially or completely, a clinical symptom, manifestation or progression of an event, disease or condition. Such treating need not be absolute to be useful.

The present methods provides for use of target-specific antibodies, which may comprise those exemplary sequences set out herein, fragments, variants and derivatives thereof, pharmaceutical formulations including a target-specific antibodies recited herein. Depending on the amino acid sequence of the constant domain of their heavy chains, immunoglobulins can be assigned to different classes, IgA, IgD, IgE, IgG and IgM, which may be further divided into subclasses or isotypes, e.g. IgG1, IgG2, IgG3, IgG4, IgA1 and IgA2. The subunit structures and three-dimensional configurations of different classes of immunoglobulins are well known. Different isotypes have different effector functions; for example, IgG1 and IgG3 isotypes have ADCC activity. An antibody disclosed herein, if it comprises a constant domain, may be of any of these subclasses or isotypes.

The antibodies used in the present methods may exhibit binding affinity to one or more TGFβ and/or PD-1 antigens of a Kd of less than or equal to about $10^{-5}$ M, less than or equal to about $10^{-6}$ M, or less than or equal to about $10^{-7}$ M, or less than or equal to about $10^{-8}$ M, or less than or equal to about $10^{-9}$ M, $10^{-10}$ M, $10^{-11}$ M, or $10^{-12}$ M or less. Such affinities may be readily determined using conventional techniques, such as by equilibrium dialysis; by using surface plasmon resonance (SPR) technology (e.g., the BIAcore 2000 instrument, using general procedures outlined by the manufacturer); by radioimmunoassay using $^{125}$I labeled target antigen; or by another method set forth in the examples below or known to the skilled artisan. The affinity data may be analyzed, for example, by the method of Scatchard et al., (Ann N.Y. Acad. Sci., 51:660, 1949).

A KinExA kinetic exclusion assay is also useful to measure the affinity of an antibody for its antigen. KinExA technology measures binding events in the solution phase, rather than binding events between a solution phase and a solid phase. In addition, while many methods for measuring binding events require at least one reactant be modified through immobilization or labeling, the KinExA method does not require modification of molecules under study. The KinExA method is believed to allow a wider range of binding constants to be measured than other methods currently available. Additional description about KinExA devices and operation for antibody characterization is available from the manufacturer (Sapidyne Instruments, Inc., Boise, Id.) and can be found in the published literature, for example U.S. Pat. No. 6,664,114 and Darling et al., "Kinetic Exclusion Assay Technology: Characterization of Molecular Interactions." Assay and Drug Development Technologies, 2004, 2:647-657.

Transforming Growth Factor β

TGFβ is a disulfide linked dimer that is synthesized as a preproprotein of about 400 amino acids (aa) which is cleaved prior to secretion to produce mature TGFβ. The N-terminal cleavage fragment, known as the "latency-associated peptide" (LAP), may remain noncovalently bound to the dimer, thereby inactivating TGFβ. TGFβ isolated in vivo, is found predominantly in the inactive, "latent" form, i.e., associated with LAP. Latent TGFβ complex may be activated in several ways, for example, by binding to a cell surface receptor called the cation-independent mannose-6-phosphate/insulin-like growth factor II receptor. Binding occurs through mannose-6-phosphate residues attached at glycosylation sites within LAP. Upon binding to the receptor, TGFβ is released in its mature form. Mature, active TGFβ is then free to bind to its receptor and exert its biological functions. The major TGFβ binding domain in the type II TGFβ receptor has been mapped to a 19 amino acid sequence (Demetriou et al., J. Biol. Chem., 271:12755, 1996). See also U.S. Pat. Nos. 7,867,496 and 8,569,462.

Currently, there are five known isoforms of TGFβ (TGFβ1 to TGFβ5; TGFβ1-3 are mammalian, TGFβ4 is found in chicken; and TGFβ5 found in frog), all of which are homologous among each other (60-80% identity), form homodimers of about 25 kDa, and act upon common TGFβ receptors (TGFβ-RI, TGFβ-RII, TGFβ-RIIB, and TGFβ-RIII). The structural and functional aspects of TGFβ as well as TGFβ receptors are well-known in the art (see, for example, Cytokine Reference, eds. Oppenheim et al., Academic Press, San Diego, Calif., 2001). TGFβ is well-conserved among species. For example, the amino acid sequences of rat and human mature TGFβ is are nearly identical. See also U.S. Pat. No. 7,867,496.

TGFβ1 plays an important role in the process of wound healing in biological tissues (New Engl. J. Med., Vol. 331, p. 1286, 1994 and J. Cell. Biol., Vol. 119, p. 1017, 1992). At the site of wounded tissue, biological reactions such as infiltration of inflammatory cells and fibroblast cells, production of extracellular rmatrix (ECM) and vascularization, and cell growth for the subsequent tissue regeneration occur to repair the injured tissue. See also U.S. Pat. No. 7,579,186.

TGFβ2 deficient mice demonstrate significant developmental defects, including heart, lung, craniofacial, limb, spine, eye, ear and urogenital defects (Dunker et al., Eur J Biol 267:6982-8, 2001). TGFβ3 deficient mice demonstrate almost 100% lethality by 24 hrs after birth. These mice show significant palate impairment and delayed pulmonary development (Dunker et al., supra). TGFβ2 has also been implicated in the development of glaucoma (Luthen-Driscoll, Experimental Eye Res 81:1-4, 2005), fibrosis associated with Crohn's Disease (Van Assche et al., Inflamm Bowel Dis. 10:55-60, 2004), in wound healing and diabetic nephropathy (Pohlers et al., Biochim Biophys Acta 1792:746-56, 2009)

It has been observed that many human tumors (deMartin et al., EMBO J., 6: 3673 (1987), Kuppner et al., Int. J. Cancer, 42: 562 (1988)) and many tumor cell lines (Derynck et al., Cancer Res., 47: 707 (1987), Roberts et al., Br. J. Cancer, 57: 594 (1988)) produce TGFβ.

TGFβ isoform expression in cancer is complex and variable with different combinations of TGFβ isoforms having different roles in particular cancers. See e.g., U.S. Pat. No. 7,927,593. For example, TGFβ1 and TGFβ3 may play a greater role in ovarian cancer and its progression than TGFβ2; while TGFβ1 and TGFβ2 expression is greater in higher grade chondrosarcoma tumors than TGFβ3. In human breast cancer, TGFβ1 and TGFβ3 are highly expressed, with TGFβ3 expression appearing to correlate with overall survival—patients with node metastasis and positive TGFβ3 expression have poor prognostic outcomes. However, in colon cancer, TGFβ1 and TGFβ2 are more highly expressed than TGFβ3 and are present at greater circulating levels than in cancer-free individuals. In gliomas, TGFβ2 is important for cell migration.

TGFβ Antibodies

The present disclosure encompasses use of amino acid molecules encoding target specific antibodies. In exemplary embodiments, a target specific antibody useful in the methods of the disclosure can comprise a human kappa (κ) or a human lambda (λ) light chain or an amino acid sequence derived therefrom, or a human heavy chain or a sequence derived therefrom, or both heavy and light chains together in a single chain, dimeric, tetrameric or other form. In some embodiments, a heavy chain and a light chain of a target specific immunoglobulin are different amino acid molecules. In other embodiments, the same amino acid molecule contains a heavy chain variable region and a light chain variable region of a target specific antibody.

In some embodiments, the amino acid sequence of the human anti-target antibody for TGFβ useful in the methods comprises one or more CDRs of the amino acid sequence of the mature (i.e., missing signal sequence) light chain variable region (VL) of antibodies XPA.42.068, XPA.42.089 and XPA.42.681 (SEQ ID NOs: 4, 8 and 12 respectively) or variants thereof, including CDR grafted, modified, humanized, chimeric, or Human Engineered antibodies or any other variants described herein. In some embodiments, the VL comprises the amino acid sequence from the beginning of the CDR1 to the end of the CDR3 of the light chain of any one of the foregoing antibodies.

In one embodiment, the target specific antibody comprises a light chain CDR1, CDR2 or CDR3 (LCDR1, LCDR2, LCDR3), each of which are independently selected from the CDR1, CDR2 and CDR3 regions of an antibody having a light chain variable region comprising the amino acid sequence of the VL region set out in SEQ ID NOs: 4, 8 and 12, a nucleic acid encoding the VH region set out in SEQ ID NOs: 4, 8, and 12, or encoded by a nucleic acid molecule encoding the VL region set out in SEQ ID NOs: 3, 7, and 11. In one embodiment, the light chain CDR1 is from approximately residues 24-34, CDR2 is from approximately residues 50-56 and CDR3 extends from approximately residues 89-97, according to Chothia numbering. In an alternate embodiment, it is contemplated that the heavy chain CDRs are located at approximately residues 27 to 38 (CDR1); approximately residues 56 to 65 (CDR2); and, approximately residues 105 to 116 (germline) or residues 105 to 117 (CDR3) according to ImMunoGenTics (IMGT) numbering. In one embodiment, it is contemplated that the light chain CDRs are located at approximately residues 26-31 (L1), 49-51 (L2) and 88-97 (L3) in the light chain variable domain of an antibody light chain of approximately similar length to those disclosed herein. A polypeptide of the target specific antibody may comprise the CDR1, CDR2 and CDR3 regions of an antibody comprising the amino acid sequence of the VL region selected from the group consisting of XPA.42.068, XPA.42.089 and XPA.42.681.

In some embodiments, the human target specific antibody for TGFβ comprises one or more CDRs of the amino acid sequence of the mature (i.e., missing signal sequence) heavy chain variable region (VH) of antibody XPA.42.068, XPA.42.089 and XPA.42.681 set out in SEQ ID NOs: 2, 6 and 10, respectively, or variants thereof. In some embodiments, the VH comprises the amino acid sequence from the beginning of the CDR1 to the end of the CDR3 of any one of the heavy chain of the foregoing antibodies.

In one embodiment, the target specific antibody comprises a heavy chain CDR1, CDR2 or CDR3 (HCDR1, HCDR2, HCDR3), each of which are independently selected from the CDR1, CDR2 and CDR3 regions of an antibody having a heavy chain variable region comprising the amino acid sequence of the VH region set out in SEQ ID NOs: 2, 6, and 10, a nucleic acid encoding the VH region set out in SEQ ID NOs: 2, 6, and 10, or encoded by a nucleic acid molecule encoding the VH region set out in SEQ ID NOs: 1, 5, and 9. It is further contemplated that a target specific antibody comprises a heavy chain CDR1, CDR2 or CDR3, each of which are independently selected from the CDR1, CDR2 and CDR3 regions of an antibody having a heavy chain variable region comprising the amino acid sequence of the VH region set out in SEQ ID NOs: 2, 6, and 10. In one embodiment, the heavy chain CDRs are located according to Chothia numbering: CDR1 is from approximately residues 26-35, CDR2 is from approximately residues 50-58 and CDR3 extends from approximately residues 95-102 (or 95-111 or 95-118). In an alternate embodiment, it is contemplated that the heavy chain CDRs are located at CDR1, approximately residues 27 to 38 (CDR1); approximately residues 56 to 65 (CDR2); and, CDR3, approximately residues 105 to 116 (germline) or residues 105 to 117 CDR3) according to ImMunoGenTics (IMGT) numbering. In one embodiment, it is contemplated that the heavy chain CDRs are located at approximately residues 26-33 (H1), 50-58 (H2) and 97-111 (H3) in the heavy chain variable domain of an antibody heavy chain of approximately similar length to those disclosed herein. A polypeptide of the target specific antibody may comprise the CDR1, CDR2 and CDR3 regions of an antibody comprising the amino acid sequence of the VH region selected from the group consisting of XPA.42.068, XPA.42.089 and XPA.42.681.

In another embodiment, the TGFβ antibody comprises a mature light chain variable region as disclosed above and a mature heavy chain variable region as disclosed above, optionally paired with the correspondingly named heavy or light chain, or optionally with a different heavy or light chain.

In exemplary embodiments, the disclosure contemplates use of: a monoclonal antibody that retains any one, two, three, four, five, or six of HCDR1, HCDR2, HCDR3, LCDR1, LCDR2, or LCDR3 of any one of SEQ ID NOs: 13, 19 and 25; 14, 20 and 26; 15, 21 and 27 and SEQ ID NOs: 16, 22 and 28; 17, 23 and 29; and 18, 24 and 30, respectively, optionally including one or two mutations in any of such CDR(s), e.g., a conservative or non-conservative substitution, and optionally paired. a monoclonal antibody that retains all of HCDR1, HCDR2, HCDR3, or the heavy chain variable region of any one of SEQ ID NOs: 13, 19 and 25; 14, 20 and 26; and 15, 21 and 27, optionally including one or two mutations in any of such CDR(s), optionally further comprising any suitable heavy chain constant region, e.g., IgG1, IgG2, IgG3, IgG4, IgM, IgA1, IgA2, or IgE, a human sequence thereof, or a hybrid thereof; a monoclonal antibody that retains all of LCDR1, LCDR2, LCDR3, or the light chain variable region of any one SEQ ID NOs: 16, 22 and 28; 17, 23 and 29; and 18, 24 and 30, optionally including one or two mutations in any of such CDR(s), optionally further comprising any suitable light chain constant region, e.g., a kappa or lambda light chain constant region, a human sequence thereof, or a hybrid thereof.

In some embodiments, an antibody useful in the methods comprises all three light chain CDRs, all three heavy chain CDRs, or all six CDRs of the light and heavy chain. In some exemplary embodiments, two light chain CDRs from an antibody may be combined with a third light chain CDR from a different antibody. Alternatively, a LCDR1 from one antibody can be combined with a LCDR2 from a different antibody and a LCDR3 from yet another antibody, particularly where the CDRs are highly homologous. Similarly, two heavy chain CDRs from an antibody may be combined with a third heavy chain CDR from a different antibody; or a HCDR1 from one antibody can be combined with a HCDR2 from a different antibody and a HCDR3 from yet another antibody, particularly where the CDRs are highly homologous.

In some embodiments, an antibody useful in the methods comprises a polypeptide having an amino acid sequence at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to the heavy chain variable region set out in SEQ ID NOs: 2, 6, and 10 and/or an amino acid sequence an amino acid sequence at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to the light chain variable region set out in SEQ ID NOs: 4, 8 and 12, the antibody further comprising at least one, two, three, four, five or all of HCDR1, HCDR2, HCDR3, LCDR1, LCDR2 or LCDR3. In some embodiments, the amino acid sequence with percentage identity to the light chain variable region may comprise one, two or three of the light chain CDRs. In other embodiments, the amino acid sequence with percentage identity to the heavy chain variable region may comprise one, two, or three of the heavy chain CDRs.

In another embodiment, an antibody useful in the methods comprises a polypeptide having an amino acid sequence at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to all three HCDRs in the heavy chain variable region of an antibody sequence described herein, the CDRs set out in SEQ ID NOs: 13, 19 and 25; 14, 20 and 26; and 15, 21 and 27.

In a related embodiment, an antibody useful in the methods comprises a polypeptide having an amino acid sequence at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to the all three LCDRs in the light chain variable region of an antibody sequence described herein, the CDRs set out in SEQ ID NOs: 16, 22 and 28; 17, 23 and 29; and 18, 24 and 30.

In a further embodiment, an antibody useful in the methods comprises a polypeptide having an amino acid sequence at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to the all six CDRs in the heavy chain and light chain variable regions of an antibody sequence described herein, the CDRs set out in SEQ ID NOs: 13, 19 and 25; 14, 20 and 26; and 15, 21 27; 16, 22 and 28; 17, 23 and 29; and 18, 24 and 30.

It is contemplated that the antibodies described herein may have one, or two or more amino acid substitutions in the CDR regions of the antibody, e.g., non-conservative or conservative substitutions.

In a related embodiment, the residues of the framework are altered. The heavy chain framework regions which can be altered lie within regions designated H-FR1, H-FR2, H-FR3 and H-FR4, which surround the heavy chain CDR residues, and the residues of the light chain framework regions which can be altered lie within the regions designated L-FR1, L-FR2, L-FR3 and L-FR4, which surround the light chain CDR residues. An amino acid within the framework region may be replaced, for example, with any suitable amino acid identified in a human framework or human consensus framework.

In exemplary embodiments, an anti-TGFβ antibody described herein specifically binds at least one isoform of TGFβ selected from the group consisting of TGFβ1, TGFβ2, and TGFβ3. In other embodiments, the anti-TGFβ antibody specifically binds: (a) TGFββ1, TGFβ2, and TGFβ3 ("pan-reactive antibody" or "pan-binding antibody"); (b) TGFβ1 and TGFβ2; (c) TGFβ1 and TGFβ3; and (d) TGFβ2 and TGFβ3. In exemplary embodiments, an anti-TGFβ antibody described herein binds at least one isoform of TGFβ with an affinity of $10^{-6}$M, $10^{-7}$ M, $10^{-8}$ M, $10^{-9}$ M, $10^{-10}$ M, $10^{-11}$ M, or $10^{-12}$ M or less (lower meaning higher binding affinity), or optionally binds two TGFβ isoforms, or all of TGFβ1, 2, or 3 with an affinity of $10^{-6}$M. $10^{-7}$ M, $10^{-8}$ M, $10^{-9}$ M $10^{-10}$ M, $10^{-11}$ M, or $10^{-12}$ M or less for one or more of the isoforms. In other embodiments, an antibody described herein binds to TGFβ1 and TGFβ2 with at least 2-50 fold, 10-100 fold, 2-fold, 5-fold, 10-fold, 25-fold, 50-fold or 100-fold, or 20-50%, 50-100%, 20%, 25%, 30%, 40%, 50%, 60%, 70%, 80%, 90% or 100% higher affinity (e.g., preferentially binds to TGFβ1 and TGFβ2) compared to binding to TGFβ3. Alternatively, an antibody described herein, binds each of TGFβ isoforms TGFβ1, TGFβ2 and TGFβ3 with an affinity within 3-fold, 5-fold or 10-fold of each other.

In some embodiments, antibody neutralization of TGFβ1 and TGFβ2 is at least 2-50 fold, 10-100 fold, 2-fold, 5-fold, 10-fold, 25-fold, 50-fold or 100-fold, or 20-50%, 50-100%, 20%, 25%, 30%, 40%, 50%, 60%, 70%, 80%, 90% or 100% more potent than neutralization of TGFβ3.

Heavy and light chain amino acid sequences of XPA.42.089 are set out in SEQ ID NOs: 6 and 8, respectively. Heavy and light chain amino acid sequences of XPA.42.068 are set out in SEQ ID NOs: 2 and 4, respectively, and heavy and light chain amino acid sequences of XPA.42.681 are set out in SEQ ID NOs: 10 and 12, respectively.

Antibody Nucleic Acids

The present disclosure also encompasses use of nucleic acid molecules encoding target specific antibodies described herein and in the Sequence Listing, optionally for recombinantly producing an antibody described herein or for generating antibody variants. In some embodiments, different nucleic acid molecules encode a heavy chain variable region and a light chain variable region of a target specific antibody. In other embodiments, the same nucleic acid molecule encodes a heavy chain and a light chain variable regions of a target specific antibody. In one embodiment, the nucleic acid encodes a target specific antibody of the present disclosure, as well as any of the polypeptides encoded by the nucleic acids described herein.

Nucleic acid sequences encoding anti-TGFβ antibodies contemplated for use in the methods include all nucleic acid sequences, including the sequences in SEQ ID NOs: 1, 3, 5, 7, 9 and 11 and nucleic acid sequences comprises degenerate codons based on the diversity of the genetic code, encoding an amino acid sequence of the heavy and light chain variable regions of an antibody described herein or any HCDRs or LCDRs described herein, and as set out in SEQ ID NOs: 2, 4, 6, 8, 10, 12 and 13-30, as well as nucleic acids that hybridize under highly stringent conditions, such as those described herein, to a nucleic acid sequence encoding an amino acid sequence of the heavy and light chain variable regions of an antibody described herein or any HCDRs or LCDRs described herein, and as set out in SEQ ID NOs: 2, 4, 6, 8, 10, 12 and 13-30.

Preparation of variants and derivatives of antibodies and antigen-binding compounds of the present invention, including affinity maturation or preparation of variants or derivatives containing amino acid analogs, is described in further detail herein. Exemplary variants include those containing a conservative or non-conservative substitution of a corresponding amino acid within the amino acid sequence, or a replacement of an amino acid with a corresponding amino acid of a different human antibody sequence. Variants and fragments of an antibody disclosed herein are made using methods as described herein and known in the field of recombinant protein production.

Programmed Cell Death Protein 1 (PD-1)

PD-1, also known as cluster of differentiation 279 (CD279) is a membrane protein of 268 amino acids. PD-1 is a member of the CD28/CTLA-4 family of T cell regulator proteins (Ishida Y et al., The EMBO J., 11 (11): 3887-95, (1992)). PD-1 is a cell surface co-inhibitory receptor expressed on CD4+ and CD8+ T cells, B cells and macrophages, and is a component of immune checkpoint blockade (Shinohara et al., Genomics., 23(3):704, (1994); Francisco et al., Immunol Rev., 236: 219, (2010)). PD-1 limits the activity of T cells upon interaction with its two ligands PD-L1 (also known as B7-H1; CD274) and PD-L2 (B7-DC; CD273) (Freeman G J et al., J. Exp. Med. 192 (7): 1027-34, 2000; Latchman Y et al., Nat. Immunol., 2 (3): 261-8, 2001; Postow et al., J Clin Oncol., 33: 9, 2015). Interaction of PD-1 with PD-L1 and PD-L2, reduces T cell proliferation, cytokine production, and cytotoxic activity (Freeman G J et al., J Exp Med., 192:1027-34, (2000); Brown J A et al., J Immunol., 170:1257-66, (2003)).

PD-1 Antibodies

Antibodies to PD-1 have been described in U.S. Pat. Nos. 8,735,553; 8,617,546; 8,008,449; 8,741,295; 8,552,154; 8,354,509; 8,779,105; 7,563,869; 8,287,856; 8,927,697; 8,088,905; 7,595,048; 8,168,179; 6,808,710; 7,943,743; 8,246,955; and 8,217,149.

It is contemplated that any known antibody can be used in the present methods. In some embodiments, a murine monoclonal anti-target antibody for human PD-1 is used in the present methods. For example, InVivo MAb anti h PD-1 (BioXCell, Clone: RMP1-14, Cat. no.: BE0146). Anti-PD-1 antibodies have been shown to be effective in human therapy, see e.g., pembrolizumab (KEYTRUDA®, Merck Sharp & Dohme Corp.) and nivolumab (Opdivo®, Bristol-Myers Squibb) which are anti-PD-1 antibodies approved for use in human therapy. Additional PD-1 antibodies are in clinical development, e.g. pidilizumab (CT-011) (CureTech Ltd.).

Alternatively, antibodies to PD-1 are made using techniques known in the art and described herein, including phage display technology, hybridoma technology, transgenic mouse technology and others.

In various embodiments, a bispecific antibody that binds both a TGFβ and a PD-1 protein is useful in the present methods.

Monoclonal Antibodies

Monoclonal antibody refers to an antibody obtained from a population of substantially homogeneous antibodies. Monoclonal antibodies are generally highly specific, and may be directed against a single antigenic site, in contrast to polyclonal antibody preparations that typically include different antibodies directed against the same or different determinants (epitopes). In addition to their specificity, monoclonal antibodies are advantageous in that they are synthesized by the homogeneous culture, uncontaminated by other immunoglobulins with different specificities and characteristics.

Monoclonal antibodies may be made by the hybridoma method first described by Kohler et al. (Nature, 256:495-7, 1975) (Harlow & Lane; Antibodies: A Laboratory Manual, Cold Spring Harbor Laboratory Press: Cold Spring Harbor, N.Y. (1988); Goding, Monoclonal Antibodies: Principles and Practice, pp. 59-103 (Academic Press, 1986), or may be made by recombinant DNA methods (see, e.g., U.S. Pat. No. 4,816,567). The monoclonal antibodies may also be isolated from phage antibody libraries using the techniques described in, for example, Clackson et al., (Nature 352:624-628, 1991) and Marks et al., (J. Mol. Biol. 222:581-597, 1991). Additional methods for producing monoclonal antibodies are well-known to a person of ordinary skill in the art.

Monoclonal antibodies, such as those produced by the above methods, are suitably separated from culture medium, ascites fluid, or serum by conventional immunoglobulin purification procedures such as, for example, protein A-Sepharose, hydrophobic interaction chromatography (HIC), ion exchange chromatography, hydroxyapatite chromatography, gel electrophoresis, dialysis, and/or affinity chromatography.

It is further contemplated that antibodies of the present disclosure may be used as smaller antigen binding fragments of the antibody that are well-known in the art and described herein.

Antibody Fragments

Antibody fragments comprise a portion of an intact full length antibody, preferably an antigen binding or variable region of the intact antibody. Examples of antibody fragments include Fab, Fab', F(ab')2, and Fv fragments; diabodies; linear antibodies; single-chain antibody molecules (e.g., scFv); multispecific antibody fragments such as bispecfic, trispecific, etc. antibodies (e.g., diabodies, triabodies, tetrabodies); minibody; chelating recombinant antibody; tribodies or bibodies; intrabodies; nanobodies; small modular immunopharmaceuticals (SMIP), binding-domain immunoglobulin fusion proteins; camelized antibodies; VHH containing antibodies; and other polypeptides formed from antibody fragments. See for example Holliger & Hudson (Nat. Biotech. 23:1126-36 (2005)).

Papain digestion of antibodies produces two identical antigen-binding fragments, called "Fab" fragments, monovalent fragments consisting of the VL, VH, CL and CH domains each with a single antigen-binding site, and a residual "Fc" fragment, whose name reflects its ability to crystallize readily. Pepsin treatment yields a F(ab')2 fragment, a bivalent fragment comprising two Fab fragments linked by a disulfide bridge at the hinge region, that has two "Single-chain Fv" or "scFv" antibody fragments comprise the VH and VL domains of antibody, wherein these domains are present in a single polypeptide chain. Preferably, the Fv polypeptide further comprises a polypeptide linker between the VH and VL domains that enables the Fv to form the desired structure for antigen binding, resulting in a single-chain antibody (scFv), in which a VL and VH region are paired to form a monovalent molecule via a synthetic linker that enables them to be made as a single protein chain (Bird et al., Science 242:423-426, 1988, and Huston et al., Proc. Natl. Acad. Sci. USA 85:5879-5883, 1988). For a review of scFv see Pluckthun, in The Pharmacology of Monoclonal Antibodies, vol. 1 13, Rosenburg and Moore eds., Springer-Verlag, New York, pp. 269-315 (1994). An Fd fragment consists of the VH and CH1 domains.

Additional antibody fragments include a domain antibody (dAb) fragment (Ward et al., Nature 341:544-546, 1989) which consists of a VH domain. Diabodies are bivalent antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., EP 404,097; WO 93/11161; Holliger et al., Proc. Natl. Acad. Sci. USA 90:6444-6448, 1993, and Poljak et al., Structure 2:1121-1123, 1994). Diabodies can be bispecific or monospecific.

Functional heavy-chain antibodies devoid of light chains are naturally occurring in nurse sharks (Greenberg et al., Nature 374:168-73, 1995), wobbegong sharks (Nuttall et al., Mol Immunol. 38:313-26, 2001) and Camelidae (Hamers-Casterman et al., Nature 363: 446-8, 1993; Nguyen et al., J. Mol. Biol. 275: 413, 1998), such as camels, dromedaries, alpacas and llamas. The antigen-binding site is reduced to a single domain, the VHH domain, in these animals. These antibodies form antigen-binding regions using only heavy chain variable region, i.e., these functional antibodies are homodimers of heavy chains only having the structure H2L2 (referred to as "heavy-chain antibodies" or "HCAbs"). Camelid VHH reportedly recombines with IgG2 and IgG3 constant regions that contain hinge, CH2, and CH3 domains and lack a CH1 domain (Hamers-Casterman et al., supra). For example, llama IgG1 is a conventional (H2L2) antibody isotype in which VH recombines with a constant region that contains hinge, CH1, CH2 and CH3 domains, whereas the llama IgG2 and IgG3 are heavy chain-only isotypes that lack CH1 domains and that contain no light chains. Camelid VHH domains have been found to bind to antigen with high affinity (Desmyter et al., J. Biol. Chem. 276:26285-90, 2001) and possess high stability in solution (Ewert et al., Biochemistry 41:3628-36, 2002). Classical VH-only fragments are difficult to produce in soluble form, but improvements in solubility and specific binding can be obtained when framework residues are altered to be more VHH-like. (See, e.g., Reichman, et al., J Immunol Methods 1999, 231:25-38.) Methods for generating antibodies having camelid heavy chains are described in, for example, in U.S. Patent Publication Nos. 20050136049 and 20050037421.

The variable domain of an antibody heavy-chain is the smallest fully functional antigen-binding fragment with a molecular mass of only 15 kDa, this entity is referred to as a nanobody (Cortez-Retamozo et al., Cancer Research 64:2853-57, 2004). A nanobody library may be generated from an immunized dromedary as described in Conrath et al., (Antimicrob Agents Chemother 45: 2807-12, 2001) or using recombinant methods as described in Revets et al, Expert Opin. Biol. Ther. 5(1):111-24 (2005).

Production of bispecific Fab-scFv ("bibody") and trispecific Fab-(scFv)(2) ("tribody") are described in Schoonjans et al. (J Immunol. 165:7050-57, 2000) and Willems et al. (J Chromatogr B Analyt Technol Biomed Life Sci. 786:161-76, 2003). For bibodies or tribodies, a scFv molecule is fused to one or both of the VL-CL (L) and VH-CH1 (Fd) chains, e.g., to produce a tribody two scFvs are fused to C-term of Fab while in a bibody one scFv is fused to C-term of Fab.

A "minibody" consisting of scFv fused to CH3 via a peptide linker (hingeless) or via an IgG hinge has been described in Olafsen, et al., Protein Eng Des Sel. 17(4):315-23, 2004.

Intrabodies are single chain antibodies which demonstrate intracellular expression and can manipulate intracellular protein function (Biocca, et al., EMBO J. 9:101-108, 1990; Colby et al., Proc Natl Acad Sci USA. 101:17616-21, 2004). Intrabodies, which comprise cell signal sequences which retain the antibody construct in intracellular regions, may be produced as described in Mhashilkar et al (EMBO J 14:1542-51, 1995) and Wheeler et al. (FASEB J. 17:1733-5. 2003). Transbodies are cell-permeable antibodies in which a protein transduction domain (PTD) is fused with single chain variable fragment (scFv) antibodies Heng et al., (Med Hypotheses. 64:1105-8, 2005).

Further contemplated are antibodies that are SMIPs or binding domain immunoglobulin fusion proteins specific for target protein. These constructs are single-chain polypeptides comprising antigen binding domains fused to immunoglobulin domains necessary to carry out antibody effector functions. See e.g., WO03/041600, U.S. Patent publication 20030133939 and US Patent Publication 20030118592.

One or more CDRs may be incorporated into a molecule either covalently or noncovalently to make it an immunoadhesin. An immunoadhesin may incorporate the CDR(s) as part of a larger polypeptide chain, may covalently link the CDR(s) to another polypeptide chain, or may incorporate the CDR(s) noncovalently. The CDRs permit the immunoadhesin to specifically bind to a particular antigen of interest.

Thus, a variety of compositions comprising one, two, and/or three CDRs (e.g., a single CDR alone or in tandem, 2, 3, or other multiple repeats of the CDRs; or combinations of 2 or 3 CDRs alone or in tandem repeats; optionally, with a spacer amino acid sequence between the CDRs or repeats) of a heavy chain variable region or a light chain variable region of an antibody may be generated by techniques known in the art.

Multispecific Antibodies

In some embodiments, it may be desirable to generate multispecific (e.g. bispecific) anti-target antibody having binding specificities for at least two different epitopes of the same or different molecules. Exemplary bispecific antibodies may bind to two different epitopes of the target molecule. Alternatively, a TGFβ-specific antibody arm may be combined with an arm which binds to PD-1. Bispecific antibodies may also be used to localize cytotoxic agents to cells which express or take up a target. These antibodies possess a target-binding arm and an arm which binds the cytotoxic agent (e.g., saporin, anti-interferon-60, vinca alkaloid, ricin A chain, methotrexate or radioactive isotope hapten). Bispecific antibodies can be prepared as full length antibodies or antibody fragments (e.g., F(ab')2 bispecific antibodies). See also reviews of the methods and therapeutic benefits of bispecific antibodies in Spasevska I, BioSciences Master Reviews, 2014; Caravella J and Lugovskoy A, Curr Opin Chem Biol., 14(4) 520-528, 2010

According to another approach for making bispecific antibodies, the interface between a pair of antibody molecules can be engineered to maximize the percentage of heterodimers which are recovered from recombinant cell culture. The preferred interface comprises at least a part of the CH3 domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. See WO96/27011.

Bispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., (Science 229:81-83, 1985) describe a procedure wherein intact antibodies are proteolytically cleaved to generate F(ab')2 fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes. In yet a further embodiment, Fab'-SH fragments directly recovered from *E. coli* can be chemically coupled in vitro to form bispecific antibodies. (Shalaby et al., J. Exp. Med. 175:217-225 (1992))

Shalaby et al., J. Exp. Med. 175:217-225 (1992) describe the production of a fully humanized bispecific antibody F(ab')2 molecule. Each Fab' fragment was separately secreted from *E. coli* and subjected to directed chemical coupling in vitro to form the bispecfic antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. (Kostelny et al., J. Immunol. 148:1547-1553, 1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al. (Proc. Natl. Acad. Sci. USA 90:6444-48, 1993) has provided an alternative mechanism for making bispecific antibody fragments.

The fragments comprise a heavy chain variable region (VH) connected to a light-chain variable region (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (scFv) dimers has also been reported. See Gruber et al., J. Immunol. 152: 5368 (1994).

Alternatively, the bispecific antibody may be a "linear antibody" produced as described in Zapata et al. Protein Eng. 8:1057-62 (1995). Linear antibodies comprise a pair of tandem Fd segments (VH-CH1-VH-CH1) which form a pair of antigen binding regions. Linear antibodies can be bispecific or monospecific.

In a further embodiment, the bispecific antibody may be a chelating recombinant antibody (CRAb). A chelating recombinant antibody recognizes adjacent and non-overlapping epitopes of the target antigen, and is flexible enough to bind to both epitopes simultaneously (Neri et al., J Mol Biol. 246:367-73, 1995).

Antibodies with more than two valencies are also contemplated. For example, trispecific antibodies can be prepared. (Tutt et al., J. Immunol. 147:60, 1991).

Chimeric and Humanized Antibodies

Because chimeric or humanized antibodies are less immunogenic in humans than the parental non-human (e.g., mouse) monoclonal antibodies, they can be used for the treatment of humans with far less risk of anaphylaxis.

Chimeric monoclonal antibodies, in which the variable Ig domains of a non-human (e.g., mouse)monoclonal antibody are fused to human constant Ig domains, can be generated using standard procedures known in the art (See Morrison et al., Proc. Natl. Acad. Sci. USA 81, 6841-6855 (1984); and, Boulianne et al, Nature 312, 643-646, (1984)).

Humanized antibodies may be achieved by a variety of methods including, for example: (1) grafting the non-human complementarity determining regions (CDRs) onto a human framework and constant region (a process referred to in the art as humanizing through "CDR grafting"), (2) transplanting the entire non-human variable domains, but "cloaking" them with a human-like surface by replacement of surface residues (a process referred to in the art as "veneering"), or, alternatively, (3) substituting human amino acids at positions determined to be unlikely to adversely effect either antigen binding or protein folding, but likely to reduce immunogenicity in a human environment (e.g., HUMAN ENGINEERING™). In the present disclosure, humanized antibodies will include both "humanized," "veneered" and "HUMAN ENGINEERED™" antibodies. These methods are disclosed in, e.g., Jones et al., Nature 321:522 525 (1986); Morrison et al., Proc. Natl. Acad. Sci., U.S.A., 81:6851-6855 (1984); Morrison and Oi, Adv. Immunol., 44:65-92 (1988); Verhoeyer et al., Science 239:1534-1536 (1988); Padlan, Molec. Immun. 28:489-498 (1991); Padlan, Molec. Immunol. 31:169-217 (1994); Studnicka et al. U.S. Pat. No. 5,766,886; Studnicka et al., (Protein Engineering 7: 805-814, 1994; Co et al., J. Immunol. 152, 2968-2976 (1994); Riechmann, et al., Nature 332:323-27 (1988); and Kettleborough et al., Protein Eng. 4:773-783 (1991) each of which is incorporated herein by reference. CDR grafting techniques are known in the field, see for example, Riechmann, et al. (Nature 332:323-27 (1988)).

Human Antibodies from Transgenic Animals

Human antibodies to target protein can also be produced using transgenic animals that have no endogenous immunoglobulin production and are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/00906 also discloses transgenic non-primate mammalian hosts capable of mounting an immune response to an immunogen, wherein the antibodies have primate constant and/or variable regions, and wherein the endogenous immunoglobulin encoding loci are substituted or inactivated. WO 96/30498 and U.S. Pat. No. 6,091,001 disclose the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy chains, and express an exogenous immunoglobulin locus comprising one or more xenogeneic constant regions. See also, U.S. Pat. No. 6,114,598 6,657,103 and 6,833,268; Green L L, Curr Drug Discovery Technol., 11(1), 74-84, 2014; Lee E C et al., Nature Biotechnology, 32:356-363, 2014; Lee E C and Owen M, Methods Mol Biol., 901:137-48, 2012).

Using a transgenic animal described above, an immune response can be produced to a selected antigenic molecule, and antibody producing cells can be removed from the animal and used to produce hybridomas that secrete human monoclonal antibodies. Immunization protocols, adjuvants, and the like are known in the art, and are used in immunization of, for example, a transgenic mouse as described in WO 96/33735. This publication discloses monoclonal antibodies against a variety of antigenic molecules including IL-6, IL-8, TNFa, human CD4, L selectin, gp39, and tetanus toxin. The monoclonal antibodies can be tested for the ability to inhibit or neutralize the biological activity or physiological effect of the corresponding protein. WO 96/33735 discloses that monoclonal antibodies against IL-8, derived from immune cells of transgenic mice immunized with IL-8, blocked IL-8 induced functions of neutrophils. Human monoclonal antibodies with specificity for the antigen used to immunize transgenic animals are also disclosed in WO 96/34096 and U.S. patent application no. 20030194404; and U.S. patent application no. 20030031667.

Additional transgenic animals useful to make monoclonal antibodies include the Medarex HuMAb-MOUSE®, described in U.S. Pat. No. 5,770,429 and Fishwild, et al. (Nat. Biotechnol. 14:845-851 (1996)), which contains gene sequences from unrearranged human antibody genes that code for the heavy and light chains of human antibodies. Immunization of a HuMAb-MOUSE® enables the production of fully human monoclonal antibodies to the target protein.

Also, Ishida et al. (Cloning Stem Cells. 4:91-102 (2002)) describes the TransChromo Mouse (TCMOUSE™) which comprises megabase-sized segments of human DNA and which incorporates the entire human immunoglobulin (hIg) loci. The TCMOUSE™ has a fully diverse repertoire of hIgs, including all the subclasses of IgGs (IgG1-G4). Immunization of the TCMOUSE™ with various human antigens produces antibody responses comprising human antibodies.

See also Jakobovits et al., Proc. Natl. Acad. Sci. USA, 90:2551 (1993); Jakobovits et al., Nature, 362:255-258 (1993); Bruggermann et al., Year in Immunol., 7:33 (1993); and U.S. Pat. No. 5,591,669, U.S. Pat. No. 5,589,369, U.S. Pat. No. 5,545,807; and U.S. Patent Publication No. 20020199213. U.S. Patent Publication No. 20030092125 describes methods for biasing the immune response of an animal to the desired epitope. Human antibodies may also be generated by in vitro activated B cells (see U.S. Pat. Nos. 5,567,610 and 5,229,275).

Human Antibodies from Display Technology

The development of technologies for making repertoires of recombinant human antibody genes, and the display of the encoded antibody fragments on the surface of filamentous bacteriophage, has provided a means for making human antibodies directly. Antibodies produced by phage technology are produced as antigen binding fragments-usually Fv or Fab fragments-in bacteria and thus lack effector functions. Effector functions can be introduced by one of two strategies: The fragments can be engineered, for example, into complete antibodies for expression in mammalian cells, or into bispecific antibody fragments with a second binding site capable of triggering an effector function.

By way of example, one method for preparing the library of antibodies for use in phage display techniques comprises the steps of immunizing a non-human animal comprising human immunoglobulin loci with target antigen or an antigenic portion thereof to create an immune response, extracting antibody producing cells from the immunized animal; isolating RNA from the extracted cells, reverse transcribing the RNA to produce cDNA, amplifying the cDNA using a primer, and inserting the cDNA into a phage display vector such that antibodies are expressed on the phage. Recombinant target-specific antibodies of the disclosure may be obtained in this way.

In another example, antibody producing cells can be extracted from non-immunized animals, RNA isolated from the extracted cells and reverse transcribed to produce cDNA, which is amplified using a primer, and inserted into a phage display vector such that antibodies are expressed on the phage. Phage-display processes mimic immune selection through the display of antibody repertoires on the surface of filamentous bacteriophage, and subsequent selection of phage by their binding to an antigen of choice. One such technique is described in WO 99/10494, which describes the isolation of high affinity and functional agonistic antibodies for MPL and msk receptors using such an approach. Antibodies of the disclosure can be isolated by screening of a recombinant combinatorial antibody library, preferably a scFv phage display library, prepared using human VL and VH cDNAs prepared from mRNA derived from human lymphocytes. Methodologies for preparing and screening such libraries are known in the art. See e.g., U.S. Pat. No.

5,969,108. There are commercially available kits for generating phage display libraries (e.g., the Pharmacia Recombinant Phage Antibody System, catalog no. 27-9400-01; and the Stratagene SurfZAP™ phage display kit, catalog no. 240612). There are also other methods and reagents that can be used in generating and screening antibody display libraries (see, e.g., Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) Bio/Technology 9:1370-1372; Hay et al. (1992) Hum. Antibod. Hybridomas 3:81-85; Huse et al. (1989) Science 246:1275-1281; McCafferty et al., Nature (1990) 348:552-554; Griffiths et al. (1993) EMBO J 12:725-734; Hawkins et al. (1992) J. Mol. Biol. 226:889-896; Clackson et al. (1991) Nature 352:624-628; Gram et al. (1992) Proc. Natl. Acad. Sci. USA 89:3576-3580; Garrad et al. (1991) Bio/Technology 9:1373-1377; Hoogenboom et al. (1991) Nuc Acid Res 19:4133-4137; and Barbas et al. (1991) Proc. Natl. Acad. Sci. USA 88:7978-7982.

In one embodiment, to isolate human antibodies specific for the target antigen with the desired characteristics, a human VH and VL library are screened to select for antibody fragments having the desired specificity. The antibody libraries used in this method are preferably scFv libraries prepared and screened as described herein and in the art (McCafferty et al., PCT Publication No. WO 92/01047, McCafferty et al., (Nature 348:552-554 (1990)); and Griffiths et al., (EMBO J 12:725-734 (1993)). The scFv antibody libraries preferably are screened using target protein as the antigen.

Alternatively, the Fd fragment (VH-CH1) and light chain (VL-CL) of antibodies are separately cloned by PCR and recombined randomly in combinatorial phage display libraries, which can then be selected for binding to a particular antigen. The Fab fragments are expressed on the phage surface, i.e., physically linked to the genes that encode them. Thus, selection of Fab by antigen binding co-selects for the Fab encoding sequences, which can be amplified subsequently. Through several rounds of antigen binding and re-amplification, a procedure termed panning, Fab specific for the antigen are enriched and finally isolated.

In 1994, an approach for the humanization of antibodies, called "guided selection", was described. Guided selection utilizes the power of the phage display technique for the humanization of mouse monoclonal antibody (See Jespers, L. S., et al., Bio/Technology 12, 899-903 (1994)). For this, the Fd fragment of the mouse monoclonal antibody can be displayed in combination with a human light chain library, and the resulting hybrid Fab library may then be selected with antigen. The mouse Fd fragment thereby provides a template to guide the selection. Subsequently, the selected human light chains are combined with a human Fd fragment library. Selection of the resulting library yields entirely human Fab.

A variety of procedures have been described for deriving human antibodies from phage-display libraries (See, for example, Hoogenboom et al., J. Mol. Biol., 227:381 (1991); Marks et al., J. Mol. Biol, 222:581-597 (1991); U.S. Pat. Nos. 5,565,332 and 5,573,905; Clackson, T., and Wells, J. A., TIBTECH 12, 173-184 (1994)). In particular, in vitro selection and evolution of antibodies derived from phage display libraries has become a powerful tool (See Burton, D. R., and Barbas III, C. F., Adv. Immunol. 57, 191-280 (1994); Winter, G., et al., Annu. Rev. Immunol. 12, 433-455 (1994); U.S. patent publication no. 20020004215 and WO 92/01047; U.S. patent publication no. 20030190317; and U.S. Pat. Nos. 6,054,287 and 5,877,293.

Watkins, "Screening of Phage-Expressed Antibody Libraries by Capture Lift," Methods in Molecular Biology, Antibody Phage Display: Methods and Protocols 178:187-193 (2002), and U.S. patent publication no. 20030044772, published Mar. 6, 2003, describe methods for screening phage-expressed antibody libraries or other binding molecules by capture lift, a method involving immobilization of the candidate binding molecules on a solid support.

Fv fragments are displayed on the surface of phage, by the association of one chain expressed as a phage protein fusion (e.g., with M13 gene III) with the complementary chain expressed as a soluble fragment. It is contemplated that the phage may be a filamentous phage such as one of the class I phages: fd, M13, f1, If1, lke, ZJ/Z, Ff and one of the class II phages Xf, Pf1 and Pf3. The phage may be M13, or fd or a derivative thereof.

Once initial human VL and VH segments are selected, "mix and match" experiments, in which different pairs of the initially selected VL and VH segments are screened for target binding, are performed to select preferred VL/VH pair combinations. Additionally, to further improve the quality of the antibody, the VL and VH segments of the preferred VL/VH pair(s) can be randomly mutated, preferably within the any of the CDR1, CDR2 or CDR3 region of VH and/or VL, in a process analogous to the in vivo somatic mutation process responsible for affinity maturation of antibodies during a natural immune response. This in vitro affinity maturation can be accomplished by amplifying VL and VH regions using PCR primers complimentary to the VH CDR1, CDR2, and CDR3, or VL CDR1, CDR2, and CDR3, respectively, which primers have been "spiked" with a random mixture of the four nucleotide bases at certain positions such that the resultant PCR products encode VL and VH segments into which random mutations have been introduced into the VH and/or VL CDR3 regions. These randomly mutated VL and VH segments can be rescreened for binding to target antigen.

Following screening and isolation of an target specific antibody from a recombinant immunoglobulin display library, nucleic acid encoding the selected antibody can be recovered from the display package (e.g., from the phage genome) and subcloned into other expression vectors by standard recombinant DNA techniques. If desired, the nucleic acid can be further manipulated to create other antibody forms of the disclosure, as described below. To express a recombinant human antibody isolated by screening of a combinatorial library, the DNA encoding the antibody is cloned into a recombinant expression vector and introduced into a mammalian host cell, as described herein.

It is contemplated that the phage display method may be carried out in a mutator strain of bacteria or host cell. A mutator strain is a host cell which has a genetic defect which causes DNA replicated within it to be mutated with respect to its parent DNA. Example mutator strains are NR9046mutD5 and NR9046 mut T1.

It is also contemplated that the phage display method may be carried out using a helper phage. This is a phage which is used to infect cells containing a defective phage genome and which functions to complement the defect. The defective phage genome can be a phagemid or a phage with some function encoding gene sequences removed. Examples of helper phages are M13K07, M13K07 gene III no. 3; and phage displaying or encoding a binding molecule fused to a capsid protein.

Antibodies are also generated via phage display screening methods using the hierarchical dual combinatorial approach as disclosed in WO 92/01047 in which an individual colony containing either an H or L chain clone is used to infect a complete library of clones encoding the other chain (L or H) and the resulting two-chain specific binding member is selected in accordance with phage display techniques such as those described therein. This technique is also disclosed in Marks et al, (Bio/Technology, 10:779-783 (1992)).

Methods for display of peptides on the surface of yeast, microbial and mammalian cells have also been used to identify antigen specific antibodies. See, for example, U.S. Pat. Nos. 5,348,867; 5,723,287; 6,699,658; Wittrup, Curr Op. Biotech. 12:395-99 (2001); Lee et al, Trends in Biotech. 21(1) 45-52 (2003); Surgeeva et al, Adv. Drug Deliv. Rev. 58: 1622-54 (2006). Antibody libraries may be attached to yeast proteins, such as agglutinin, effectively mimicking the cell surface display of antibodies by B cells in the immune system.

In addition to phage display methods, antibodies may be isolated using in vitro display methods and microbial cell display, including ribosome display and mRNA display (Amstutz et al, Curr. Op. Biotech. 12: 400-05 (2001)). Selection of polypeptides using ribosome display is described in Hanes et al., (Proc. Natl Acad Sci USA, 94:4937-4942 (1997)) and U.S. Pat. Nos. 5,643,768 and 5,658,754 issued to Kawasaki. Ribosome display is also useful for rapid large scale mutational analysis of antibodies. The selective mutagenesis approach also provides a method of producing antibodies with improved activities that can be selected using ribosomal display techniques.

Amino Acid Sequence Variants

Modified polypeptide compositions comprising one, two, three, four, five, and/or six CDRs of an antibody may be generated, wherein a CDR is altered to provide increased specificity or affinity to the target molecule. Sites within antibody CDRs are typically modified in series, e.g., by substituting first with conservative choices (e.g., hydrophobic amino acid substituted for a non-identical hydrophobic amino acid) and then with more dissimilar choices (e.g., hydrophobic amino acid substituted for a charged amino acid), and then deletions or insertions may be made at the target site. For example, using the conserved framework sequences surrounding the CDRs, PCR primers complementary to these consensus sequences are generated to amplify the antigen-specific CDR sequence located between the primer regions. Techniques for cloning and expressing nucleotide and polypeptide sequences are well-established in the art [see e.g. Sambrook et al., Molecular Cloning: A Laboratory Manual, 2nd Edition, Cold Spring Harbor, N.Y. (1989)]. The amplified CDR sequences are ligated into an appropriate plasmid. The plasmid comprising one, two, three, four, five and/or six cloned CDRs optionally contains additional polypeptide encoding regions linked to the CDR.

Modifications may be made by conservative or non-conservative amino acid substitutions described in greater detail below. "Insertions" or "deletions" are preferably in the range of about 1 to 20 amino acids, more preferably 1 to 10 amino acids. The variation may be introduced by systematically making substitutions of amino acids in an antibody polypeptide molecule using recombinant DNA techniques and assaying the resulting recombinant variants for activity. Nucleic acid alterations can be made at sites that differ in the nucleic acids from different species (variable positions) or in highly conserved regions (constant regions). Methods for altering antibody sequences and expressing antibody polypeptide compositions useful in the disclosure are described in the art. See e.g., U.S. Pat. No. 8,569,462

As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

Another type of variant is an amino acid substitution variant. These variants have at least one amino acid residue in the antibody molecule removed and a different residue inserted in its place. Substitutional mutagenesis within any of the hypervariable or CDR regions or framework regions is contemplated. Conservative substitutions involve replacing an amino acid with another member of its class. Non-conservative substitutions involve replacing a member of one of these classes with a member of another class.

Conservative amino acid substitutions are made on the basis of similarity in polarity, charge, solubility, hydrophobicity, hydrophilicity, and/or the amphipathic nature of the residues involved. For example, nonpolar (hydrophobic) amino acids include alanine (Ala, A), leucine (Leu, L), isoleucine (Ile, I), valine (Val, V), proline (Pro, P), phenylalanine (Phe, F), tryptophan (Trp, W), and methionine (Met, M); polar neutral amino acids include glycine (Gly, G), serine (Ser, S), threonine (Thr, T), cysteine (Cys, C), tyrosine (Tyr, Y), asparagine (Asn, N), and glutamine (Gln, Q); positively charged (basic) amino acids include arginine (Arg, R), lysine (Lys, K), and histidine (His, H); and negatively charged (acidic) amino acids include aspartic acid (Asp, D) and glutamic acid (Glu, E).

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

Altered Glycosylation

Antibody variants can also be produced that have a modified glycosylation pattern relative to the parent antibody, for example, deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. The presence of either of these tripeptide sequences in a polypeptide creates a potential glycosylation site. Thus, N-linked glycosylation sites may be added to an antibody by altering the amino acid sequence such that it contains one or more of these tripeptide sequences. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. O-linked glycosylation sites may be added to an antibody by inserting or substituting one or more serine or threonine residues to the sequence of the original antibody.

Fc glycans influence the binding of IgG to Fc receptors and C1q, and are therefore important for IgG effector functions. Antibody variants with modified Fc glycans and altered effector function may be produced. For example, antibodies with modified terminal sugars such as sialic acids, core fucose, bisecting N-acetylglucosamine, and mannose residues may have altered binding to the FcγRIIIa receptor and altered ADCC activity. In a further example, antibodies with modified terminal galactose residues may have altered binding to C1q and altered CDC activity (Raju, Curr. Opin. Immunol. 20: 471-78 (2008).

Also contemplated for use in the methods are antibody molecules with absent or reduced fucosylation that exhibit improved ADCC activity. A variety of ways are known in the art to accomplish this. For example, ADCC effector activity is mediated by binding of the antibody molecule to the FcγRIII receptor, which has been shown to be dependent on the carbohydrate structure of the N-linked glycosylation at the Asn-297 of the CH2 domain. Non-fucosylated antibodies bind this receptor with increased affinity and trigger FcγRIII-mediated effector functions more efficiently than native, fucosylated antibodies. For example, recombinant production of non-fucosylated antibody in CHO cells in which the alpha-1,6-fucosyl transferase enzyme has been knocked out results in antibody with 100-fold increased ADCC activity (Yamane-Ohnuki et al., Biotechnol Bioeng. 87:614-22 (2004)). Similar effects can be accomplished through decreasing the activity of this or other enzymes in the fucosylation pathway, e.g., through siRNA or antisense RNA treatment, engineering cell lines to knockout the enzyme(s), or culturing with selective glycosylation inhibitors (Rothman et al., Mol Immunol. 26:1113-23 (1989)). Some host cell strains, e.g. Lec13 or rat hybridoma YB2/0 cell line naturally produce antibodies with lower fucosylation levels. (Shields et al., J Biol Chem. 277:26733-40 (2002); Shinkawa et al., J Biol Chem. 278:3466-73 (2003)). An increase in the level of bisected carbohydrate, e.g. through recombinantly producing antibody in cells that overexpress GnTIII enzyme, has also been determined to increase ADCC activity (Umana et al., Nat Biotechnol. 17:176-80 (1999)). It has been predicted that the absence of only one of the two fucose residues may be sufficient to increase ADCC activity (Ferrara et al., Biotechnol Bioeng. 93:851-61 (2006)).

Variants with Altered Effector Function

Other modifications of the antibodies for use in the methods are contemplated. In one aspect, it may be desirable to modify an antibody used herein with respect to effector function, for example, to enhance the effectiveness of the antibody in treating cancer. One method for modifying effector function teaches that cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., (J. Exp Med. 176: 1191-1195 (1992)) and Shopes, B. (J. Immunol. 148: 2918-2922 (1992)). Homodimeric antibodies with enhanced anti-tumor activity may also be prepared using heterobifunctional cross-linkers as described in Wolff et al., (Cancer Research 53: 2560-2565 (1993)). Alternatively, an antibody can be engineered which has dual Fc regions and may thereby have enhanced complement lysis and ADCC capabilities. See Stevenson et al., (Anti-Cancer Drug Design 3: 219-230 (1989)). In addition, it has been shown that sequences within the CDR can cause an antibody to bind to MHC Class II and trigger an unwanted helper T-cell response. A conservative substitution can allow the antibody to retain binding activity yet lose its ability to trigger an unwanted T-cell response.

In certain embodiments of the present disclosure, it may be desirable to use an antibody fragment, rather than an intact antibody, to increase tumor penetration, for example. In this case, it may be desirable to modify the antibody fragment in order to increase its serum half-life, for example, adding molecules such as PEG or other water soluble polymers, including polysaccharide polymers, to antibody fragments to increase the half-life.

The salvage receptor binding epitope preferably constitutes a region wherein any one or more amino acid residues from one or two loops of a Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CH1, CH3, or VH region, or more than one such region, of the antibody. Alternatively, the epitope is taken from the CH2 domain of the Fc region and transferred to the CL region or VL region, or both, of the antibody fragment.

Thus, antibodies of the present disclosure may comprise a human Fc portion, a human consensus Fc portion, or a variant thereof that retains the ability to interact with the Fc salvage receptor, including variants in which cysteines involved in disulfide bonding are modified or removed, and/or in which the a met is added at the N-terminus and/or one or more of the N-terminal 20 amino acids are removed, and/or regions that interact with complement, such as the C1q binding site, are removed, and/or the ADCC site is removed [see, e.g., Sarmay et al., Molec. Immunol. 29:633-9 (1992)].

Shields et al. reported that IgG1 residues involved in binding to all human Fc receptors are located in the CH2 domain proximal to the hinge and fall into two categories as follows: 1) positions that may interact directly with all FcR include Leu234-Pro238, Ala327, and Pro329 (and possibly Asp265); 2) positions that influence carbohydrate nature or position include Asp265 and Asn297. The additional IgG1 residues that affected binding to Fc receptor II are as follows: (largest effect) Arg255, Thr256, Glu258, Ser267, Asp270, Glu272, Asp280, Arg292, Ser298, and (less effect) His268, Asn276, His285, Asn286, Lys290, Gln295, Arg301, Thr307, Leu309, Asn315, Lys322, Lys326, Pro331, Ser337, Ala339, Ala378, and Lys414. A327Q, A327S, P329A, D265A and D270A reduced binding. In addition to the residues identified above for all FcR, additional IgG1 residues that reduced binding to Fc receptor IIIA by 40% or more are as follows: Ser239, Ser267 (Gly only), His268, Glu293, Gln295, Tyr296, Arg301, Val303, Lys338, and Asp376. Variants that improved binding to FcRIIIA include T256A, K290A, S298A, E333A, K334A, and A339T. Lys414 showed a 40% reduction in binding for FcRIIA and FcRIIB, Arg416 a 30% reduction for FcRIIA and FcRIIIA, Gln419 a 30% reduction to FcRIIA and a 40% reduction to FcRIIB, and Lys360 a 23% improvement to FcRIIIA See also Presta et al., (Biochem. Soc. Trans. 30:487-490, 2001), incorporated herein by reference in its entirety, which described several positions in the Fc region of IgG1 were found which improved binding only to specific Fc gamma receptors (R) or simultaneously improved binding to one type of Fc gamma R and reduced binding to another type. Selected IgG1 variants with improved binding to Fc gamma RIIIa were then tested in an in vitro antibody-dependent cellular cytotoxicity (ADCC) assay and showed an enhancement in ADCC when either peripheral blood mononuclear cells or natural killer cells were used.

For example, U.S. Pat. No. 6,194,551, incorporated herein by reference in its entirety, describes variants with altered effector function containing mutations in the human IgG Fc region, at amino acid position 329, 331 or 322 (using Kabat numbering), some of which display reduced C1q binding or CDC activity. As another example, U.S. Pat. No. 6,737,056, incorporated herein by reference in its entirety, describes variants with altered effector or Fc-gamma-receptor binding containing mutations in the human IgG Fc region, at amino acid position 238, 239, 248, 249, 252, 254, 255, 256, 258, 265, 267, 268, 269, 270, 272, 276, 278, 280, 283, 285, 286, 289, 290, 292, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439 (using Kabat numbering), some of which display receptor binding profiles associated with reduced ADCC or CDC activity. Of these, a mutation at amino acid position 238, 265, 269, 270, 327 or 329 are stated to reduce binding to FcRI, a mutation at amino acid position 238, 265, 269, 270, 292, 294, 295, 298, 303, 324, 327, 329, 333, 335, 338, 373, 376, 414, 416, 419, 435, 438 or 439 are stated to reduce binding to FcRII, and a mutation at amino acid position 238, 239, 248, 249, 252, 254, 265, 268, 269, 270, 272, 278, 289, 293, 294, 295, 296, 301, 303, 322, 327, 329, 338, 340, 373, 376, 382, 388, 389, 416, 434, 435 or 437 is stated to reduce binding to FcRIII U.S. Pat. No. 5,624,821, incorporated by reference herein in its entirety, reports that C1q binding activity of an murine antibody can be altered by mutating amino acid residue 318, 320 or 322 of the heavy chain and that replacing residue 297 (Asn) results in removal of lytic activity.

U.S. Patent Publication No. 20040132101, incorporated by reference herein in its entirety, describes variants with mutations at amino acid positions 240, 244, 245, 247, 262, 263, 266, 299, 313, 325, 328, or 332 (using Kabat numbering) or positions 234, 235, 239, 240, 241, 243, 244, 245, 247, 262, 263, 264, 265, 266, 267, 269, 296, 297, 298, 299, 313, 325, 327, 328, 329, 330, or 332 (using Kabat numbering), of which mutations at positions 234, 235, 239, 240, 241, 243, 244, 245, 247, 262, 263, 264, 265, 266, 267, 269, 296, 297, 298, 299, 313, 325, 327, 328, 329, 330, or 332 may reduce ADCC activity or reduce binding to an Fc gamma receptor.

Covalent Modifications

Antibodies comprising covalent modifications are also contemplated for use in the methods. They may be made by chemical synthesis or by enzymatic or chemical cleavage of the antibody, if applicable. Other types of covalent modifications of the antibody are introduced into the molecule by reacting targeted amino acid residues of the antibody with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Other modifications include histidlyl, lysinyl arginyl, tyrosyl, glutaminyl and asparaginyl hydroxylation of proline and lysine. Methods for making such modifications are disclosed in U.S. Pat. No. 8,926,976, incorporated herein by reference, and in the art.

Carboxyl side groups (aspartyl or glutamyl) are selectively modified by reaction with carbodiimides (R-N.dbd.C.dbd.N-R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO87/05330 and in Aplin and Wriston, (CRC Crit. Rev. Biochem., pp. 259-306 (1981)).

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Hakimuddin, et al., (Arch. Biochem. Biophys. 259: 52 (1987)) and by Edge et al., (Anal. Biochem. 118: 131 (1981)). Enzymatic cleavage of carbohydrate moieties on antibodies can be achieved by the use of a variety of endo- and exo-glycosidases as described by Thotakura et al., (Meth. Enzymol. 138: 350 (1987)).

Another type of covalent modification of the antibody comprises linking the antibody to one of a variety of nonproteinaceous polymers, e.g., polyethylene glycol, polypropylene glycol, polyoxyethylated polyols, polyoxyethylated sorbitol, polyoxyethylated glucose, polyoxyethylated glycerol, polyoxyalkylenes, or polysaccharide polymers such as dextran. Such methods are known in the art.

Derivatives

As stated above, derivative, when used in connection with antibody substances and polypeptides, refers to polypeptides chemically modified by such techniques as ubiquitination, labeling (e.g., with radionuclides or various enzymes), covalent polymer attachment such as PEGylation (derivatization with polyethylene glycol) and insertion or substitution by chemical synthesis of amino acids such as ornithine. Derivatives of the antibodies disclosed herein are also useful as therapeutic agents and may be used in the methods herein.

The conjugated moiety can be incorporated in or attached to an antibody substance either covalently, or through ionic, van der Waals or hydrogen bonds, e.g., incorporation of radioactive nucleotides, or biotinylated nucleotides that are recognized by streptavadin.

Polyethylene glycol (PEG) may be attached to the antibody substances to provide a longer half-life in vivo. The PEG group may be of any convenient molecular weight and may be linear or branched. The average molecular weight of the PEG will preferably range from about 2 kiloDalton ("kD") to about 100 kDa, more preferably from about 5 kDa to about 50 kDa, most preferably from about 5 kDa to about 10 kDa. The PEG groups will generally be attached to the antibody substances of the disclosure via acylation or reductive alkylation through a natural or engineered reactive group on the PEG moiety (e.g., an aldehyde, amino, thiol, or ester group) to a reactive group on the antibody substance (e.g., an aldehyde, amino, or ester group). Addition of PEG moieties to antibody substances can be carried out using techniques well-known in the art. See, e.g., International Publication No. WO 96/11953 and U.S. Pat. No. 4,179,337.

Ligation of the antibody substance with PEG usually takes place in aqueous phase and can be easily monitored by reverse phase analytical HPLC. The PEGylated substances are purified by preparative HPLC and characterized by analytical HPLC, amino acid analysis and laser desorption mass spectrometry.

Antibody Conjugates

An antibody may be administered in its "naked" or unconjugated form, or may be conjugated directly to other therapeutic or diagnostic agents, or may be conjugated indirectly to carrier polymers comprising such other therapeutic or diagnostic agents. In some embodiments the antibody is conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate). Suitable chemotherapeutic agents include: daunomycin, doxorubicin, methotrexate, and vindesine (Rowland et al., (1986) supra). Suitable toxins include: bacterial toxins such as diphtheria toxin; plant toxins such as ricin; small molecule toxins such as geldanamycin (Mandler et al J. Natl. Cancer Inst. 92(19): 1573-81 (2000); Mandler et al., Bioorg. Med. Chem. Letters 10:1025-1028 (2000); Mandler et al., Bioconjugate Chem. 13.786-91 (2002)), maytansinoids (EP 1391213; Liu et al., Proc. Natl. Acad. Sci. USA 93:8618-23 (1996)), auristatins (Doronina et al., Nat. Biotech. 21: 778-84 (2003) and calicheamicin (Lode et al., Cancer Res. 58:2928 (1998); Hinman et al., Cancer Res. 53:3336-3342 (1993)). Antibody-Drug Conjugates and methods are reviewed in Ducry L, mAbs. 6(1), 2014 and Shen W C, AAPS., 17: 3-7, 2015.

Antibodies can be detectably labeled through the use of radioisotopes, affinity labels (such as biotin, avidin, etc.), enzymatic labels (such as horseradish peroxidase, alkaline phosphatase, etc.) fluorescent or luminescent or bioluminescent labels (such as FITC or rhodamine, etc.), paramagnetic atoms, and the like. Procedures for accomplishing such labeling are well known in the art; for example, see (Sternberger, L. A. et al., J. Histochem. Cytochem. 18:315 (1970); Bayer, E. A. et al., Meth. Enzym. 62:308 (1979); Engval, E. et al., Immunol. 109:129 (1972); Goding, J. W. J. Immunol. Meth. 13:215 (1976)).

Conjugation of antibody moieties is described in U.S. Pat. No. 6,306,393. General techniques are also described in Shih et al., Int. J. Cancer 41:832-839 (1988); Shih et al., Int. J. Cancer 46:1101-1106 (1990); and Shih et al., U.S. Pat. No. 5,057,313. This general method involves reacting an antibody component having an oxidized carbohydrate portion with a carrier polymer that has at least one free amine function and that is loaded with a plurality of drug, toxin, chelator, boron addends, or other therapeutic agent. This reaction results in an initial Schiff base (imine) linkage, which can be stabilized by reduction to a secondary amine to form the final conjugate.

The carrier polymer may be, for example, an aminodextran or polypeptide of at least 50 amino acid residues. Various techniques for conjugating a drug or other agent to the carrier polymer are known in the art. A polypeptide carrier can be used instead of aminodextran, but the polypeptide carrier should have at least 50 amino acid residues in the chain, preferably 100-5000 amino acid residues. At least some of the amino acids should be lysine residues or glutamate or aspartate residues. The pendant amines of lysine residues and pendant carboxylates of glutamine and aspartate are convenient for attaching a drug, toxin, immunomodulator, chelator, boron addend or other therapeutic agent. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier and conjugate. Examples of agents to which the antibody can be conjugated include any of the cytotoxic or chemotherapeutic agents described herein.

Alternatively, conjugated antibodies can be prepared by directly conjugating an antibody component with a therapeutic agent. The general procedure is analogous to the indirect method of conjugation except that a therapeutic agent is directly attached to an oxidized antibody component. For example, a carbohydrate moiety of an antibody can be attached to polyethyleneglycol to extend half-life.

Alternatively, a therapeutic agent can be attached at the hinge region of a reduced antibody component via disulfide bond formation, or using a heterobifunctional cross-linker, such as N-succinyl 3-(2-pyridyldithio)proprionate (SPDP). Yu et al., Int. J. Cancer 56:244 (1994). General techniques for such conjugation are well-known in the art. See, for example, Wong, Chemistry Of Protein Conjugation and Cross-Linking (CRC Press 1991); Upeslacis et al., "Modification of Antibodies by Chemical Methods," in Monoclonal Antibodies: Principles and Applications, Birch et al. (eds.), pages 187-230 (Wiley-Liss, Inc. 1995); Price, "Production and Characterization of Synthetic Peptide-Derived Antibodies," in Monoclonal Antibodies: Production, Engineering and Clinical Application, Ritter et al. (eds.), pages 60-84 (Cambridge University Press 1995). A variety of bifunctional protein coupling agents are known in the art, such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

Antibody Fusion Proteins

Methods of making antibody-toxin fusion proteins in which a recombinant molecule comprises one or more antibody components and a toxin or chemotherapeutic agent also are known to those of skill in the art. For example, antibody-*Pseudomonas* exotoxin A fusion proteins have been described by Chaudhary et al., Nature 339:394 (1989), Brinkmann et al., Proc. Nat'l Acad. Sci. USA 88:8616 (1991), Batra et al., Proc. Nat'l Acad. Sci. USA 89:5867 (1992), Friedman et al., J. Immunol. 150:3054 (1993), Wels et al., Int. J. Can. 60:137 (1995), Fominaya et al., J. Biol.

Chem. 271:10560 (1996), Kuan et al., Biochemistry 35:2872 (1996), and Schmidt et al., Int. J. Can. 65:538 (1996). Antibody-toxin fusion proteins containing a diphtheria toxin moiety have been described by Kreitman et al., Leukemia 7:553 (1993), Nicholls et al., J. Biol. Chem. 268:5302 (1993), Thompson et al., J. Biol. Chem. 270: 28037 (1995), and Vallera et al., Blood 88:2342 (1996). Deonarain et al., Tumor Targeting 1:177 (1995), have described an antibody-toxin fusion protein having an RNase moiety, while Linardou et al., Cell Biophys. 24-25:243 (1994), produced an antibody-toxin fusion protein comprising a DNase I component. Gelonin was used as the toxin moiety in the antibody-toxin fusion protein of Wang et al., Abstracts of the 209th ACS National Meeting, Anaheim, Calif., Apr. 2-6, 1995, Part 1, BIOT005. As a further example, Dohlsten et al., Proc. Nat'l Acad. Sci. USA 91:8945 (1994), reported an antibody-toxin fusion protein comprising Staphylococcal enterotoxin-A.

Illustrative of toxins which are suitably employed in the preparation of such fusion proteins are ricin, abrin, ribonuclease, DNase I, Staphylococcal enterotoxin-A, pokeweed antiviral protein, gelonin, diphtherin toxin, *Pseudomonas* exotoxin, and *Pseudomonas* endotoxin. See, for example, Pastan et al., Cell 47:641 (1986), and Goldenberg, C A—A Cancer Journal for Clinicians 44:43 (1994). Other suitable toxins are known to those of skill in the art.

Antibodies of the present disclosure may also be used in ADEPT by conjugating the antibody to a prodrug-activating enzyme which converts a prodrug (e.g., a peptidyl chemotherapeutic agent, See WO81/01145) to an active anti-cancer drug. See, for example, WO88/07378 and U.S. Pat. No. 4,975,278.

The enzyme component of the immunoconjugate useful for ADEPT includes any enzyme capable of acting on a prodrug in such a way so as to convert it into its more active, cytotoxic form.

Enzymes that are useful in the present disclosure include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as α-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as abzymes, can be used to convert the prodrugs of the disclosure into free active drugs (See, e.g., Massey, Nature 328: 457-458 (1987). Antibody-abzyme conjugates can be prepared as described herein for delivery of the abzyme to a tumor cell population.

The enzymes above can be covalently bound to the antibodies by techniques well known in the art such as the use of the heterobifunctional crosslinking reagents discussed above. Alternatively, fusion proteins comprising at least the antigen binding region of an antibody of the disclosure linked to at least a functionally active portion of an enzyme of the disclosure can be constructed using recombinant DNA techniques well known in the art (See, e.g., Neuberger et al., Nature 312:604-608 (1984)).

Recombinant Production of Antibodies

DNA encoding an antibody described herein may be isolated and sequenced using conventional procedures (e.g., by using oligonucleotide probes that are capable of binding specifically to genes encoding the heavy and light chains of the antibodies). Usually this requires cloning the DNA or, preferably, mRNA (i.e., cDNA) encoding the antibodies. Cloning and sequencing is carried out using standard techniques, such as for example polymerase chain reaction (PCR), (see, e.g., Sambrook et al. (1989) Molecular Cloning: A Laboratory Guide, Vols 1-3, Cold Spring Harbor Press; Ausubel, et al. (Eds.), Protocols in Molecular Biology, John Wiley & Sons (1994)), which are incorporated herein by reference).

Sequencing is carried out using standard techniques (see, e.g., Sambrook et al. (1989) Molecular Cloning: A Laboratory Guide, Vols 1-3, Cold Spring Harbor Press, and Sanger, F. et al. (1977) Proc. Natl. Acad. Sci. USA 74: 5463-5467, which is incorporated herein by reference). By comparing the sequence of the cloned nucleic acid with published sequences of human immunoglobulin genes and cDNAs, one of skill will readily be able to determine, depending on the region sequenced, (i) the germline segment usage of the immunoglobulin polypeptide (including the isotype of the heavy chain) and (ii) the sequence of the heavy and light chain variable regions, including sequences resulting from N-region addition and the process of somatic mutation. One source of immunoglobulin gene sequence information is the National Center for Biotechnology Information, National Library of Medicine, National Institutes of Health, Bethesda, Md.

Once isolated, the DNA may be placed into expression vectors, which are then transfected into host cells such as *E. coli* cells, simian COS cells, human embryonic kidney 293 cells (e.g., 293E cells), Chinese hamster ovary (CHO) cells, or myeloma cells that do not otherwise produce immunoglobulin protein, to obtain the synthesis of monoclonal antibodies in the recombinant host cells. Recombinant production of antibodies is well known in the art.

In an alternative embodiment, the amino acid sequence of an immunoglobulin of interest may be determined by direct protein sequencing. Suitable encoding nucleotide sequences can be designed according to a universal codon table.

For recombinant production of the antibodies, the nucleic acid encoding it is isolated and inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more selective marker genes, an enhancer element, a promoter, and a transcription termination sequence, which are known and described in the art.

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41 P disclosed in DD 266,710 published Apr. 12, 1989), *Pseudomonas* such as *P. aeruginosa*, and

*Streptomyces.* One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastors* (EP 183,070); *Candida; Trichoderma reesia* (EP 244,234); *Neurospora crassa; Schwanniomyces* such as *Schwanniomyces occidentalis;* and filamentous fungi such as, e.g., *Neurospora, Penicillium, Tolypocladium,* and *Aspergillus* hosts such as *A. nidulans* and *A. niger.*

Suitable host cells for the expression of glycosylated antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present disclosure, particularly for transfection of *Spodoptera frugiperda* cells.

Plant cell cultures of cotton, corn, potato, soybean, *petunia*, tomato, tobacco, *lemna*, and other plant cells can also be utilized as hosts.

Examples of useful mammalian host cell lines are Chinese hamster ovary cells, including CHOK1 cells (ATCC CCL61), DXB-11, DG-44, and Chinese hamster ovary cells/-DHFR (CHO, Urlaub et al., Proc. Natl. Acad. Sci. USA 77: 4216 (1980)); monkey kidney CV1 line transformed by SV40 (COS-7, ATCC CRL 1651); human embryonic kidney line (293 or 293 cells subcloned for growth in suspension culture, (Graham et al., J. Gen Virol. 36: 59, 1977); baby hamster kidney cells (BHK, ATCC CCL 10); mouse sertoli cells (TM4, Mather, (Biol. Reprod. 23: 243-251, 1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y Acad. Sci. 383: 44-68 (1982)); MRC 5 cells; FS4 cells; and a human hepatoma line (Hep G2).

Host cells are transformed or transfected with the above-described expression or cloning vectors for antibody production and cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful and preferred for the expression of antibodies that bind target.

When using recombinant techniques, the antibody can be produced intracellularly, in the periplasmic space, or directly secreted into the medium, including from microbial cultures. If the antibody is produced intracellularly, as a first step, the particulate debris, either host cells or lysed fragments, is removed, for example, by centrifugation or ultrafiltration. Better et al. (Science 240:1041-43, 1988; ICSU Short Reports 10:105 (1990); and Proc. Natl. Acad. Sci. USA 90:457-461 (1993) describe a procedure for isolating antibodies which are secreted to the periplasmic space of *E. coli.* [See also, (Carter et al., Bio/Technology 10:163-167 (1992)].

The antibody composition prepared from microbial or mammalian cells can be purified using, for example, hydroxylapatite chromatography cation or avian exchange chromatography, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Meth. 62: 1-13, 1983). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH 3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE® chromatography on an anion or cation exchange resin (such as a polyaspartic acid column), chromatofocusing, SDS-PAGE, and ammonium sulfate precipitation are also available depending on the antibody to be recovered.

Screening Methods

Effective therapeutics depend on identifying efficacious agents devoid of significant toxicity. Antibodies may be screened for binding affinity by methods known in the art. For example, gel-shift assays, Western blots, radiolabeled competition assay, co-fractionation by chromatography, co-precipitation, cross linking, ELISA, and the like may be used, which are described in, for example, Current Protocols in Molecular Biology (1999) John Wiley & Sons, NY, which is incorporated herein by reference in its entirety.

Methods for assessing neutralizing biological activity of TGFβ and anti-TGFβ antibodies are known in the art. See, e.g., U.S. Pat. No. 7,867,496. Examples of in vitro bioassays include: (1) induction of colony formation of NRK cells in soft agar in the presence of EGF (Roberts et al. (1981) Proc. Natl. Acad. Sci. USA, 78:5339-5343); (2) induction of differentiation of primitive mesenchymal cells to express a cartilaginous phenotype (Seyedin et al. (1985) Proc. Natl. Acad. Sci. USA, 82:2267-2271); (3) inhibition of growth of Mv1Lu mink lung epithelial cells (Danielpour et al. (1989) J. Cell. Physiol., 138:79-86) and BBC-1 monkey kidney cells (Holley et al. (1980) Proc. Natl. Acad. Sci. USA, 77:5989-5992); (4) inhibition of mitogenesis of C3H/HeJ mouse thymocytes (Wrann et al. (1987) EMBO J., 6:1633-1636); (5) inhibition of differentiation of rat L6 myoblast cells (Florini et al. (1986) J. Biol. Chem., 261:16509-16513); (6) measurement of fibronectin production (Wrana et al. (1992) Cell, 71:1003-1014); (7) induction of plasminogen activator inhibitor I (PAI-1) promoter fused to a luciferase reporter gene (Abe et al. (1994) Anal. Biochem., 216:276-284); (8) sandwich enzyme-linked immunosorbent assays (Danielpour et al. (1989) Growth Factors, 2:61-71); and (9) cellular assays described in Singh et al. (2003) Bioorg. Med. Chem. Lett., 13(24):4355-4359.

In some embodiments, antibody neutralization of TGFβ1 and TGFβ2 is at least 2-50 fold, 10-100 fold, 2-fold, 5-fold, 10-fold, 25-fold, 50-fold or 100-fold, or 20-50%, 50-100%, 20%, 25%, 30%, 40%, 50%, 60%, 70%, 80%, 90% or 100% more potent that neutralization of TGFβ3.

Additional methods for assessing the biological activity and neutralization of TGFβ (e.g., by TGFβ antibodies) are known in the art. For example, neutralization can be measured by neutralization assays and expressed as an IC50 value. The IC50 value can be calculated for a given molecule by determining the concentration of molecule needed to elicit half inhibition of the maximum biological response of a second molecule or cell activity. The lower the IC50, the greater the potency of the molecule to inhibit the desired protein activity. Exemplary neutralization assays contemplated herein include, but are not limited to, an interleukin-11 release assay and an HT-2/IL-4 cell proliferation assay. In addition, a TGFβ activity assay can be carried out to determine if the antibody inhibits one TGFβ isoform preferentially, including a pSMAD phosphorylation assay or an rhLAP binding assay.

Methods for assessing neutralizing biological activity of PD-1 inhibitors and anti-PD-1 antibodies are known in the art. For example, neutralization can be measured by neutralization assays and expressed as an IC50 value. The IC50 value can be calculated for a given molecule by determining the concentration of molecule needed to elicit half inhibition of the maximum biological response of a second molecule or cell activity. The lower the IC50, the greater the potency of the molecule to inhibit the desired protein activity. Exemplary neutralization assays contemplated herein include, but are not limited to, measuring the PD-1 antibodies ability to promote T-cell responses in human T cells, IFNγ release assay, or interleukin-2 secretion assay (Wang et al., Cancer Immunol Res., 2(9): 846-56 (2014).

Combination Therapy

A TGFβ inhibitor of the present disclosure is administered with a second agent that inhibits PD-1 and the combination is useful to treat a disease or disorder as described herein. In the case of the use of antibodies to inhibit TGFβ and PD-1, if more than one TGFβ antibody or PD-1 antibody is effective at binding to respective target antigens, it is contemplated that two or more antibodies to different epitopes of the target antigen and/or which bind preferentially to different isoforms of TGFβ or PD-1 may be mixed such that the combination of antibodies, three or four or more together provide still further improved efficacy against a condition or disorder to be treated with inhibitors of TGFβ and PD-1. Compositions comprising one or more antibody of the invention may be administered to persons or mammals suffering from, or predisposed to suffer from, a condition or disorder associated with the target polypeptide of either TGFβ or PD-1.

Concurrent administration of two therapeutic agents does not require that the agents be administered at the same time or by the same route, as long as there is an overlap in the time period during which the agents are exerting their therapeutic effect. Simultaneous or sequential administration is contemplated, as is administration on different days or weeks.

A third agent may also be used with an inhibitor of TGFβ and an inhibitor PD-1. The third agent may be other therapeutic agents, such as cytokines, growth factors, other inhibitors and antibodies to other target antigens, for example ipilimumab (YERVOY®, Bristol-Myers Squibb Company), an antibody to CTLA-4; bevacizumab (AVASTIN®, Genentech), an antibody to VEGF-A; erlotinib (TARCEVA®, Genentech and OSI Pharmaceuticals), a tyrosine kinase inhibitor which acts on EGFR, dasatinib (SPRYCEL®, Bristol-Myers Squibb Company), an oral Bcr-Abl tyrosone kinase inhibitor; IL-21; pegylated IFN-α2b; axitinib (INLYTA®, Pfizer, Inc.), a tyrosine kinase inhibitor; and trametinib (MEKINIST®, GlaxoSmithKline), a MEK inhibitor (Philips and Atkins, Int Immunol., 27(1):39-46 (2015) which is incorporated herein by reference).

If the cancer is V600 mutation positive, as is the case for some cancers, in particular in melanoma (Ascierto P et al., J Transl Med., 10: 85, 2012) it is also contemplated that the third agent is BRAF inhibitor, for example vemurafenib or dabrafenib.

It is contemplated the inhibitors, such as antibodies, of the present disclosure may be given simultaneously, in the same formulation. It is further contemplated that the inhibitors are administered in a separate formulation and administered concurrently, with concurrently referring to agents given within 30 minutes of each other. It is further contemplated that the third agent may be given simultaneously with the inhibitors.

In another aspect, a TGFβ or a PD-1 inhibitor is administered prior to administration of the other inhibitor composition. Prior administration refers to administration of an inhibitor within the range of one week prior to treatment with the other inhibitor, up to 30 minutes before administration of the other inhibitor. It is further contemplated that an inhibitor is administered subsequent to administration of another inhibitor composition. Subsequent administration is meant to describe administration from 30 minutes after antibody treatment up to one week after antibody administration. It is further contemplated that a third agent maybe administered in this manner prior to either the TGFβ inhibitor or PD-1 inhibitor.

It is further contemplated that other adjunct therapies may be administered, where appropriate. For example, the patient may also be administered surgical therapy, chemotherapy, a cytotoxic agent, photodynamic therapy or radiation therapy where appropriate.

It is further contemplated that when the inhibitors or antibodies herein are administered in combination with a third agent, such as for example, wherein the third agent is a cytokine or growth factor, or a chemotherapeutic agent, the administration also includes use of a radiotherapeutic agent or radiation therapy. The radiation therapy administered in combination with an antibody composition is administered as determined by the treating physician, and at doses typically given to patients being treated for cancer.

A cytotoxic agent refers to a substance that inhibits or prevents the function of cells and/or causes destruction of cells. The term is intended to include radioactive isotopes (e.g., I131, I125, Y90 and Re186), chemotherapeutic agents, and toxins such as enzymatically active toxins of bacterial, fungal, plant or animal origin or synthetic toxins, or fragments thereof. A non-cytotoxic agent refers to a substance that does not inhibit or prevent the function of cells and/or does not cause destruction of cells. A non-cytotoxic agent may include an agent that can be activated to be cytotoxic. A non-cytotoxic agent may include a bead, liposome, matrix or particle (see, e.g., U.S. Patent Publications 2003/0028071 and 2003/0032995 which are incorporated by reference herein). Such agents may be conjugated, coupled, linked or associated with an antibody according to the disclosure.

Chemotherapeutic agents contemplated for use with the antibodies of the present disclosure include, but are not limited to those listed in Table I:

TABLE I

Alkylating agents
Nitrogen mustards
mechlorethamine
cyclophosphamide
ifosfamide
melphalan
chlorambucil
Nitrosoureas
carmustine (BCNU)
lomustine (CCNU)
semustine (methyl-CCNU)
Ethylenimine/Methyl-melamine
thriethylenemelamine (TEM)
triethylene thiophosphoramide (thiotepa)
hexamethylmelamine (HMM, altretamine)
Alkyl sulfonates
busulfan
Triazines
dacarbazine (DTIC)
Antimetabolites
Folic Acid analogs
methotrexate
Trimetrexate
Pemetrexed
(Multi-targeted antifolate)
Pyrimidine analogs
5-fluorouracil
fluorodeoxyuridine
gemcitabine
cytosine arabinoside
(AraC, cytarabine)
5-azacytidine
2,2'-difluorodeoxy-cytidine
Purine analogs
6-mercaptopurine
6-thioguanine
azathioprine
2'-deoxycoformycin (pentostatin)
erythrohydroxynonyl-adenine (EHNA)
fludarabine phosphate
2-chlorodeoxyadenosine
(cladribine, 2-CdA)
Type I Topoisomerase Inhibitors
camptothecin
topotecan
irinotecan
Biological response modifiers
G-CSF
GM-CSF
Differentiation Agents
retinoic acid derivatives
Hormones and antagonists
Adrenocorticosteroids/antagonists
prednisone and equivalents
dexamethasone
ainoglutethimide
Progestins
hydroxyprogesterone caproate
medroxyprogesterone acetate
megestrol acetate
Estrogens
diethylstilbestrol
ethynyl estradiol/equivalents
Antiestrogen
tamoxifen
Androgens
testosterone propionate
fluoxymesterone/equivalents TABLE I-continued Antiandrogens
flutamide
gonadotropin-releasing
hormone analogs
leuprolide
Nonsteroidal antiandrogens
flutamide
Natural products
Antimitotic drugs
Taxanes
paclitaxel
Vinca alkaloids
vinblastine (VLB)
vincristine
vinorelbine
Taxotere ® (docetaxel)
estramustine
estramustine phosphate
Epipodophylotoxins
etoposide
teniposide
Antibiotics
actimomycin D
daunomycin (rubido-mycin)
doxorubicin (adria-mycin)
mitoxantroneidarubicin
bleomycin
splicamycin (mithramycin)
mitomycinC
dactinomycin
aphidicolin
Enzymes
L-asparaginase
L-arginase
Radiosensitizers
metronidazole
misonidazole
desmethylmisonidazole
pimonidazole
etanidazole
nimorazole
RSU 1069
EO9
RB 6145
SR4233
nicotinamide
5-bromodeozyuridine
5-iododeoxyuridine
bromodeoxycytidine
Miscellaneous agents
Platinum coordination complexes
cisplatin
Carboplatin
oxaliplatin
Anthracenedione
mitoxantrone
Substituted urea
hydroxyurea
Methylhydrazine derivatives
N-methylhydrazine (MIH)
procarbazine
Adrenocortical suppressant
mitotane (o,p'-DDD)
ainoglutethimide
Cytokines
interferon ($\alpha$, $\beta$, $\gamma$)
interleukin-2
Photosensitizers
hematoporphyrin derivatives
Photofrin ®
benzoporphyrin derivatives
Npe6
tin etioporphyrin (SnET2)
pheoboride-a
bacteriochlorophyll-a
naphthalocyanines
phthalocyanines
zinc phthalocyanines
Radiation
X-ray TABLE I-continued ultraviolet light
gamma radiation
visible light
infrared radiation
microwave radiation Treatment of Disorders In another embodiment, any of the types of inhibitors described herein may be used in the methods. In exemplary embodiments, the target specific antibody is a human, chimeric or humanized antibody. In another exemplary embodiment, the target is human and the patient is a human patient. Alternatively, the patient may be a mammal that expresses a target protein that target specific antibody cross-reacts with. The antibody may be administered to a non-human mammal expressing a target protein with which the antibody cross-reacts (i.e. a primate) for veterinary purposes or as an animal model of human disease. Such animal models may be useful for evaluating the therapeutic efficacy of target specific antibodies of the disclosure (Huang and Balmain, Cold Spring Harb Perspect Med., 4(9):a013623,2014).

In one embodiment, the disclosure provides a method for treating cancer or preventing the recurrence of cancer comprising administering to a subject in need thereof a therapeutically effective amount of a TGFβ inhibitor and a PD-1 inhibitor or a pharmaceutical composition comprising one or both of the inhibitors as described herein.

Exemplary conditions or disorders that can be treated with inhibitors of TGFβ and of PD-1 (e.g., antibodies of the present disclosure) include cancers, such as esophageal cancer, pancreatic cancer, metastatic pancreatic cancer, metastatic adenocarcinoma of the pancreas, bladder cancer, stomach cancer, fibrotic cancer, glioma, malignant glioma, diffuse intrinsic pontine glioma, recurrent childhood brain neoplasm renal cell carcinoma, clear-cell metastatic renal cell carcinoma, kidney cancer, prostate cancer, metastatic castration resistant prostate cancer, stage IV prostate cancer, metastatic melanoma, melanoma, malignant melanoma, recurrent melanoma of the skin, melanoma brain metastases, stage IIIA skin melanoma; stage IIIB skin melanoma, stage IIIC skin melanoma; stage IV skin melanoma, malignant melanoma of head and neck, lung cancer, non small cell lung cancer (NSCLC), squamous cell non-small cell lung cancer, breast cancer, recurrent metastatic breast cancer, hepatocellular carcinoma, hodgkin's lymphoma, follicular lymphoma, non-hodgkin's lymphoma, advanced B-cell NHL, HL including diffuse large B-cell lymphoma (DLBCL), multiple myeloma, chronic myeloid leukemia, adult acute myeloid leukemia in remission; adult acute myeloid leukemia with Inv(16)(p13.1q22); CBFB-MYH11; adult acute myeloid leukemia with t(16;16)(p13.1;q22); CBFB-MYH11; adult acute myeloid leukemia with t(8;21)(q22;q22); RUNX1-RUNX1T1; adult acute myeloid leukemia with t(9;11)(p22;q23); MLLT3-MLL; adult acute promyelocytic leukemia with t(15;17)(q22;q12); PML-RARA; alkylating agent-related acute myeloid leukemia, chronic lymphocytic leukemia, richter's syndrome; waldenstrom macroglobulinemia, adult glioblastoma; adult gliosarcoma, recurrent glioblastoma, recurrent childhood rhabdomyosarcoma, recurrent ewing sarcoma/peripheral primitive neuroectodermal tumor, recurrent neuroblastoma; recurrent osteo sarcoma, colorectal cancer, MSI positive colorectal cancer; MSI negative colorectal cancer, nasopharyngeal nonkeratinizing carcinoma; recurrent nasopharyngeal undifferentiated carcinoma, cervical adenocarcinoma; cervical adenosquamous carcinoma; cervical squamous cell carcinoma; recurrent cervical carcinoma; stage IVA cervical cancer; stage IVB cervical cancer, anal canal squamous cell carcinoma; metastatic anal canal carcinoma; recurrent anal canal carcinoma, recurrent head and neck cancer; carcinoma, squamous cell of head and neck, head and neck squamous cell carcinoma (HNSCC), ovarian carcinoma, colon cancer, gastric cancer, advanced GI cancer, gastric adenocarcinoma; gastroesophageal junction adenocarcinoma, bone neoplasms, soft tissue sarcoma; bone sarcoma, thymic carcinoma, urothelial carcinoma, recurrent merkel cell carcinoma; stage III merkel cell carcinoma; stage IV merkel cell carcinoma, myelodysplastic syndrome and recurrent mycosis fungoides and Sezary syndrome.

Exemplary cancers that can be treated with the antibody combination according to the present invention include cancers, such as lung adenocarcinoma, mucinous adenoma, ductal carcinoma of the pancreas and colorectal carcinoma, brain lower grade glioma, breast invasive carcinoma, glioblastoma multiforme, melanoma, thyroid, rectum adenocarcinoma, kidney cancer, renal cancer, liver cancer, acute myeloid leukemia, gastric adenocarcinoma, esophageal adenocarcinoma, uterine corpus endometrioid carcinoma, bladder cancer, kidney cancer, prostate cancer, oral cancer, large intestine cancer and lymphoma.

It has been observed that many human tumors (deMartin et al., EMBO J., 6: 3673 (1987), Kuppner et al., Int. J. Cancer, 42: 562 (1988)) and many tumor cell lines (Derynck et al., Cancer Res., 47: 707 (1987), Roberts et al., Br. J. Cancer, 57: 594 (1988)) produce TGFβ and suggests a possible mechanism for those tumors to evade normal immunological surveillance.

TGFβ isoform expression in cancer is complex and variable with different combinations of TGFβ isoforms having different roles in particular cancers. TGFβ molecules can act both as tumor suppressors and tumor promoters. For example, deletion or dowregulation of TGFβ signaling in animals can result in increased breast cancer, intestinal cancer, pancreatic cancer, colon cancer and squamous cell carcinoma, indicating the presence of TGFβ is important to prevent or slow tumor progression (Yang et al., Trends Immunol 31:220-27, 2010). However, overexpression of TGFβ is known to be pro-oncogenic and increased expression is detected in many tumor types (Yang et al., supra)

Additional complexities are also disclosed in U.S. Pat. No. 7,927,593. For example, different TGFβ isoforms appear to be more relevant to different types of cancers. TGFβ1 and TGFβ3 may play a greater role in ovarian cancer and its progression than TGFβ2; while TGFβ1 and TGFβ2 expression is greater in higher grade chondrosarcoma tumors than TGFβ3. In human breast cancer, TGFβ1 and TGFβ3 are highly expressed, with TGFβ3 expression correlating with overall survival, whereas patients with node metastasis and positive TGFβ3 expression have poor prognostic outcomes. However, in colon cancer, TGFβ1 and TGFβ2 are more highly expressed than TGFβ3 and are present at greater circulating levels than in cancer-free individuals. In gliomas, TGFβ2 is important for cell migration.

Infiltration of immune cells into tumor sites is thought to be a common contributing factor to tumor growth. These immune cell infiltrates can have a beneficial effect by helping to clear the tumor, but can also be detrimental effect by enabling tolerance to tumor antigens. It has been shown that TGFβ can affect levels of immune cells in tumors (see e.g., Yang et al., Trends Immunol 31:220-27, 2010; Flavell et al., Nature Immunol 10:554-567, 2010; Nagarau et al., Expert Opin Investig Drugs 19:77-91, 2010). For example, TGFβ suppresses natural killer cells that infiltrate tumors in order to clear tumors from the body. TGFβ also suppresses activity of cytotoxic T cells and CD4+ helper T cells, cell types which assist in clearance of tumors (Yang, supra). TGFβ also plays a role in regulating dendritic cell activity, for example by inhibiting migration into injury sites and presentation of antigen to promote an immune response. Dendritic cells are both responsive to TGFβ and secrete TGFβ. For example, dendritic cells infiltrate tumors and take up the cells, secrete TGFβ and activate regulatory T cells, which in turn can prevent tumor clearance (Flavell et al., supra). Additionally, myeloid derived suppressor cells (MDSC) are a bone marrow derived cells that expand during tumor progression. MDSC inhibit T cell proliferation, suppress dendritic cell maturation, and inhibit natural killer cell activity, thereby helping cells to evade the immune response (Li et al., J Immunol. 182:240-49, 2009). TGFβ has been demonstrated to contribute to the effects of MDSC on inhibiting natural killer cell activity (Li et al., supra; Xiang et al., Int J Cancer 124:2621-33, 2009). The role of the various TGFβ isoforms in each of these immune processes is unclear. Selectively targeting TGFβ isoforms and inhibiting them to varying degrees may be instrumental in modulating the host immune response to combat and clear the tumor.

It is contemplated that the methods herein reduce tumor size or tumor burden in the subject, and/or reduce metastasis in the subject. In various embodiments, the methods reduce the tumor size by 10%, 20%, 30% or more. In various embodiments, the methods reduce tumor size by 10%, 15%, 20%, 25%, 30%, 35%, 40%, 45%, 50%, 55%, 60%, 65%, 70%, 75%, 80%, 85%, 90%, 95% or 100%.

It is contemplated that the methods herein reduce tumor burden, and also reduce or prevent the recurrence of tumors once the cancer has gone into remission.

In various embodiments, the TGFβ antibody and/or PD-1 antibody and combinations thereof or compositions described herein modulates immune cells in a tumor. In some embodiments, the TGFβ antibody and/or PD-1 antibody and combinations thereof or compositions herein increases the number of natural killer (NK) cells in a tumor and/or increases cytolytic activity of NK cells. In various embodiments, the antibodies or compositions described herein decreases the number of regulatory T cells in a tumor and/or inhibits regulatory T cell function. For example, in various embodiments, the antibodies or compositions described herein inhibits ability of Tregs to down-regulate an immune response or to migrate to a site of an immune response.

In various embodiments, the TGFβ antibody and/or PD-1 antibody and combinations thereof or compositions described herein increases the number of cytotoxic T cells in a tumor, and/or enhances CTL activity, e.g., boosts, increases or promotes CTL activity. For example, in various embodiments, the antibodies or compositions described herein increases perforin and granzyme production by CTL and increases cytolytic activity of the CTL.

In various embodiments, the, the TGFβ antibody and/or PD-1 antibody and combinations thereof or compositions described herein increases the number of dendritic cells (DC) in a tumor, and/or inhibits the tolerogenic function (e.g., tolerogenic effect) of dendritic cells. For example, in various embodiments, the antibodies or compositions described herein decreases the tolerogenic effect of CD8+ dendritic cells.

In various embodiments, any of antibodies for TGFβ, XPA.42.068, XPA.42.089 or XPA.42.681 or variants thereof as described herein modulate one or more of the immune activities described above.

In one embodiment, treatment of cancer in an animal in need of said treatment, comprises administering to the animal an effective amount of an inhibitor of TGFβ and an inhibitor of PD-1 or a composition comprising an inhibitor described herein. It is contemplated that the inhibitors are a TGFβ antibody and a PD-1 antibody.

The conditions treatable by methods of the present disclosure preferably occur in mammals. Mammals include, for example, humans and other primates, as well as pet or companion animals such as dogs and cats, laboratory animals such as rats, mice and rabbits, and farm animals such as horses, pigs, sheep, and cattle.

Formulation of Pharmaceutical Compositions

To administer inhibitors, e.g., antibodies, of the present disclosure to human or test animals, it is preferable to formulate the inhibitors in a composition comprising one or more pharmaceutically acceptable carriers. The phrase "pharmaceutically or pharmacologically acceptable" refer to molecular entities and compositions that do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like.

In addition, compounds may form solvates with water or common organic solvents. Such solvates are contemplated as well.

The inhibitors are administered by any suitable means, including parenteral, subcutaneous, intraperitoneal, intrapulmonary, and intranasal, and, if desired for local treatment, intralesional administration. Parenteral infusions include intravenous, intraarterial, intraperitoneal, intramuscular, intradermal or subcutaneous administration. In addition, the inhibitors are suitably administered by pulse infusion, particularly with declining doses of the antibody. Preferably the dosing is given by injections, most preferably intravenous or subcutaneous injections, depending in part on whether the administration is brief or chronic. Other administration methods are contemplated, including topical, particularly transdermal, transmucosal, rectal, oral or local administration e.g. through a catheter placed close to the desired site.

Pharmaceutical compositions of the present disclosure containing the inhibitors described herein as an active ingredient may contain pharmaceutically acceptable carriers or additives depending on the route of administration. Examples of such carriers or additives include water, a pharmaceutical acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, glycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used are chosen from, but not limited to, the above or combinations thereof, as appropriate, depending on the dosage form of the present disclosure.

Formulation of the pharmaceutical composition will vary according to the route of administration selected (e.g., solution, emulsion). An appropriate composition comprising the inhibitor, e.g., an antibody, to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers.

A variety of aqueous carriers, e.g., sterile phosphate buffered saline solutions, bacteriostatic water, water, buffered water, 0.4% saline, 0.3% glycine, and the like, and may include other proteins for enhanced stability, such as albumin, lipoprotein, globulin, etc., subjected to mild chemical modifications or the like.

Therapeutic formulations of the inhibitors are prepared for storage by mixing the inhibitor having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Aqueous suspensions may contain the active compound in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate.

The antibodies described herein can be lyophilized for storage and reconstituted in a suitable carrier prior to use. This technique has been shown to be effective with conventional immunoglobulins. Any suitable lyophilization and reconstitution techniques can be employed. It will be appreciated by those skilled in the art that lyophilization and reconstitution can lead to varying degrees of antibody activity loss and that use levels may have to be adjusted to compensate.

The TGFβ and PD-1 antibodies described herein can be prepared and administered as a co-formulation. In one aspect, at least two of the antibodies recognize and bind different antigens. In another aspect, at least two of the plurality of antibodies can specifically recognize and bind different epitopes of the same antigen.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above.

The concentration of antibody in these formulations can vary widely, for example from less than about 0.5%, usually at or at least about 1% to as much as 15 or 20% by weight and will be selected primarily based on fluid volumes, viscosities, etc., in accordance with the particular mode of administration selected. Thus, a typical pharmaceutical composition for parenteral injection could be made up to contain 1 ml sterile buffered water, and 50 mg of antibody. A typical composition for intravenous infusion could be made up to contain 250 ml of sterile Ringer's solution, and 150 mg of antibody. Actual methods for preparing parenterally administrable compositions will be known or apparent to those skilled in the art and are described in more detail in, for example, Remington's Pharmaceutical Science, 15th ed., Mack Publishing Company, Easton, Pa. (1980). An effective dosage of antibody is within the range of 0.01 mg to 1000 mg per kg of body weight per administration.

The pharmaceutical compositions may be in the form of a sterile injectable aqueous, oleaginous suspension, dispersions or sterile powders for the extemporaneous preparation of sterile injectable solutions or dispersions. The suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. The carrier can be a solvent or dispersion medium containing, for example, water, ethanol, polyol (for example, glycerol, propylene glycol, and liquid polyethylene glycol, and the like), suitable mixtures thereof, vegetable oils, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

In all cases the form must be sterile and must be fluid to the extent that easy syringability exists. The proper fluidity can be maintained, for example, by the use of a coating, such as lecithin, by the maintenance of the required particle size in the case of dispersion and by the use of surfactants. It must be stable under the conditions of manufacture and storage and must be preserved against the contaminating action of microorganisms, such as bacteria and fungi. The prevention of the action of microorganisms can be brought about by various antibacterial and antifungal agents, for example, parabens, chlorobutanol, phenol, sorbic acid, thimerosal, and the like. In many cases, it will be desirable to include isotonic agents, for example, sugars or sodium chloride. Prolonged absorption of the injectable compositions can be brought about by the use in the compositions of agents delaying absorption, for example, aluminum monostearate and gelatin.

Compositions useful for administration may be formulated with uptake or absorption enhancers to increase their efficacy. Such enhancers include for example, salicylate, glycocholate/linoleate, glycholate, aprotinin, bacitracin, SDS, caprate and the like. See, e.g., Fix (J. Pharm. Sci., 85:1282-1285 (1996)) and Oliyai and Stella (Ann. Rev. Pharmacol. Toxicol., 32:521-544 (1993)).

Antibody compositions contemplated for use to inhibit target activity, including binding of the target to its cognate receptor or ligand, target-mediated signaling, and the like. In particular, the compositions exhibit inhibitory properties at concentrations that are substantially free of side effects, and are therefore useful for extended treatment protocols. For example, co-administration of an antibody composition with another, more toxic, cytotoxic agent can achieve beneficial inhibition of a condition or disorder being treated, while effectively reducing the toxic side effects in the patient.

In addition, the properties of hydrophilicity and hydrophobicity of the compositions contemplated for use in the present disclosure are well balanced, thereby enhancing their utility for both in vitro and especially in vivo uses, while other compositions lacking such balance are of substantially less utility. Specifically, compositions contemplated for use in the disclosure have an appropriate degree of solubility in aqueous media which permits absorption and bioavailability in the body, while also having a degree of solubility in lipids which permits the compounds to traverse the cell membrane to a putative site of action. Thus, antibody compositions contemplated are maximally effective when they can be delivered to the site of target antigen activity.

Administration and Dosing

In one aspect, methods of the present disclosure include a step of administering a pharmaceutical composition. In certain embodiments, the pharmaceutical composition is a sterile composition.

Methods of the present disclosure are performed using any medically-accepted means for introducing therapeutics directly or indirectly into a mammalian subject, including but not limited to injections, oral ingestion, intranasal, topical, transdermal, parenteral, inhalation spray, vaginal, or rectal administration. The term parenteral as used herein includes subcutaneous, intravenous, intramuscular, and intracisternal injections, as well as catheter or infusion techniques. Administration by, intradermal, intramammary, intraperitoneal, intrathecal, retrobulbar, intrapulmonary injection and or surgical implantation at a particular site is contemplated as well.

In one embodiment, administration is performed at the site of a cancer or affected tissue needing treatment by direct injection into the site or via a sustained delivery or sustained release mechanism, which can deliver the formulation internally. For example, biodegradable microspheres or capsules or other biodegradable polymer configurations capable of sustained delivery of a composition (e.g., a soluble polypeptide, antibody, or small molecule) can be included in the formulations of the disclosure implanted near or at site of the cancer.

Therapeutic compositions may also be delivered to the patient at multiple sites. The multiple administrations may be rendered simultaneously or may be administered over a period of time. In certain cases it is beneficial to provide a continuous flow of the therapeutic composition. Additional therapy may be administered on a period basis, for example, hourly, daily, every other day, twice weekly, three times weekly, weekly, every 2 weeks, every 3 weeks, monthly, or at a longer interval.

Also contemplated in the present disclosure is the administration of multiple agents, such as the antibody compositions in conjunction with a third agent as described herein, including but not limited to a chemotherapeutic agent.

The amounts of inhibitor or antibody composition in a given dosage may vary according to the size of the individual to whom the therapy is being administered as well as the characteristics of the disorder being treated. In exemplary treatments, it may be necessary to administer about 1 mg/day, 5 mg/day, 10 mg/day, 20 mg/day, 50 mg/day, 75 mg/day, 100 mg/day, 150 mg/day, 200 mg/day, 250 mg/day, 500 mg/day or 1000 mg/day. These concentrations may be administered as a single dosage form or as multiple doses. Standard dose-response studies, first in animal models and then in clinical testing, reveals optimal dosages for particular disease states and patient populations.

Also contemplated in the present disclosure, the amounts of TGFβ inhibitor and PD-1 inhibitor in a given dosage may vary according to the size of the individual to whom the therapy is being administered as well as the characteristics of the disorder being treated. Both inhibitor compositions can be administered in a dose range of 0.1 to 15 mg as an intravenous infusion over 30-60 minutes every 1-4 weeks until disease progression or unacceptable toxicity. In various embodies the dose can be 1,2,3,4,5,6,7,8,9,10 mg/kg.

It will also be apparent that dosing may be modified if traditional therapeutics are administered in combination with therapeutics of the disclosure.

Kits

As an additional aspect, the disclosure includes kits which comprise one or more compounds or compositions packaged in a manner which facilitates their use to practice methods of the disclosure. In one embodiment, such a kit includes a compound or composition described herein (e.g., a composition comprising a target-specific antibody alone or in combination with another antibody or a third agent), packaged in a container such as a sealed bottle or vessel, with a label affixed to the container or included in the package that describes use of the compound or composition in practicing the method. Preferably, the compound or composition is packaged in a unit dosage form. The kit may further include a device suitable for administering the composition according to a specific route of administration or for practicing a screening assay. Preferably, the kit contains a label that describes use of the inhibitor compositions.

EXAMPLES

Example 1. TGFβ and PD-1 Inhibitor Combination Therapy of Chemically Induced Cutaneous Squamous Cell Carcinoma (cSCC)

To demonstrate the effect of TGFβ and PD-1 inhibitor combination therapy, FVB mice were subcutaneously injected with chemically-induced KrasG13C-driven cSCC tumor line 168 (cultured ≤2 passages in vitro). When tumors reached ~3-5 mm diameter (approximately 2-3 weeks post-implantation), mice were treated with either anti-PD-1 (α-PD-1) antibody alone (250 µg, Clone: RMP1-14, Cat. no.: BE0146, BioXCell), pan-specific α-TGFβ1,2,3 (anti-TGFβ3) antibody (200 µg) alone or α-PD-1 and pan-specific α-TGFβ1,2,3 antibodies combined via intraperitoneal injection (i.p.), three treatments at 4 day intervals (mice injected on day 0, day 4 and day 8, n=7 per arm). Tumor sizes were subsequently measured using a caliper. α-PD-1 monotherapy inhibited tumor growth compared with control mice but the tumor regression was not sustained after 12-14 days. Unlike α-PD-1 monotherapy, α-TGFβ monotherapy showed robust and sustained activity (>12-14 days). While both α-PD-1 and α-TGFβ mono-therapy induced tumor regression compared to matched IgG control-treated mice, the combined effect of α-PD-1 and α-TGFβ on average was greater than that of either reagent alone (FIG. 1A, $*P<0.05$, $P<0.01$, $*P<0.0001$). Tumors were separated into α-PD-1 progressors or resistant ('res'), α-PD-1 responders or sensitive ('sens'), α-TGFβ responders (TGFb) and α-PD-1/α-TGFβ combination responders (PD-1 TGFb). Levels of immune cell markers in these tumors were measured as a percentage of live cells and as a percentage of CD45+ cells to assess changes in populations of tumor infiltrating immune cells in response to drug. CD45+, Natural killer (NK) cells, regulatory T (Treg) cells, CD4+ and CD8+ T cells were measured by Fluorescence-activated cell sorting (FACS) in 2-3 tumors per cohort at day 8, following the third treatment with inhibitors (FIGS. 1B and 1C). Elevated CD8+ cell numbers were utilized as a biomarker of α-TGFβ and α-PD-1 inhibitor responsiveness.

Example 2. Differential Responses of Individual Tumors to Immunotherapy

Data from FIG. 1 were segregated into "responders" and "progressors" to demonstrate the range of responses to α-PD-1 and/or α-TGFβ immunotherapy (FIG. 2). In the case of α-TGFβ monotherapy and α-PD1 and α-TGFβ combinational therapy, regression of the implanted tumor was observed in 3 out of the 7 treated mice. Furthermore with the combined α-PD1 and α-TGFβ treatment, complete tumor regression was observed in ~50% cases, with no further tumor outgrowth four weeks post-dosing with no additional drug doses (i.e., a sustained reduction in tumor size).

These results show that the combination of α-TGFβ antibody and α-PD-1 antibody is more effective than single antibody treatment at promoting tumor regression, and surprisingly, at preventing the recurrence of cancer.

Example 3. Reduction in Tumor Size in with α-TGFβ/α-PD-1 Combinational Therapy in Chemically-Induced (DMBA-TPA) Cutaneous Squamous Cell Carcinoma (cSCC) Mice In addition to the use of allograft models, the anti-tumor effects of pan-specific α-TGFβ1,2,3 α-TGFβ3/α-PD-1 combinational therapy were also assessed using a mouse skin model of direct chemically-induced carcinogenesis. The DMBA-TPA (12-Otetradecanoyl-phorbol-13-acetate) induced cSCCs model has been well characterized (Balmain A et al., Princess Takamatsu Symp., 22:97-108, 1991; Burns P A et al., Oncogene, 6(12):2363-9, 1991; Yuspa S H et al., Dermatol Symp Proc., 1(2):147-50, 1996; Frame S et al., Philos Trans R Soc Lond B Biol Sci. 353(1370):839-45, 1998) and used extensively to identify genetic and molecular mechanisms of cancer initiation and progression that would not have been attainable from studying human cancer or more simple models, such as tumor allografts. The model is initiated by DMBA-mutation of Hras codon 61 in >90% of tumors in wild type mice (Quintanilla M et al., Nature., 322(6074): 78-80, 1986). Subsequent multiple biweekly treatments with the tumor promoter, TPA, stimulate the outgrowth of benign premalignant papillomas. A proportion of papillomas progress to carcinomas over a period of 4-12 months, and in some cases to highly invasive spindle tumors that have lost many of the characteristics of their epithelial cell.

Using a bioluminescence reporter strain of luciferase knockin mice (p16(LUC)), the growth of chemically-induced cSCCs was measured preceding and then after treatment of the mice with a combination of α-PD1 and α-TGFβ antibodies. p16-LUC mice report the expression of p16 (INK4a) gene, a tumor suppressor in Ras-driven tumor cells. The reporter is activated by early neoplastic events, enabling visualization of tumors and measurement of tumor size using a IVIS optical imaging system.

Tumors were initiated by topically treating 3 mice with DMBA twice in the first week and TPA for the following 20 weeks with carcinoma outgrowth observed at ~30 weeks. Surgical resection of carcinomas was performed at 32 weeks after tumor initiation with DMBA treatment. Mice were imaged and tumor sizes were measured 5 times (Pre-surgical resection: at week 0 and post-surgical resection: at weeks 8, 12, 21 and 27).

When all mice had approximately 15 mm carcinomas and small lung metastases (3×3 mm), carcinomas were resectioned and mice were treated with α-PD-1 antibody (250 µg, Clone: RMP1-14, BioXCell) and α-TGFβ antibody (200 µg) combined via intraperitoneal injection (i.p.), three treatments at 4 day intervals (mice injected on day 8, day 12 and day 16, n=3). Tumor sizes were subsequently measured using a luminescence imager. Combinational α-PD-1 and α-TGFβ antibody treatments resulted in tumor regression in all 3 mice.

Figure 4:
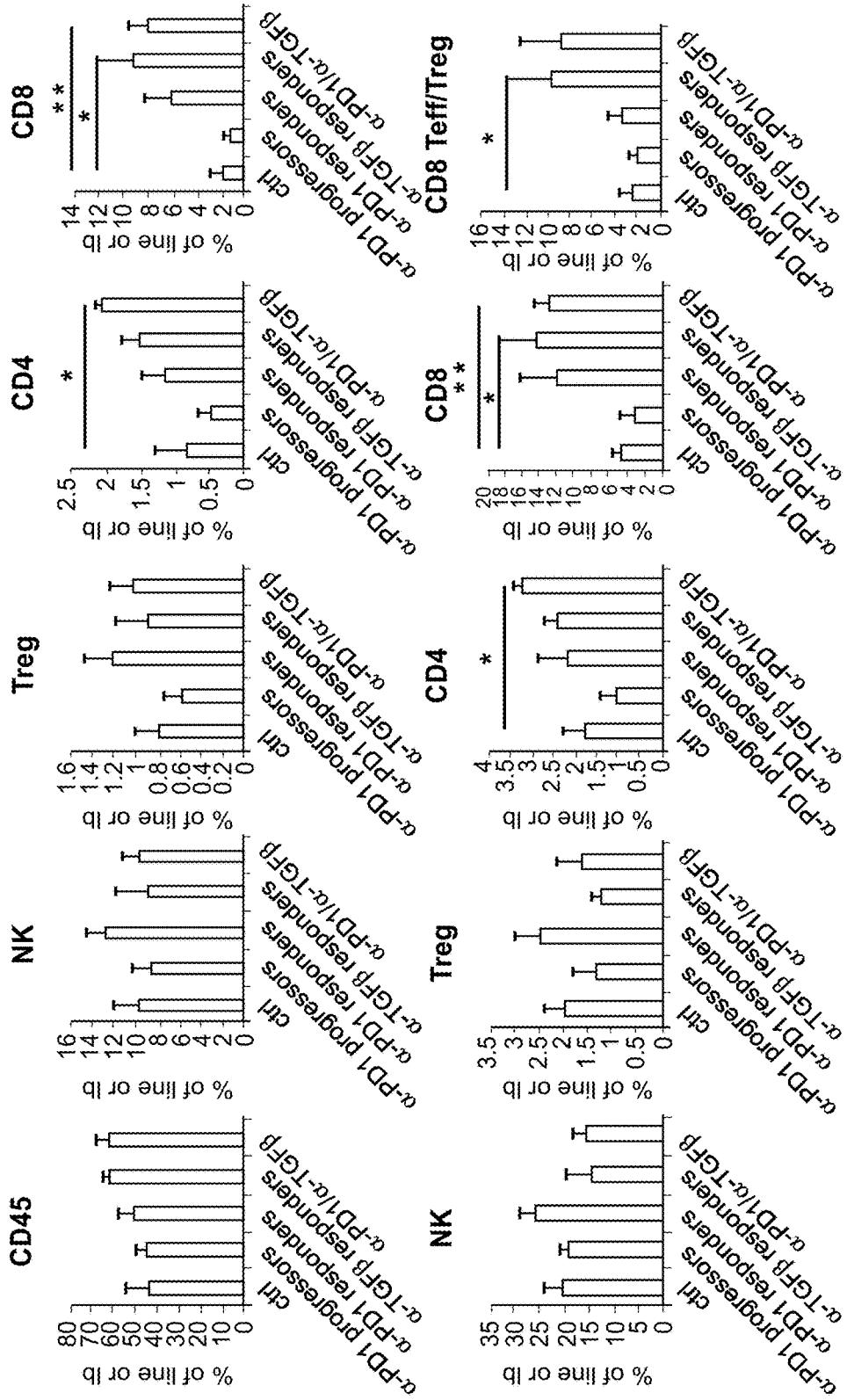
FIG. 4 shows tumor immunotyping measurement of CD45+, Natural killer (NK) cells, regulatory T (Treg) cells, CD4+ and CD8+ T cells tumors chemically-induced (DMBA-TPA) cutaneous squamous cell carcinoma (cSCC) mice, represented as a percentage of viable cells and as a percentage of CD45+ cells.

Carcinomas that were resectioned from mice were immunotyped for cell markers CD45+, Natural killer (NK) cells, regulatory T (Treg) cells, CD4+ and CD8+ T cells were measured by FACS in tumors following the third treatment with inhibitors. Tumors were separated into α-PD-1 progressors, α-PD-1 responders, α-TGFβ responders and α-PD-1/α-TGFβ combination responders. Levels of immune cell markers in these tumors were measured as a percentage of live cells and as a percentage of CD45+ cells to assess changes in populations of tumor infiltrating immune cells in response to drug (FIG. 4). Tumors which responded to treatment with α-PD-1 alone, α-TGFβ alone and α-PD-1/α-TGFβ in combination showed significantly increased levels of CD4+ and CD8+ T cells, with α-PD-1/α-TGFβ in combination responsive tumors showing even higher levels of CD4+ T cell subsets. In addition, α-TGFβ alone and α-PD-1/α-TGFβ in combination responsive tumors showed CD8+ T effector (Teff)/Tregulator (Treg) CD45+ cells. Elevated CD8+ T cell numbers were utilized as a biomarker of α-TGFβ and α-PD-1 inhibitor responsiveness.

Figure 5:
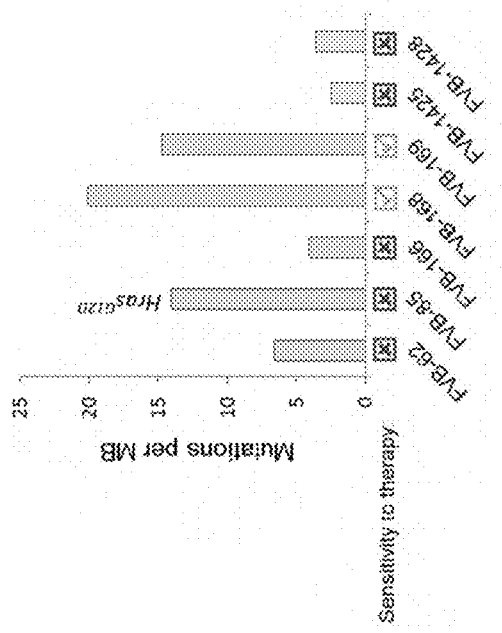
FIG. 5 shows the number of mutations per megabase (MB) and sensitivity to TGFβ and PD-1 inhibitor monotherapy and combinational therapy for chemically-induced (DMBA/TPA) Kras- and Hras-driven (FVB-62, FVB-85, FVB-166, FVB-168, FVB-169) and genetically-initiated (GEMM) Kras-driven cSCC cell lines (FVB-1425, FVB-1428) in syngeneic FVB/N mice.

Example 4. Chemically Induced Kras-Driven SCC Tumors with the Greatest Mutational Load Respond to α-PD1 and α-TGFβ Monotherapy and Combinational Therapy TGFβ and PD-1 inhibitor monotherapy and combinational therapy were evaluated using chemically-induced (DMBA/TPA) Kras- and Hras-driven versus genetically-initiated (GEMM) Kras-driven cSCC cell lines in syngeneic FVB/N mice. Chemically-induced tumor cell lines often possess more mutations than genetically induced cell lines. These higher mutation numbers, are more similar to the number of mutations in human tumors (Westcott P W et al., Nature, 517: 489-92, 2015). The following chemically-induced cell lines: FVB-62, FVB-85, FVB-166, FVB-168, FVB-169 were compared with the following Kras-driven GEMM-initiated models of cSCC: FVB-1425, FVB-1428, using the methods described in example 1, para. [281] with mice treated twice with α-PD1 monotherapy, α-TGFβ monotherapy or α-PD-1 and α-TGFβ antibodies combined (or control antibodies) once on day 0 and once on day 4 followed by tumor immunotyping on days 6-10. Results of these experiments showed that only chemically-induced Kras-driven SCC tumors reported to harbor the greatest mutational load (i.e. greater number of mutations per MB, which are more representative of human tumors) responded to pan-specific α-TGFβ1,2,3 and α-PD1 monotherapy and combinational therapy (FIG. 5). The treatment sensitive, chemically induced SCC tumor cell lines were FVB-168 and FVB-169 with KrasG13R mutations.

Figure 6A:
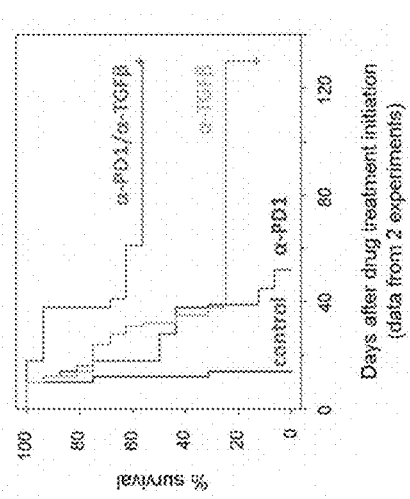
FIG. 6A-6C show the response of the chemically-induced SCC tumor cell line, FVB-168, to pan specific α-TGFβ1, 2, 3 and α-PD1 monotherapy and combinational therapy.
Figure 6B:
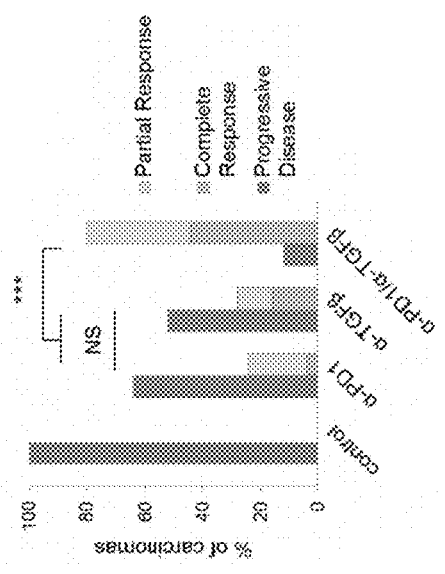

Using the chemically-induced SCC tumor cell line FVB-168, response to pan specific α-TGFβ1,2,3 and α-PD1 monotherapy and combinational therapy was evaluated by measuring the reduction in carcinomas and expressed as a partial response, a complete response or progressive disease (FIG. 6A, data from two independent experiments). Pan-specific α-TGFβ1,2,3 and α-PD1 monotherapy inhibited disease progression by ~40-50%. No significant difference in disease was observed between either therapy alone. However, pan-specific α-TGFβ1,2,3 and α-PD1 combinational therapy was found to be significantly more effective at inhibiting disease progression compared with either pan-specific α-TGFβ1,2,3 or α-PD1 monotherapy. Pan-specific α-TGFβ1,2,3 and α-PD1 combinational therapy resulted in a ~90% reduction in disease progression compared with control animals and was associated with better overall survival (FIG. 6B).

Figure 6C:
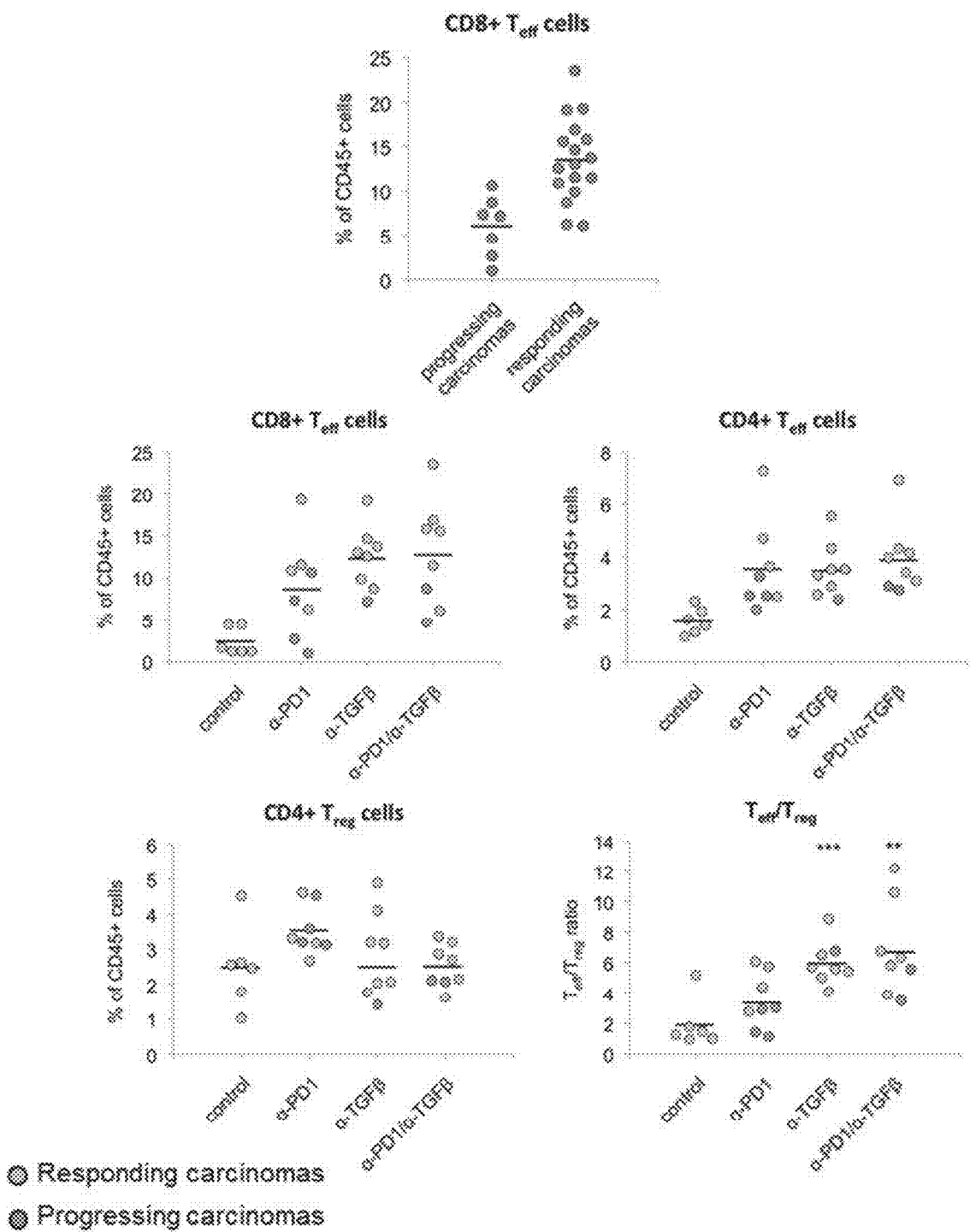

Tumors were separated into progressing carcinomas (i.e., tumor(s) continuing to grow) or responding carcinomas (i.e., tumor growth inhibited by therapy). Levels of immune cell markers in these tumors were measured as a percentage of CD45+ cells to assess changes in populations of tumor infiltrating immune cells in response to drug. CD8+ effector ($T_{eff}$), CD4+ effector ($T_{eff}$), CD4+ regulatory T ($T_{reg}$) cells and the ratio of $T_{eff}/T_{reg}$ were measured by Fluorescence-activated cell sorting (FACS) in tumors per cohort between days 6-10 following treatment with α-PD1 monotherapy, pan-specific α-TGFβ1,2,3 monotherapy or α-PD-1 and pan-specific α-TGFβ1,2,3 combined (or control antibodies). α-TGFβ and α-PD-1 inhibition resulted in expansion of CD8+ and CD4+ T effector cells (FIG. 6C).

These results show that tumors that have characteristics similar to human tumors are highly responsive to treatment with a combination of TGFβ and PD-1 inhibitors and that the combination therapy reduces overall progression of disease. TGFβ/PD-1 inhibitor combination therapy also changes the immunological profile of cells in the tumors to a more favorable effector T cell to regulatory T cell ratio (Teff/Treg).

Example 5. Comparison of TGFβ1,2 Specific and Pan-Specific TGFβ1,2,3 Antibodies and α-PD-1 Combination Therapy in Allograft Tumor Model In order to compare the effects of antibodies that block TGFβ1,2 and 3 with those that block only TGFβ1,2, either as a monotherapy or in PD-1 inhibitor combination therapy, pan-specific α-TGFβ1,2,3 and TGFβ1,2 specific antibodies were assayed in an allograft model of Kras-driven SCC.

Figure 7:
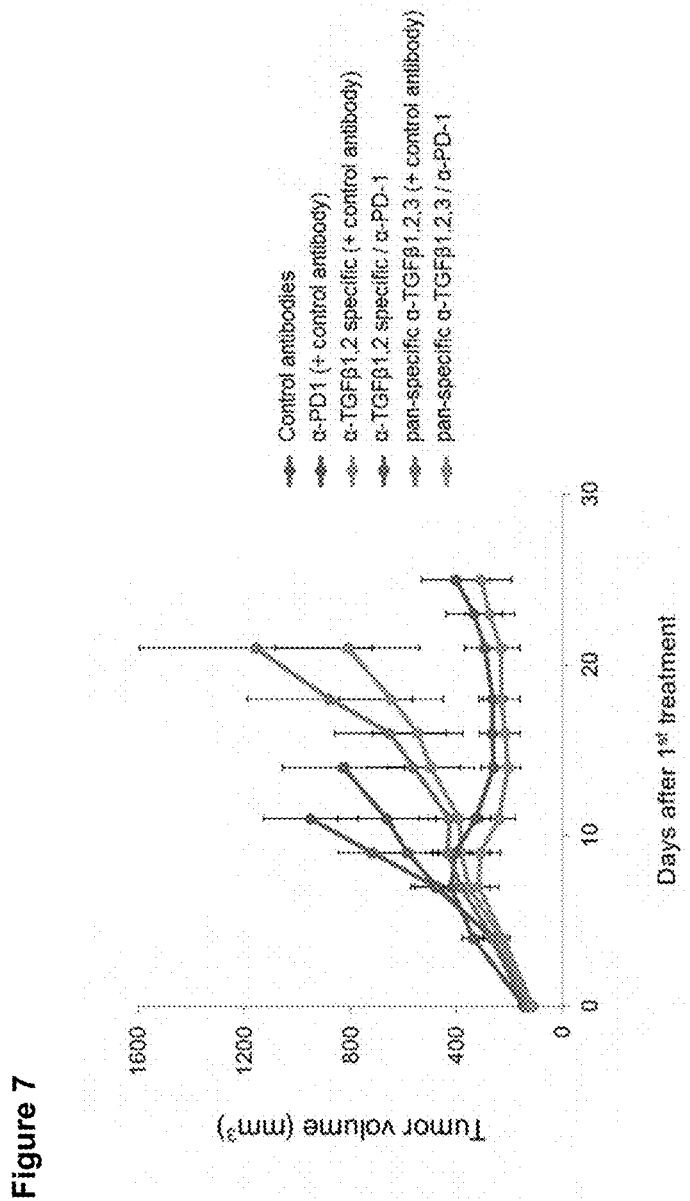
FIG. 7 shows the tumor inhibition in an allograft mouse model with TGFβ1,2 specific, pan-specific TGFβ1,2,3, and PD-1 inhibitor mono- and combination therapy. Represented as tumor volume (mm3) over 0-25 days post the indicated treatments.

FVB mice (n=70) were subcutaneously injected with the cSCC tumor line, Hras168 ($1.25 \times 10^4$ cells). Once tumors were palpable (~0.5 cm diameter, ~2 weeks post-implantation), mice were sorted into six experimental arms (n=9-10 per arm) containing mice of similar body weight and tumor size. Mice were treated with three consecutive doses at day 0, day 4 and day 8, with 200 µg per dose of either pan-specific α-TGFβ1,2,3 or α-TGFβ1,2 and/or 250 µg α-PD-1 per dose and/or matched control antibodies at the same concentrations. The six experimental arms included: 1) control antibodies; 2) α-PD1; 3) α-TGFβ1,2 specific; 4) α-TGFβ1,2 specific and α-PD-1 combined; 5) pan-specific α-TGFβ1,2,3; 6) pan-specific α-TGFβ1,2,3 antibody and α-PD-1 combined via intraperitoneal injection (i.p.). Tumor sizes were subsequently measured using a caliper. Both pan-specific α-TGFβ1,2,3 and α-TGFβ1,2 monotherapies inhibited tumor growth (i.e., reduced tumor size) compared to controls and were both more efficacious than the α-PD-1 antibody alone. Furthermore, both pan-specific α-TGFβ1,2,3 and α-TGFβ1,2 antibodies showed comparable anti-tumor activity to each other in both monotherapy and in combination therapy with α-PD-1 (FIG. 7).

These results show that an antibody that can block either TGFβ1,2,3 isoforms or TGFβ1,2 isoforms is effective in combination with a PD-1 inhibitor in reducing tumor burden in a subject.

Numerous modifications and variations in the disclosure as set forth in the above illustrative examples are expected to occur to those skilled in the art. Consequently only such limitations as appear in the appended claims should be placed on the disclosure.

What is claimed:

1. A method for treating cancer or reducing the recurrence of cancer comprising administering to a subject having cancer or who has had cancer, in therapeutically effective amounts, an inhibitor of transforming growth factor beta (TGFβ) and an inhibitor of Programmed cell death protein 1 (PD-1), wherein the PD-1 inhibitor is an anti-PD-1 antibody; and
wherein the TGFβ inhibitor is an antibody that binds TGFβ comprising:
a) a heavy chain CDR1 amino acid sequence set forth in SEQ ID NO: 19;
b) a heavy chain CDR2 amino acid sequence set forth in SEQ ID NO: 20;
c) a heavy chain CDR3 amino acid sequence set forth in SEQ ID NO: 21;
d) a light chain CDR1 amino acid sequence set forth in SEQ ID NO: 22;
e) a light chain CDR2 amino acid sequence set forth in SEQ ID NO: 23; and
f) a light chain CDR3 amino acid sequence set forth in SEQ ID NO: 24.

2. The method of claim 1, wherein the antibody binds TGFβ1, TGFβ2 and TGFβ3.

3. The method of claim 1, wherein the antibody binds to TGFβ1 and TGFβ2 with greater affinity than to TGFβ3.

4. The method of claim 2, wherein the TGFβ antibody binds to TGFβ1, TGFβ2 and TGFβ3 with an affinity Kd from 10-6 M to 10-12 M.

5. The method of claim 1 wherein the TGFβ inhibitor is an antibody that comprises an amino acid sequence at least 95% identical to a heavy chain variable region amino acid sequence set forth in SEQ ID NO: 6 and comprises HCDR1, HCDR2 and HCDR3 amino acid sequences set out in SEQ ID NO: 19-21.

6. The method of claim 5 wherein the antibody further comprises an amino acid sequence at least 95% identical to a light chain variable region amino acid sequence set forth in SEQ ID NO: 8 and comprises LCDR1, LCDR2 and LCDR3 amino acid sequences set out in SEQ ID NO: 22-24.

7. The method of claim 4 wherein
the heavy chain variable region amino acid sequence is set forth in SEQ ID NO: 6 and the light chain variable region amino acid sequence is set forth in SEQ ID NO: 8.

8. The method of claim 1 wherein the TGFβ antibody further comprises a heavy chain constant region, wherein the heavy chain constant region is a modified or unmodified IgG, IgM, IgA, IgD, IgE, a fragment thereof, or combinations thereof.

9. The method of claim 8 further comprising a human light chain constant region attached to said light chain variable region.

10. The method of claim 1, wherein the cancer is selected from the group consisting of esophageal cancer, pancreatic cancer, metastatic pancreatic cancer, metastatic adenocarcinoma of the pancreas, bladder cancer, stomach cancer, fibrotic cancer, glioma, malignant glioma, diffuse intrinsic pontine glioma, recurrent childhood brain neoplasm renal cell carcinoma, clear-cell metastatic renal cell carcinoma, kidney cancer, prostate cancer, metastatic castration resistant prostate cancer, stage IV prostate cancer, metastatic melanoma, melanoma, malignant melanoma, recurrent melanoma of the skin, melanoma brain metastases, stage IIIA skin melanoma; stage IIIB skin melanoma, stage IIIC skin melanoma; stage IV skin melanoma, malignant melanoma of head and neck, lung cancer, non small cell lung cancer (NSCLC), squamous cell non-small cell lung cancer, breast cancer, recurrent metastatic breast cancer, hepatocellular carcinoma, hodgkin's lymphoma, follicular lymphoma, non-hodgkin's lymphoma (NHL), advanced B-cell NHL, HL including diffuse large B-cell lymphoma (DLBCL), multiple myeloma, chronic myeloid leukemia, adult acute myeloid leukemia in remission; adult acute myeloid leukemia with Inv(16)(p13.1q22); CBFB-MYH11; adult acute myeloid leukemia with t(16;16)(p13.1;q22); CBFB-MYH11; adult acute myeloid leukemia with t(8;21)(q22;q22); RUNX1-RUNX1T1; adult acute myeloid leukemia with t(9;11)(p22; q23); MLLT3-MLL; adult acute promyelocytic leukemia with t(15;17)(q22;q12); PML-RARA; alkylating agent-related acute myeloid leukemia, chronic lymphocytic leukemia, richter's syndrome; waldenstrom macroglobulinemia, adult glioblastoma; adult gliosarcoma, recurrent glioblastoma, recurrent childhood rhabdomyosarcoma, recurrent ewing sarcoma/peripheral primitive neuroectodermal tumor, recurrent neuroblastoma; recurrent osteosarcoma, colorectal cancer, MSI positive colorectal cancer; MSI negative colorectal cancer, nasopharyngeal nonkeratinizing carcinoma; recurrent nasopharyngeal undifferentiated carcinoma, cervical adenocarcinoma; cervical adenosquamous carcinoma; cervical squamous cell carcinoma; recurrent cervical carcinoma; stage IVA cervical cancer; stage IVB cervical cancer, anal canal squamous cell carcinoma; metastatic anal canal carcinoma; recurrent anal canal carcinoma, recurrent head and neck cancer; carcinoma, squamous cell of head and neck, head and neck squamous cell carcinoma (HNSCC), ovarian carcinoma, colon cancer, gastric cancer, advanced GI cancer, gastric adenocarcinoma; gastroesophageal junction adenocarcinoma, bone neoplasms, soft tissue sarcoma; bone sarcoma, thymic carcinoma, urothelial carcinoma, recurrent merkel cell carcinoma; stage III merkel cell carcinoma; stage IV merkel cell carcinoma, myelodysplastic syndrome and recurrent mycosis fungoides and Sezary syndrome.

11. The method of claim 1 wherein the cancer is selected from the group consisting of non small cell lung carcinoma (NSCLC), head and neck cancer, skin cancer, melanoma and squamous cell carcinoma (SCC).

12. The method of claim 1 comprising reducing tumor size or tumor burden in the subject, optionally wherein the tumor size is reduced by 20% or more, or reducing metastasis in the subject.

13. The method of claim 1 wherein the PD-1 inhibitor and the TGFβ inhibitor are formulated in a pharmaceutical composition.

14. The method of claim 1 wherein the administration reduces the recurrence of cancer in a subject that has received inhibitor therapy.

15. The method of claim 1 wherein the TGFβ inhibitor is administered in a dose range of 0.1 to 15 mg/kg and the PD-1 inhibitor is administered in a dose range from 0.1 to 15 mg/kg.

* * * * *